US012583855B2

(12) United States Patent
Liu et al.

(10) Patent No.: US 12,583,855 B2
(45) Date of Patent: Mar. 24, 2026

(54) RET SELECTIVE INHIBITOR, PREPARATION METHOD THEREFOR AND USE THEREOF

(71) Applicant: SHOUYAO HOLDINGS (BEIJING) CO., LTD., Beijing (CN)

(72) Inventors: Zhihua Liu, Beijing (CN); Dechuang Yuan, Beijing (CN); Kuncheng Chen, Beijing (CN); Baokun Yuan, Beijing (CN); Ren Ren, Beijing (CN); Wangyang Min, Beijing (CN); Xijie Liu, Beijing (CN); Kai Zhang, Beijing (CN); Yongliang Sun, Beijing (CN); Chang Lu, Beijing (CN); Yinghui Sun, Beijing (CN)

(73) Assignee: SHOUYAO HOLDINGS (BEIJING) CO., LTD., Beijing (CN)

( * ) Notice: Subject to any disclaimer, the term of this patent is extended or adjusted under 35 U.S.C. 154(b) by 1109 days.

(21) Appl. No.: 17/626,318

(22) PCT Filed: Jul. 10, 2020

(86) PCT No.: PCT/CN2020/101338
§ 371 (c)(1),
(2) Date: Jan. 11, 2022

(87) PCT Pub. No.: WO2021/008455
PCT Pub. Date: Jan. 21, 2021

(65) Prior Publication Data

US 2022/0289740 A1 Sep. 15, 2022

(30) Foreign Application Priority Data

Jul. 12, 2019 (CN) ......................... 201910627353.7
Sep. 3, 2019 (CN) ......................... 201910825867.3

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 10,174,027 | B2 | 1/2019 | Andrews et al. |
| 10,584,124 | B2 | 3/2020 | Metcalf et al. |
| 2018/0133200 | A1 | 5/2018 | Andrews et al. |
| 2019/0262322 | A1 | 8/2019 | Reynolds et al. |

FOREIGN PATENT DOCUMENTS

| | | | |
|---|---|---|---|
| CN | 108349969 | A | 7/2018 |
| CN | 111285886 | A | 6/2020 |
| CN | 112368283 | A | 2/2021 |
| CN | 113474343 | A | 10/2021 |
| EP | 3950685 | A1 | 2/2022 |
| EP | 3971187 | A1 | 3/2022 |
| JP | 2018532690 | A | 11/2018 |
| KR | 1020220008322 | A | 1/2022 |
| WO | 2017011776 | A1 | 1/2017 |
| WO | 2018071447 | A1 | 4/2018 |
| WO | 2018136661 | A1 | 7/2018 |
| WO | 2019075108 | A1 | 4/2019 |
| WO | 2019075114 | A1 | 4/2019 |
| WO | 2020114388 | A1 | 6/2020 |
| WO | 2020114487 | A1 | 6/2020 |
| WO | 2020200316 | A1 | 10/2020 |
| WO | 2020228756 | A1 | 11/2020 |
| WO | 2021115457 | A1 | 6/2021 |

OTHER PUBLICATIONS

European Patent Office, "Partial Supplementary European Search Report" , From Application No. 20840300.6, Dated Jun. 24, 2022, pp. 13.
European Patent Office, "Supplementary European Search Report" , From Application No. 20840300.6, Dated Sep. 28, 2022, pp. 12.
Japan Patent Office, "Notice of Allowance" From Application No. 2022-501373, Dated Jun. 29, 2023, pp. 3, In Japanese.
Japan Patent Office, "Office Action" From Application No. 2022-501373, Dated Jan. 30, 2023, pp. 6, In Japanese.
Korea Patent Office, "Notice of Allowance" , From Application No. 10-2022-7000624, Dated Oct. 7, 2024, pp. 7, In Korean.
Korea Patent Office, "Office Action" , From Application No. 10-2022-7000624, Dated Feb. 5, 2024, pp. 14, In Korean.

(Continued)

*Primary Examiner* — Sun Jae Yoo
(74) *Attorney, Agent, or Firm* — Fredrikson & Byron, P.A.

(57) ABSTRACT

The present invention provides an RET selective inhibitor and preparation method and use thereof; the present invention provides a compound of formula (1) and a pharmaceutically accepted salt, solvate, polymorph, or tautomer thereof, a composition comprising these compounds, and use of these compounds in the treatment of diseases related to RET.

(I)

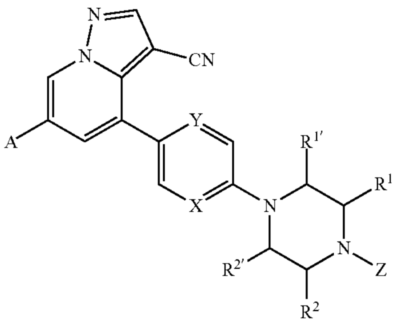

1 Claim, No Drawings

(56) References Cited

OTHER PUBLICATIONS

China Patent Office, "First Chinese Office Action" , From Application No. 202080048596.6, Dated Feb. 12, 2023, pp. 7.
China Patent Office, "Notice of Allowance" , From Application No. 202080048596.6, Dated Jul. 24, 2023, pp. 1.
China Patent Office, "Second Chinese Office Action" , From Application No. 202080048596.6, Dated Jun. 17, 2023, pp. 5.
European Patent Office, "Communication pursuant to Article - 94(3)" , From Application No. 20840300.6, Dated Jun. 26, 2024, pp. 5.
PCT International Search Report (English Translation) for Intl. App. No. PCT/CN2020/101338, from which the instant application is based, 4 pgs.
"2068064-80-0" STN Registry, Feb. 8, 2017 (Feb. 8, 2017), 1 pg.
"2068064-78-6" STN Registry, Feb. 8, 2017 (Feb. 8, 2017), 1 pg.
"2068064-76-4" STN Registry, Feb. 8, 2017 (Feb. 8, 2017), 1 pg.
"2068064-66-2" STN Registry, Feb. 8, 2017 (Feb. 8, 2017), 1 pg.
"2068061-77-6" STN Registry, Feb. 8, 2017 (Feb. 8, 2017), 1 pg.

RET SELECTIVE INHIBITOR, PREPARATION METHOD THEREFOR AND USE THEREOF

CROSS-REFERENCE TO RELATED APPLICATIONS

This application is a National Stage filing from International Patent Application No. PCT/CN2020/101338, filed Jul. 10, 2020, which claims priority to Chinese Patent Application No. 201910627353.7, filed on Friday, Jul. 12, 2019, entitled "RET Selective Inhibitor and Preparation therefor and Use Thereof", and to Chinese Patent Application No. 201910825867.3, filed on Tuesday, Sep. 3, 2019, entitled "RET Selective Inhibitor and Preparation therefor and Use Thereof", the entire disclosures of which are incorporated herein by reference in their entirety.

TECHNICAL FIELD

The invention relates to compounds for selective inhibition of RET protein activity, and also relates to a preparation method of the compounds and a use of pharmaceutical composition thereof.

BACKGROUND ART

RET is a proto-oncogene located on chromosome 10. The RET protein encoded by the RET gene is a receptor tyrosine kinase (RTK) present on cell membranes, belonging to the cadherin superfamily, which plays essential roles in the normal development of peripheral sympathetic and parasympathetic nervous system in the brain, and the production of calcitonin by thyroid C cells, and is required by thyroid and lung as well as hematopoietic progenitor cells and other tissues (*Nat. Rev. Cancer* 2014; 14(3):173-86).

The domain composition of RET proteins is identical to other protein tyrosine kinases, containing a typical extracellular domain, a transmembrane segment, followed by an intracellular juxtamembrane segment, a kinase domain, and a carboxy-terminal tail. The extracellular domain contains four cadherin-like domain (CD1/2/3/4) repeats of about 110 amino acid residues and a cysteine-rich segment of about 150 amino acid residues immediately adjacent to the transmembrane segment, with an extracellular $Ca^{2+}$ binding site between CD2 and CD3 (*J. Biol. Chem.* 2001:276(38): 35808-35817).

RET is the only receptor protein tyrosine kinase with a cadherin-like domain. The mechanism of activation of RET requiring an additional GDNF family receptor (GDNF/NTRN/ARTN/PSP)-GFR co-receptor (GFR 1/2/3/4) differs from that of other protein tyrosine kinases having the same domain composition. Members of the GDNF family are typical disulfide-bonded homodimers, and a binary complex occurs during the interaction of a GDNF homodimer with two GFR complexes, then interacts with two RET receptors, ultimately forming a hexameric complex consisting of two receptors, two co-receptors, and a ligand dimer (*Nat. Rev. Cancer* 2014; 14(3):173-86). In the absence of ligand-mediated stimulation. RET is in a non-phosphorylated inactive state. When the RET protein binds to the ligand GDNF, phosphorylation of the RET protein receptor occurs, allowing RET to enter the activated state. Activated RET will phosphorylate its substrate, resulting in activation of signaling pathways downstream. The signaling pathways involved by RET proteins include PI3K-AKT-mTOR pathway and RAS-RAF-MEK-ERK pathway. The PI3K-AKT-mTOR pathway involved in cell survival, while the RAS-RAF-MEK-ERK pathway involved in cell proliferation. Therefore, RET protein plays a role in cell survival, migration, and proliferation (*Cell* 2010; 141(7):1117-1134; *Cell. Signal.* 2014; 26(8): 1743-1752).

Mutations in the ret gene encoding RET protein kinases, including activating point mutations and gene fusions, may lead to excessive activation of RET signaling pathways and uncontrolled proliferation of cells, leading to the development of diseases such as malignancies. Chromosomal rearrangement of the ret gene which is associated with the incidence of papillary thyroid carcinoma may lead to a split in the middle of the ret gene. The kinase domain of the rt gene is fused with more than ten different genes, such as kif5b, ccdc6, ncoa4, forming a fusion gene driving tumor proliferation (*Transl Lung Cancer Res.* 2015; 4(2):156-164), ret gene fusion occurs in 5%-40% of papillary thyroid carcinoma (PTCs), and ret gene rearrangement in papillary thyroid carcinoma is related to ionizing radiation, i.e. the cancer occurs in the environment with nuclear radiation, etc. ret gene fusions caused by chromosomal rearrangements also occur in non-small cell lung cancer (NSCLC), with a frequency about 11-2%. At present, the fusion partner genes of four ret genes have been identified, respectively kif5b, ccdc6, ncoa4, and trim33, with kif5b-et fusion as the most common form (*Oncologist.* 2013:18(7):865-875). Activation mutations of ret gene caused by site mutagenesis of ret gene such as V804M and M918T, also lead to tumorigenesis, mainly occurring in multiple endocrine tumors (MEN2A, MEN2B) and medullary thyroid carcinoma (MTC) (*Ann Oncol.* 2016:27(7):1286-1291), ret gene mutations in germ cells occur in almost all hereditary medullary thyroid carcinomas, including multiple endocrine neoplasia type 2, ret gene mutations also occur in 50% of acquired thyroid gland medullary carcinomas (*Ann Oncol.* 2016; 27(7):1286-1291).

Currently, in the United States, the estimated number of new cases of tumors carrying RET mutations or RET fusion proteins is about 10,000 per year, which is approximately the same as the incidence of chronic myeloid leukemia (*Pharmacological Research* 2018:128:1-17). Several drugs for RET have been approved by the FDA for the treatment of cancer: Cabozantimb, Vandetanib. Lenvatinib. Sorafenib, Alectinib, etc., all of which are multi-kinase inhibitors with anti-RET activity, have relatively poor clinical efficacy for RET targeted therapy, and are accompanied by toxic side effects due to significant inhibition on other kinases such as vascular endothelial growth factor receptor 2 (VEGFR2) (*Nat Rev Clin Oncol.* 2018; 15(3):151-167). Thus, the development of highly selective RET inhibitors has attracted research interest from numerous pharmaceutical companies, and the development of specific RET inhibitors has become an emerging therapeutic approach to improve the therapeutic efficacy of RET-driven cancers.

SUMMARY OF THE INVENTION

The present invention provides an RET selective inhibitor, which is a compound represented by Formula (I) or a pharmaceutically acceptable salt, solvate, polymorph or tautomer thereof. The present invention also provides a series of compounds represented by Formula (1) and pharmaceutically acceptable salts, solvates, polymorphs or isomers thereof, pharmaceutical compositions containing the compounds, and a method of treating diseases with such compounds.

In one aspect, the present invention provides a compound of Formula (I) or a pharmaceutically acceptable salt, solvate, polymorph or tautomer thereof:

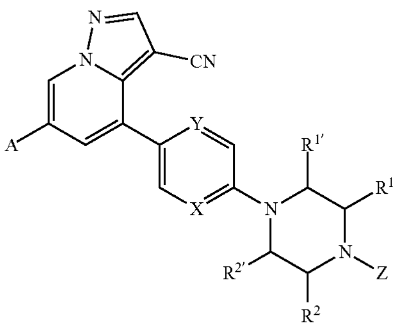

(I)

wherein,

X and Y are independently selected from CH and N;

A is selected from 5-6 membered heteroaryl, 3-12 membered heterocycloalkyl, —O—$C_{1-6}$alkyl, —S—$C_{1-6}$alkyl and —$SO_2$—$C_{1-6}$alkyl, said heteroaryl and heterocycloalkyl can be independently optionally substituted with $C_{1-6}$alkyl, —CN, —OH, —$NR^5R^6$, halogen, —O—$C_{1-6}$alkyl, —S—$C_{1-6}$alkyl, or —$SO_2$—$C_{1-6}$alkyl, said $C_{1-6}$alkyl can be optionally substituted with —OH, halogen, or —(CO)N$(CH_3)_2$, and $R^5$ and $R^6$ are independently selected from H and $C_{1-6}$alkyl;

$R^1$, $R^{1'}$, $R^2$ and $R^{2'}$ are independently H or $C_{1-6}$alkyl, or one of $R^1$ and $R^{1'}$ can be taken together with one of $R^2$ and $R^{2'}$ to form a bond or —$(CH_2)_m$—;

Z is selected from —$(CH_2)_m$—S—$C_{1-6}$alkyl, —(CS)—N$(R^8)_2$,

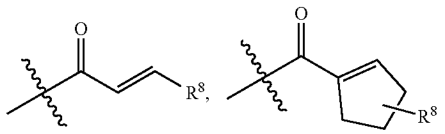

and —$(CH_2)_n$—Ar;

$R^8$ are independently selected from H, $C_{1-6}$alkyl, —O—$C_{1-6}$alkyl and —$(CH_2)_m$—O—$C_{1-6}$alkyl;

Ar is selected from phenyl, pyridyl and pyrimidyl, said phenyl, pyridyl and pyrimidyl can be independently optionally substituted with —O—$C_{1-6}$alkyl, —S—$C_{1-6}$ alkyl, —SO—$C_{1-6}$alkyl, or —$SO_2$—$C_{1-6}$alkyl;

m is independently selected from 1 and 2;

n is selected from 0, 1 and 2;

In some embodiments of the present invention, A is selected from 5-6 membered heteroaryl and 3-12 membered heterocycloalkyl, said heteroaryl and heterocycloalkyl can be independently optionally substituted with $C_{1-6}$alkyl, —CN, —OH, —$NR^5R^6$, halogen, —O—$C_{1-6}$alkyl, —S—$C_{1-6}$alkyl, or —$SO_2$—$C_{1-6}$alkyl, said $C_{1-6}$alkyl can be optionally substituted with —OH, halogen, or —(CO)N$(CH_3)_2$, and $R^5$ and $R^6$ are independently selected from H and $C_{1-6}$alkyl;

In some embodiments of the present invention. A is selected from 5-6 membered heteroaryl and 4-9 membered heterocycloalkyl, said heteroaryl and heterocycloalkyl can be independently optionally substituted with $C_{1-6}$alkyl, —CN, —OH, —$NR^5R^6$, halogen. —O—$C_{1-6}$alkyl. —S—$C_{1-6}$alkyl, or —$SO_2$—$C_{1-6}$alkyl, said $C_{1-6}$alkyl can be optionally substituted with —OH, halogen, or —(CO)N$(CH_3)_2$, and $R^5$ and $R^6$ are independently selected from H and $C_{1-6}$alkyl;

In some embodiments of the present invention, compounds of the present invention are selected from:

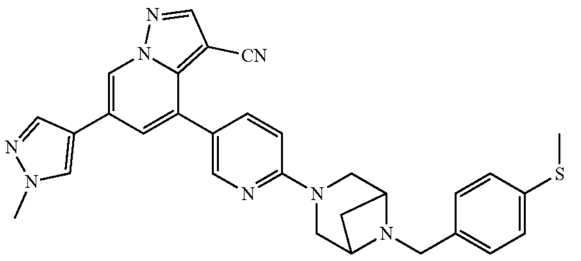

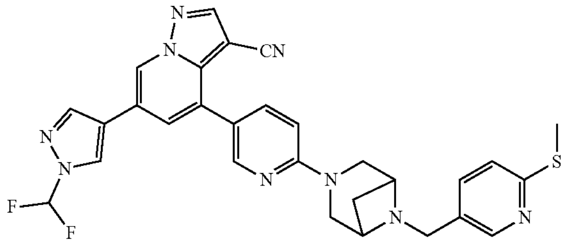

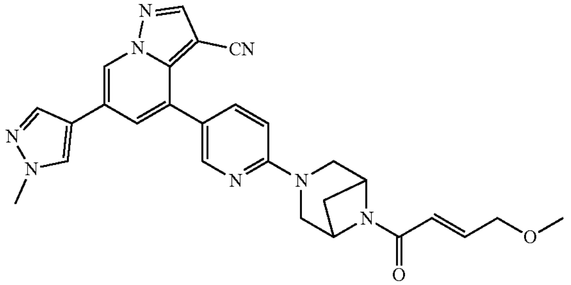

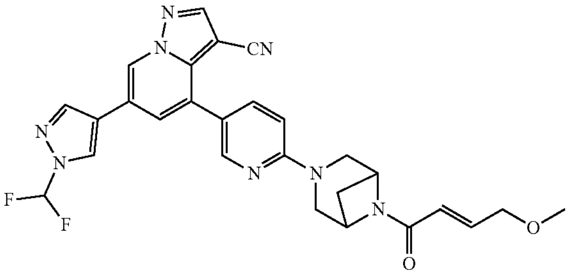

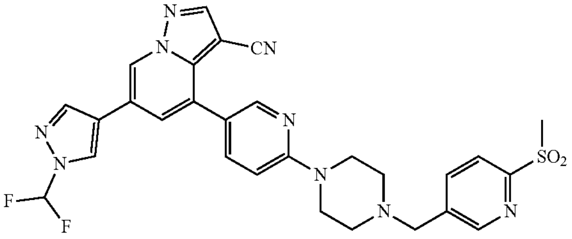

-continued
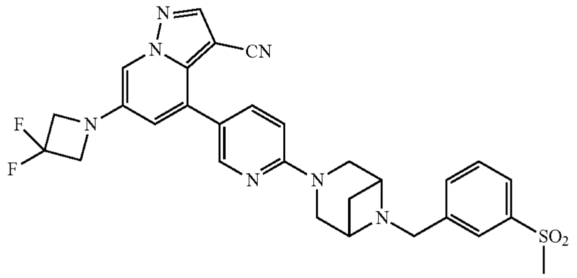
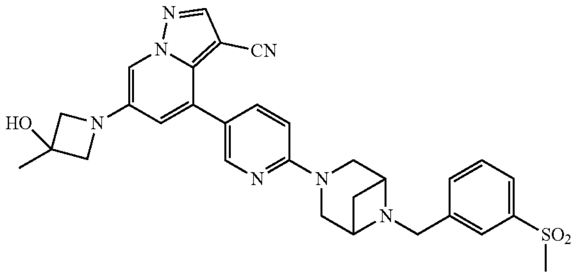
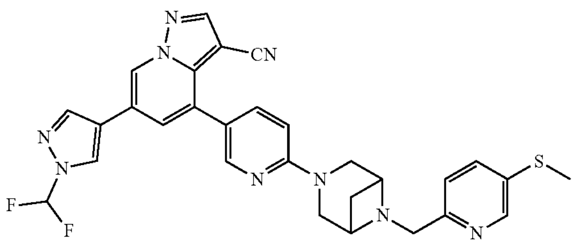
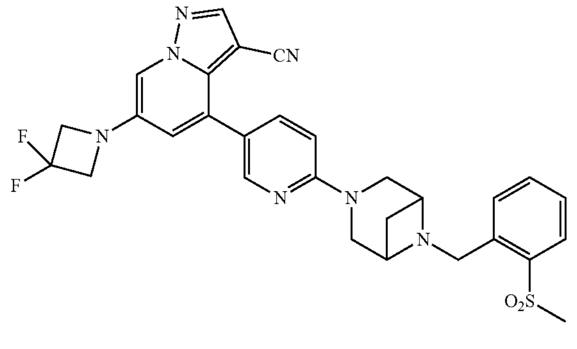
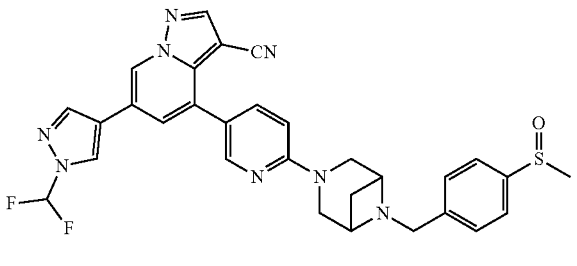
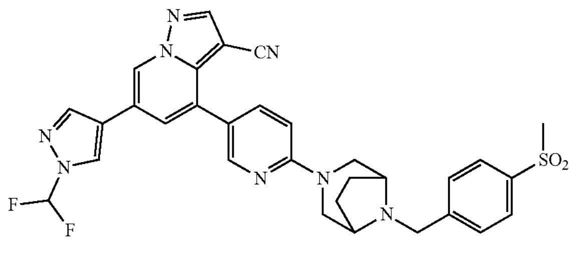
-continued
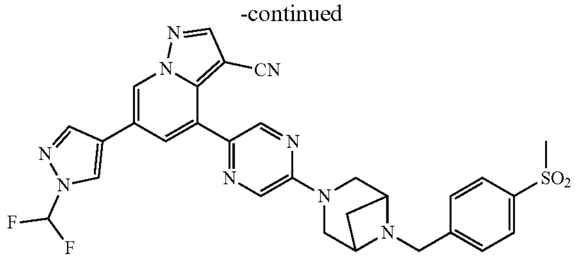
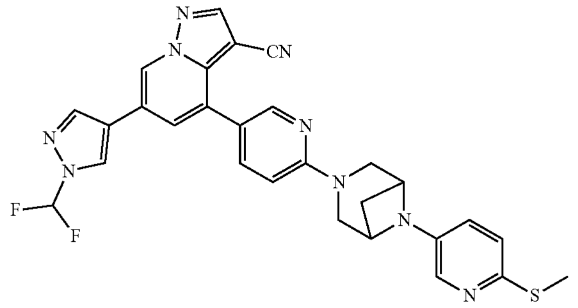
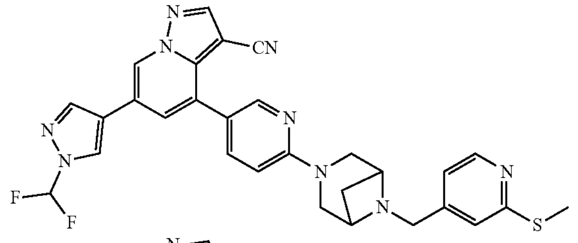
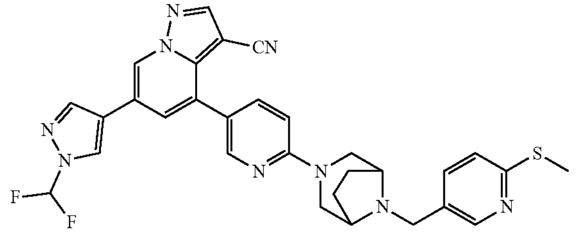
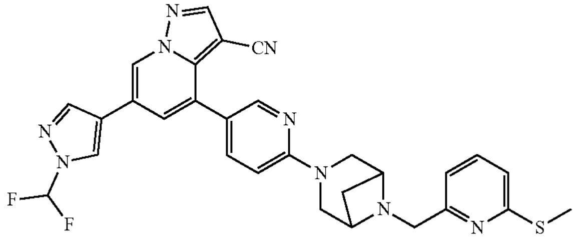
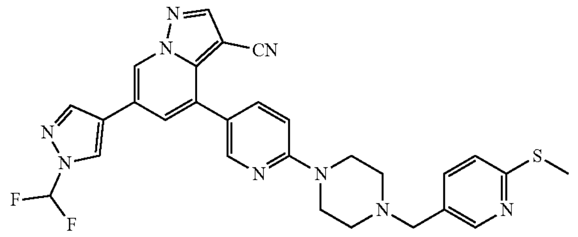
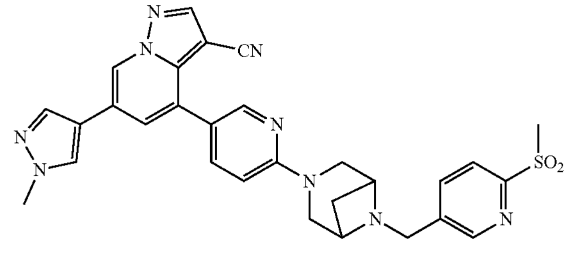

-continued
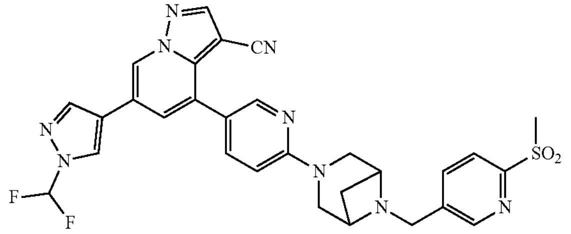
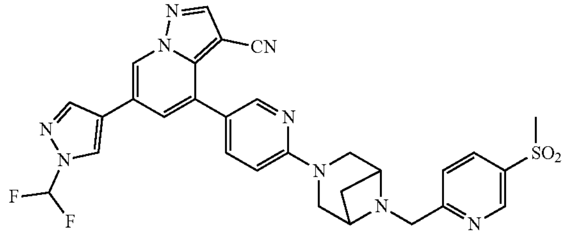
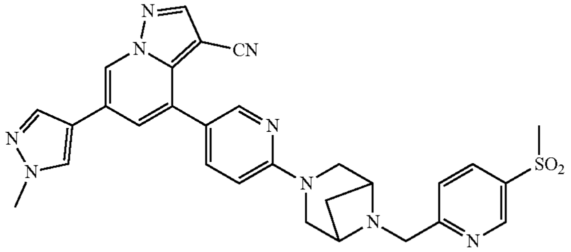
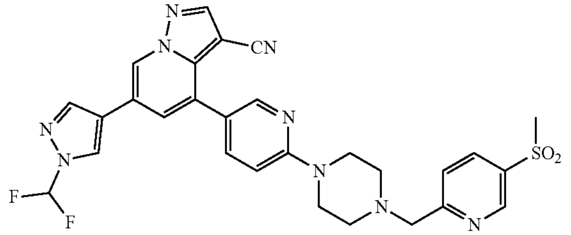
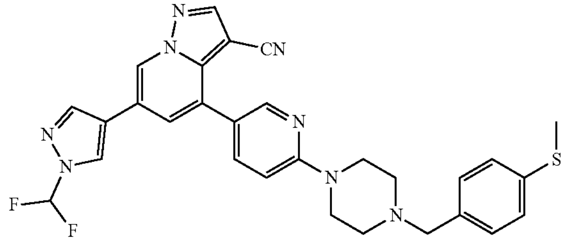
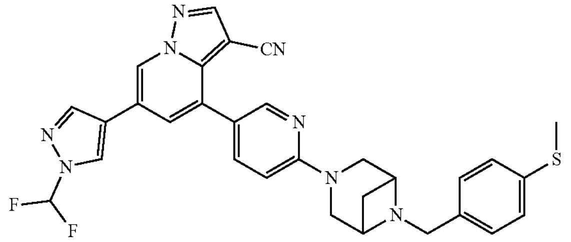
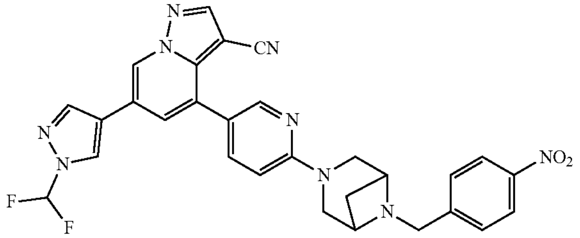
-continued
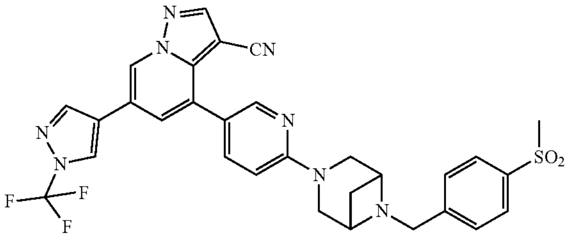
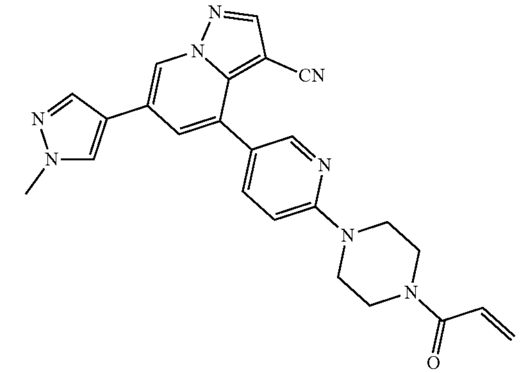
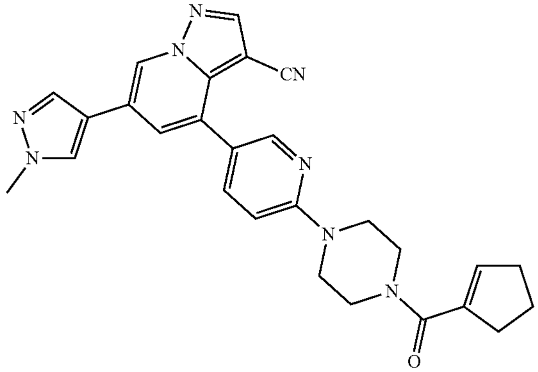
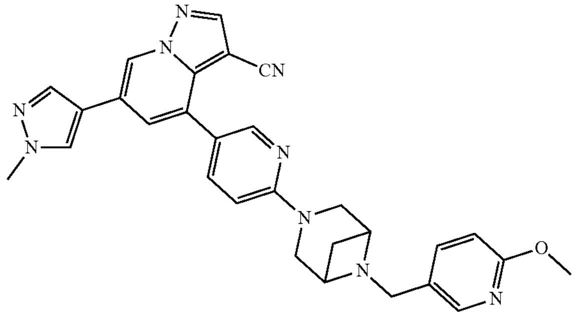
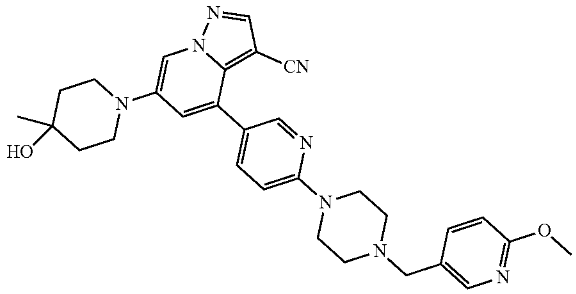

-continued
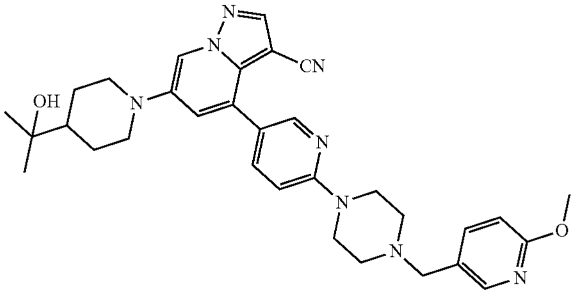
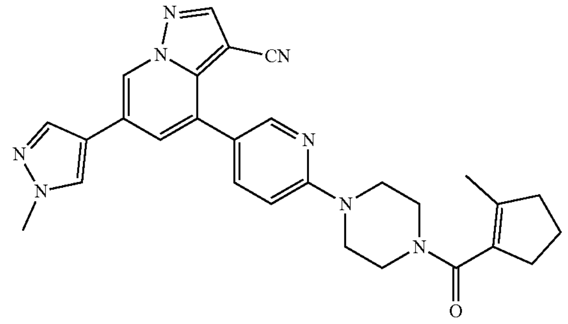
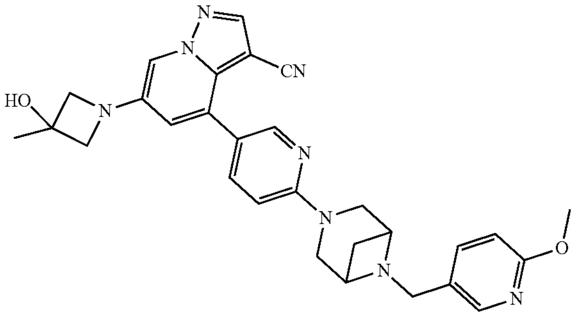
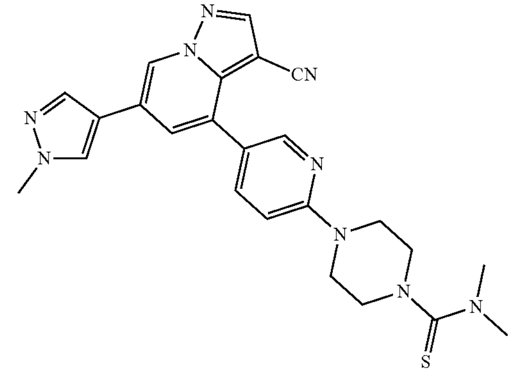
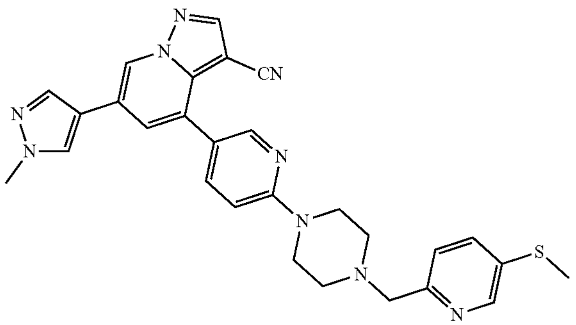
-continued
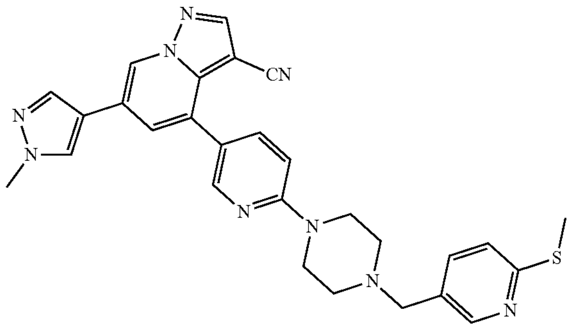
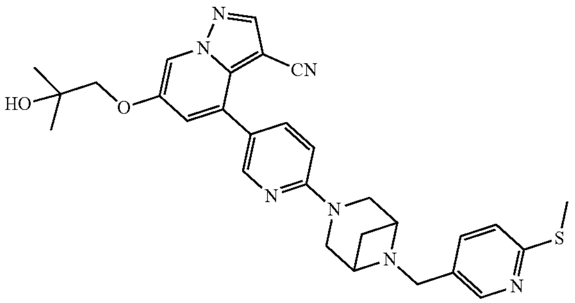
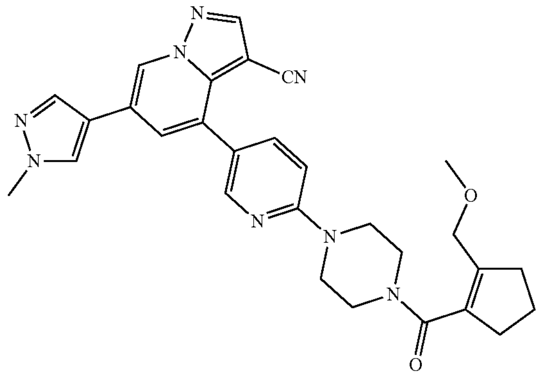
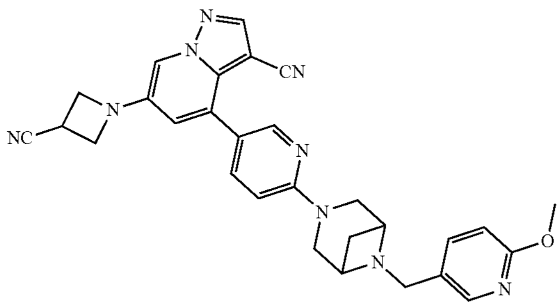
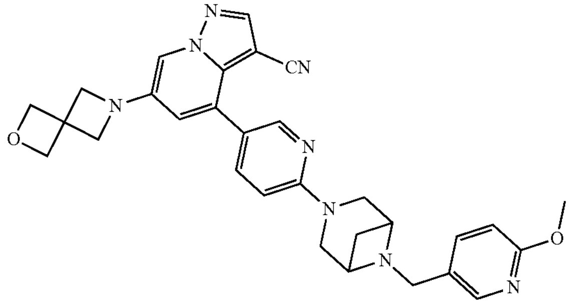

-continued
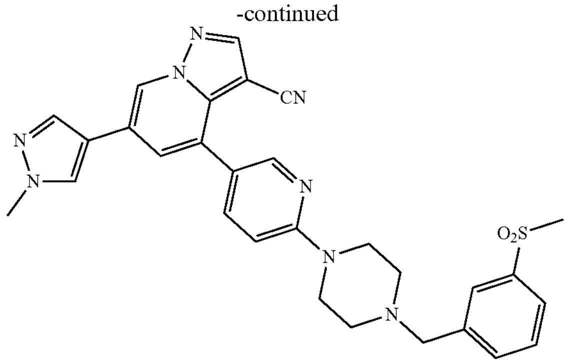
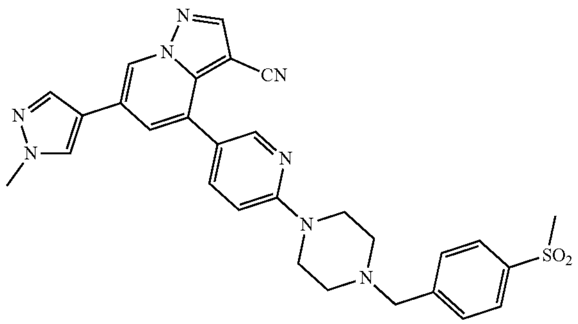
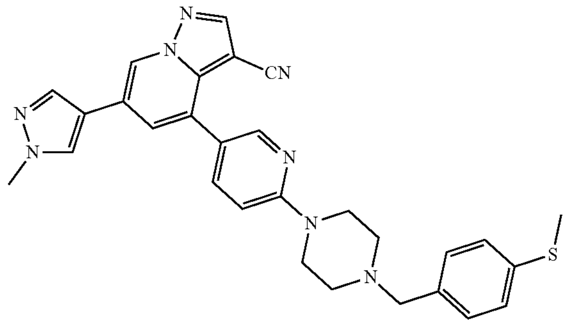
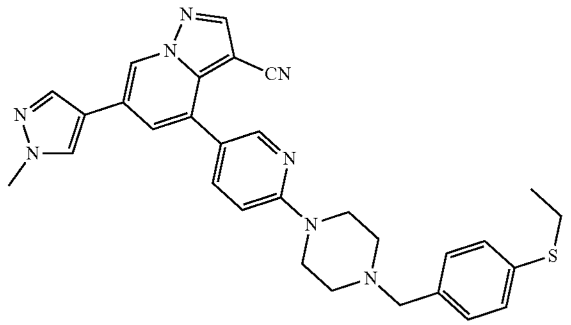
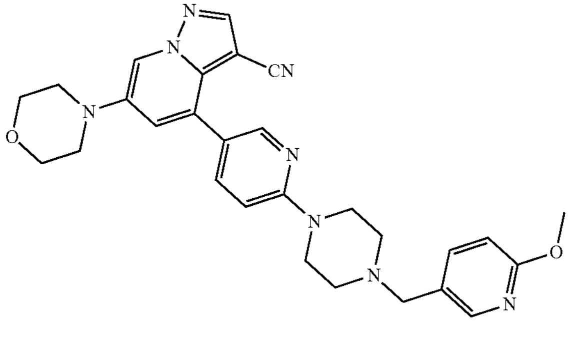
-continued
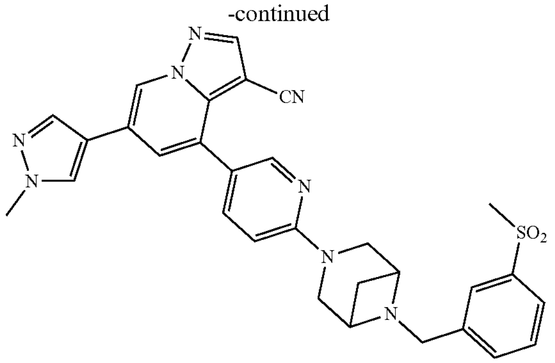
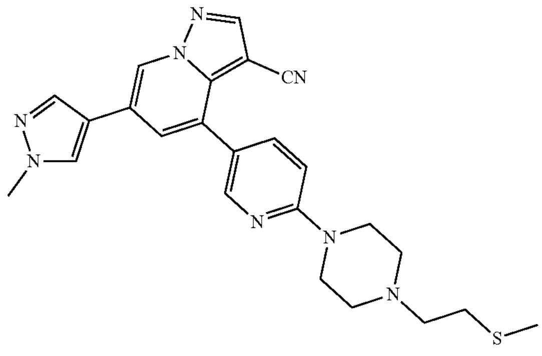
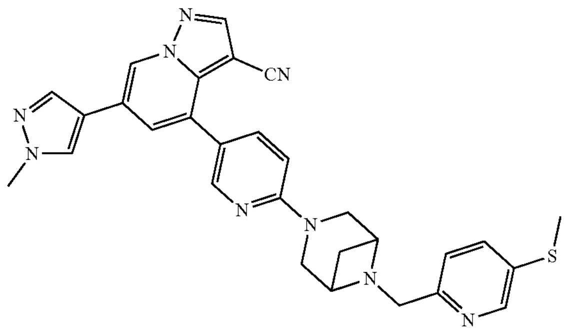
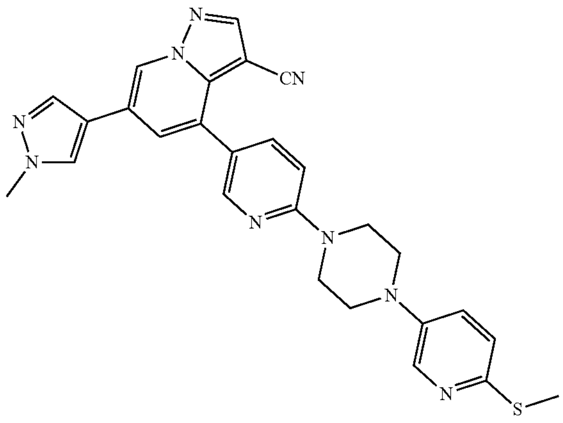

-continued
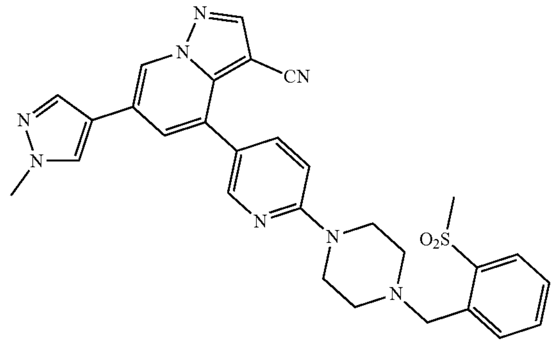
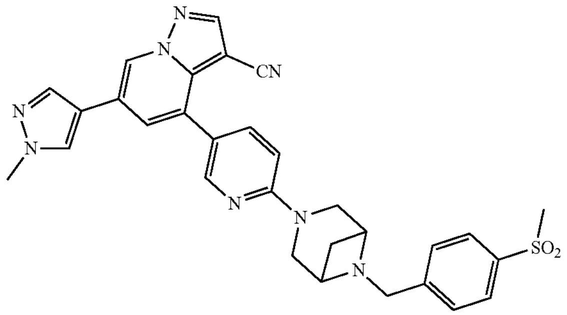
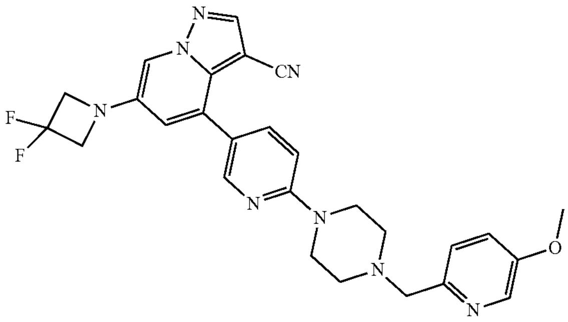
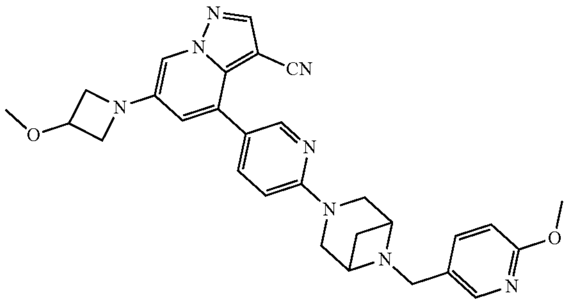
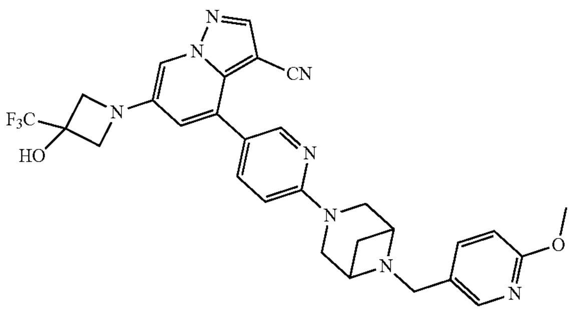
-continued
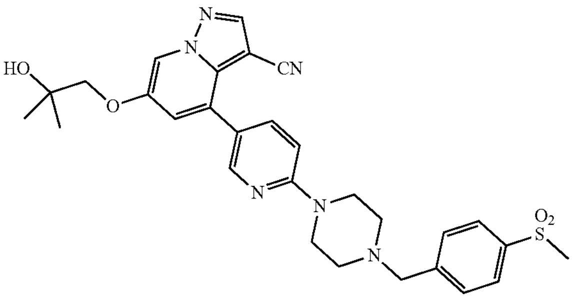
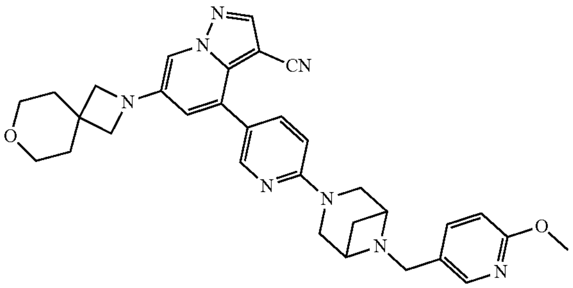
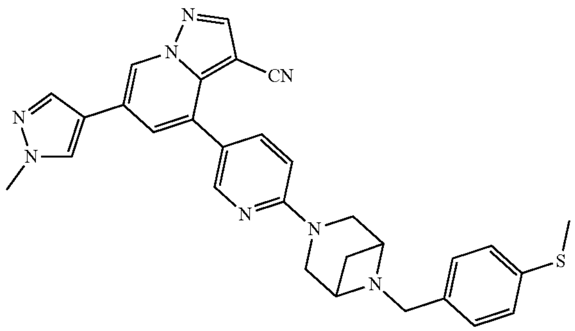
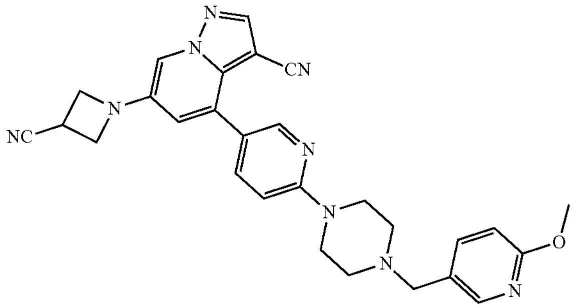
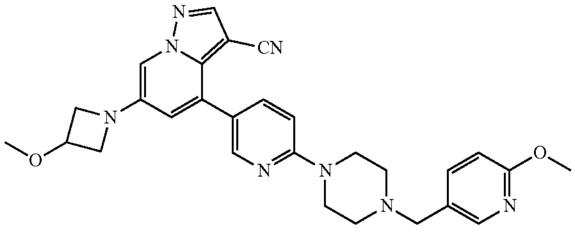
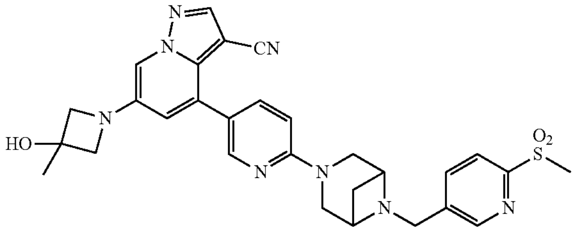

-continued
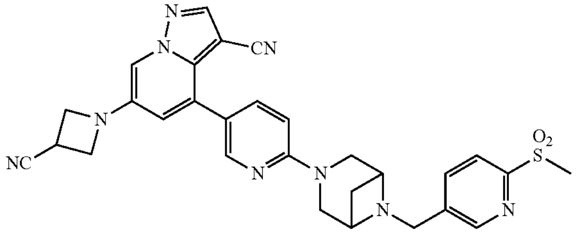
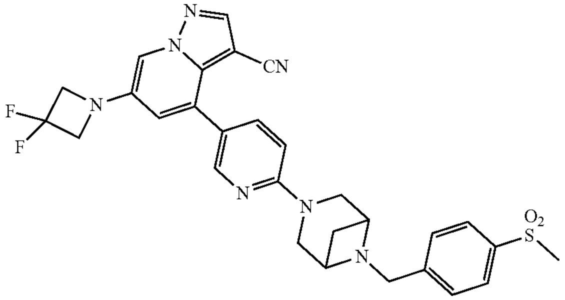
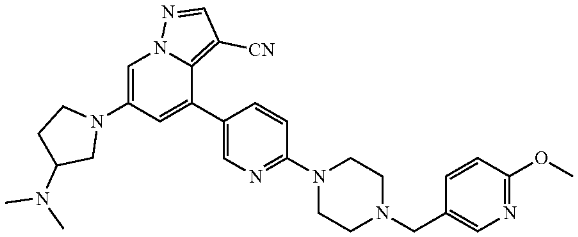
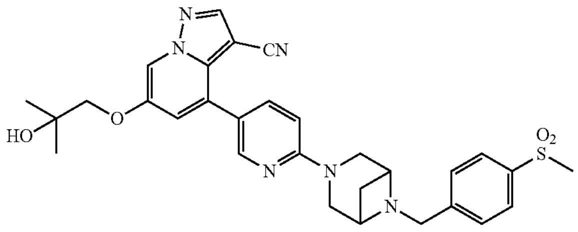
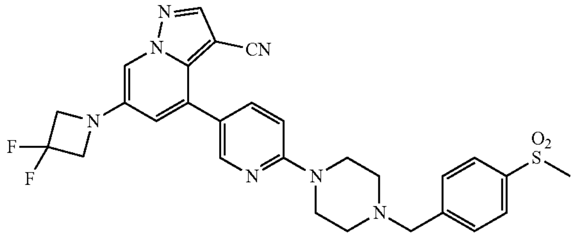
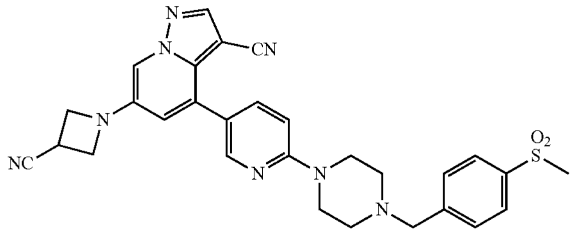
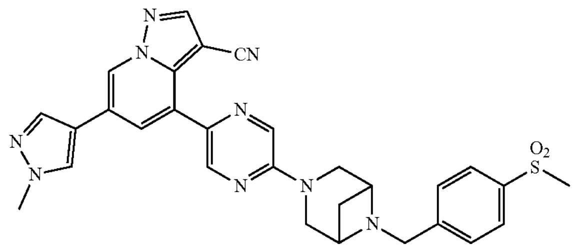
-continued
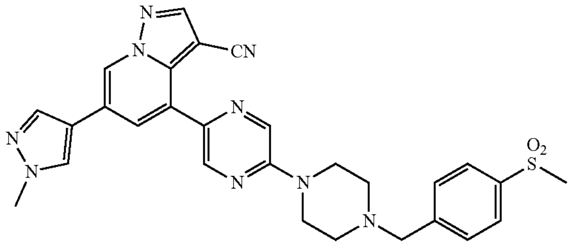
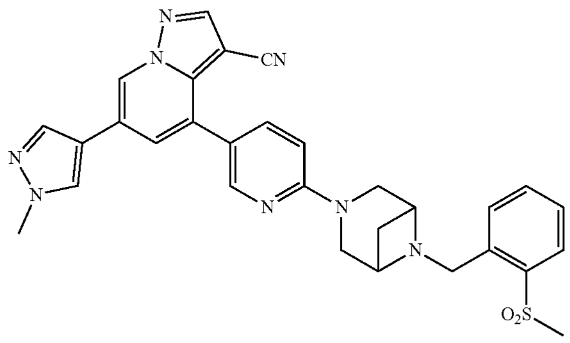
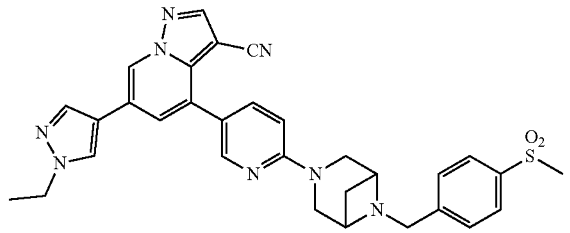
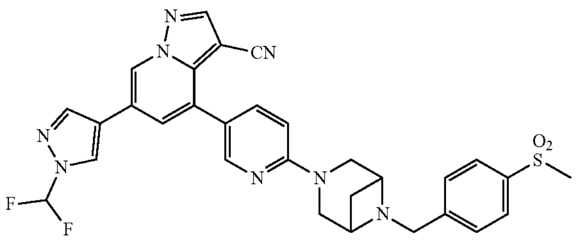
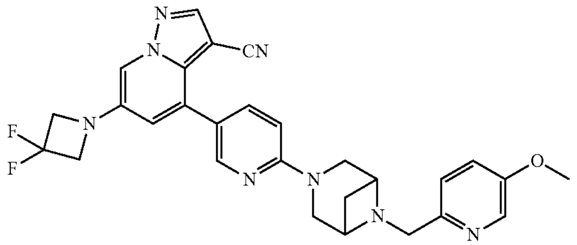
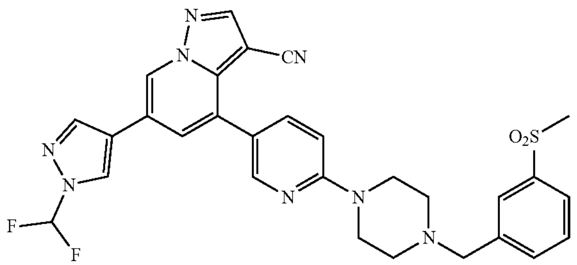

-continued

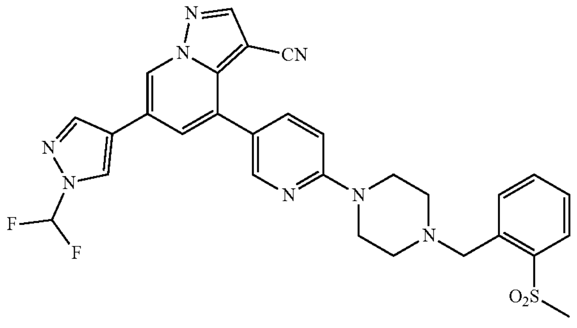

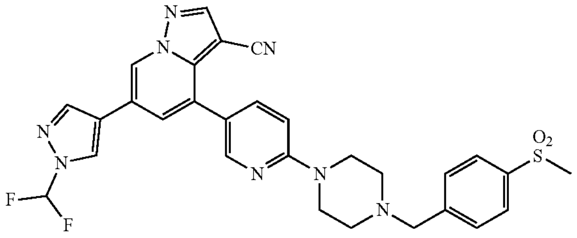

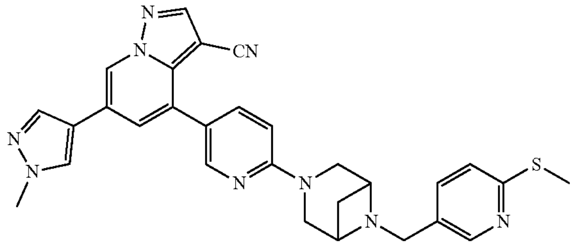

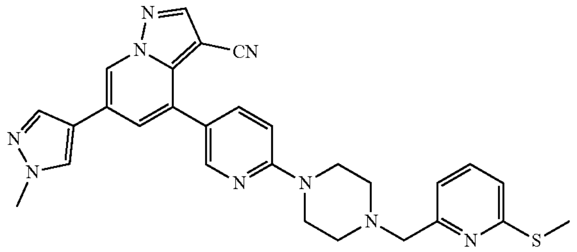

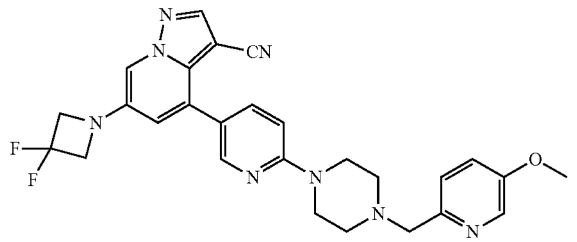

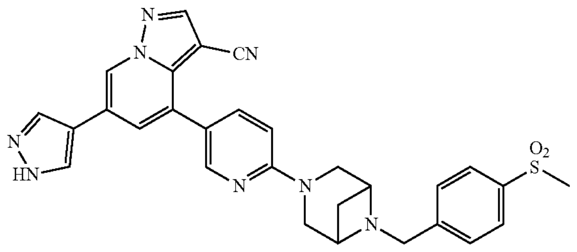

-continued

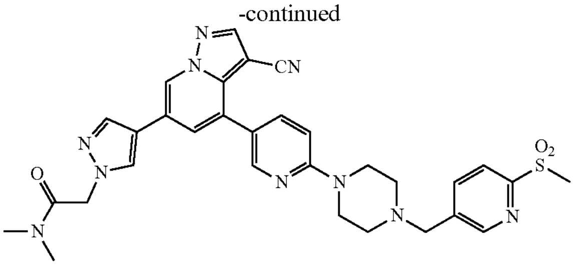

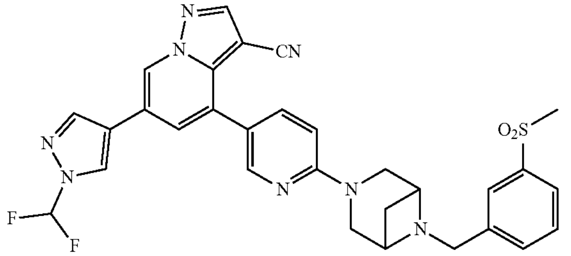

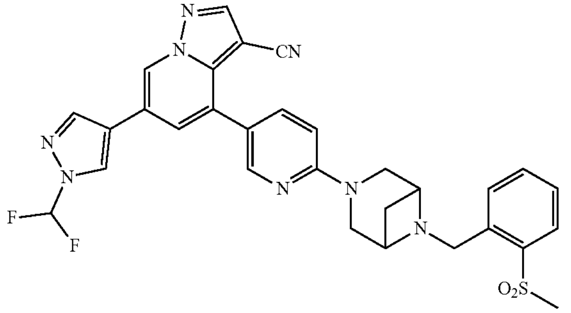

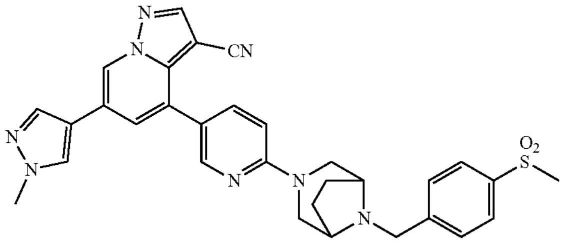

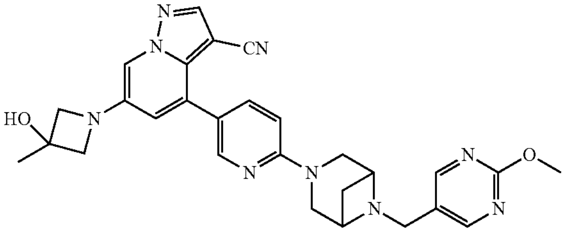

or a pharmaceutically acceptable salt, solvate, polymorph or tautomer thereof.

Another aspect of the present invention is related to a pharmaceutical composition comprising a compound of Formula (1) of the present invention, or a pharmaceutically acceptable salt, solvate, polymorph or tautomer thereof, and pharmaceutically acceptable carrier;

In another aspect, the present invention provides a method of treating RET-related diseases, the method comprising administering, to a subject an effective amount of a compound of Formula (1) or a pharmaceutically acceptable salt, solvate, polymorph or tautomer thereof, or a combination thereof; in some embodiments, the RET-related diseases include lung cancer, papillary thyroid carcinoma, medullary thyroid carcinoma, differentiated thyroid carcinoma, recurrent thyroid carcinoma, refractory differentiated thyroid carcinoma, multiple endocrine tumors of type 2A or 2B (MEN2A or MEN2B, respectively), pheochromocytoma, parathyroid hyperplasia, breast cancer, colorectal cancer, papillary renal cell carcinoma, gastrointestinal mucosal ganglionic cell tumor, and cervical cancer, preferably REF fusion lung cancer or medullary thyroid carcinoma, more preferably small cell lung cancer, non-small cell lung cancer, bronchiolar carcinoma, or lung adenocarcinoma.

In some embodiments of the present invention, the subject involved in the present invention is a mammal including humans.

In another aspect, the present invention provides a use of a compound of Formula (I), or a pharmaceutically acceptable salt, solvate, polymorph or tautomer thereof, in the manufacture of a medicament for the treatment of RET-related diseases; in some embodiments, the RET-related diseases include lung cancer, papillary thyroid carcinoma, medullary thyroid carcinoma, differentiated thyroid carcinoma, recurrent thyroid carcinoma, refractory differentiated thyroid carcinoma, multiple endocrine tumors of type 2A or 2B (MEN2A or MEN2B, respectively), pheochromocytoma, parathyroid hyperplasia, breast cancer, colorectal cancer, papillary renal cell carcinoma, gastrointestinal mucosal ganglionic cell tumor, or cervical cancer, preferably RET fusion lung cancer or medullary thyroid carcinoma, more preferably small cell lung cancer, non-small cell lung cancer, bronchiolar carcinoma or lung adenocarcinoma.

DETAILED DESCRIPTION OF THE INVENTION

Exemplary embodiments utilizing the principles of the present invention are set forth in the following detailed description. The features and advantages of the present invention may be better understood by reference to the following contents of the invention.

It is to be understood that the scope of the various aspects of the invention is determined by the claims, and that methods and structures within the scope of the claims, as well as equivalents thereof, are intended to be within the scope of the claims.

Unless defined otherwise, all technical and scientific terms used herein have the same meaning as commonly understood by one of ordinary skills in the art. All patents, patent applications, and published materials cited throughout this article are hereby incorporated by reference in their entirety, unless otherwise indicated.

It is to be understood that both the foregoing general description and the following detailed description are exemplary and explanatory and are not restrictive of any inventive subject matter. The use of the singular also includes the plural unless specifically stated otherwise. The use of "or" means "and/or" unless otherwise indicated. Furthermore, the use of the term "include" and other forms, such as "comprise". "have", and "contain", are nonrestrictive Some Chemical Terms The term "optional". "optional" or "optionally" means that the event or situation described later may or may not occur, and the description includes the occurrence of the event or situation and the non-occurrence of the event or situation. For example, "optionally substituted alkyl" means "unsubstituted alkyl" or "substituted alkyl". Also, an optionally substituted group may be unsubstituted (for example: $—CH_2CH_3$), completely substituted (for example: $—CF_2CF_3$), monosubstituted (for example: $—CH_2CH_2F$) or any level between mono- and completely substituted (e.g: $—CH_2CHF_2$, $—CF_2CH_3$. $—CFHCHF_2$, etc.). Those skilled in the art can understand that for any group containing one or more substituents, any substitution or substitution pattern that is impossible to exist in space and/or cannot be synthesized will not be introduced.

Unless otherwise indicated, conventional methods within the skill of the art are employed, such as mass spectrometry, nuclear magnetic resonance, high performance liquid chromatography, infrared and ultraviolet/visible spectroscopy, and pharmacological methods. Unless specifically defined otherwise, the relevant terms and experimental procedures and techniques in analytical chemistry, organic synthetic chemistry, and pharmaceutical and medicinal chemistry herein are known in the art. Standard techniques may be used in chemical synthesis, chemical analysis, pharmaceutical preparation, formulation and delivery, and treatment of patients. For example, reactions and purifications can be carried out using the manufacturer's instructions for the kit, or in a manner well known in the art or in accordance with the instructions of the present invention. The techniques and methods described above can generally be carried out in accordance with conventional methods well known in the art, in accordance with a number of general and more specific documents cited and discussed in this specification. In the present specification, groups and substituents thereof may be selected by those skilled in the art to provide stable moieties and compounds.

When a substituent is described by a conventional chemical formula written from left to right, the substituent also includes chemically equivalent substituents obtained when the structural formula is written from right to left. For example, $—CH_2O—$ is equivalent to $—OCH_2—$.

As used herein, the terms "group" and "chemical group" refer to a particular moiety or functional group of a molecule. Chemical groups are often considered as chemical entities embedded or attached to a molecule.

Some of the chemical groups named herein may use abbreviated notation to indicate the total number of carbon atoms. For example $C_1$-$C_6$ alkyl describes an alkyl group, as defined below, having a total of 1 to 6 carbon atoms. The total number of carbon atoms indicated in the abbreviated notation does not include the carbon atoms on the possible substituents.

The term "halogen", "halo" or "halide" refers to bromine, chlorine, fluorine or iodine.

As used herein, the terms "aroma", "aromatic ring". "aromatic". "aromaticity" and "aromatic ring" refer to a planar ring portion of one or more rings having a delocalized electron conjugation system containing 4n+2 electrons, where n is an integer. The aromatic ring may be formed from 5, 6, 7, 8, 9 or more atoms. The aromatic compound may be optionally substituted and may be monocyclic or fused polycyclic. The term aromatic compounds include all carbocyclic rings (e.g., benzene rings) and rings containing one or more heteroatoms (e.g., pyridine).

The term "heteroatom" or "hetero" as used herein alone or as part of another ingredient refers to an atom other than carbon and hydrogen. The heteroatoms are independently selected from oxygen, nitrogen, sulfur, phosphorus, silicon, selenium, and stannum, but are not limited to these atoms. In embodiments where two or more heteroatoms are present, the two or more heteroatoms may be the same as each other, or some or all of the two or more heteroatoms may be different from each other.

The terms "fused" or "fused ring" as used herein, alone or in combination, refer to a cyclic structure in which two or more rings share one or more bonds.

The terms "spiro" or "spirocyclic" as used herein, alone or in combination, refer to a cyclic structure in which two or more rings share one or more atoms.

The term "alkyl" as used herein alone or as part of other components (such as monoalkylamino) refers to an optionally substituted linear or optionally substituted branched monovalent saturated hydrocarbon having 1 to 12 carbon atoms, preferably 1 to 8 carbon atoms, more preferably 1 to 6 carbon atoms, attached to the rest of the molecule via a single bond, for example methyl, ethyl, n-propyl, isopropyl, n-butyl, isobutyl, sec-butyl, tert-butyl, n-pentyl, n-hexyl, n-heptyl. 2-methylhexyl, 3-methylhexyl, n-octyl, n-nonyl, n-decyl and the like.

The term "cycloalkyl" as used herein alone or as part of another component refers to a stable monovalent non-aromatic monocyclic or polycyclic hydrocarbon group containing only carbon and hydrogen atoms, possibly including fused, spiro or bridged ring systems, containing from 3 to 15 ring-forming carbon atoms, preferably from 3 to 10 ring-forming carbon atoms, more preferably from 3 to 8 ring-forming carbon atoms, which may be saturated or unsaturated, attached to the rest of the molecule via a single bond. Non-limiting examples of "cycloalkyl" include, but are not limited to, cyclopropyl, cyclobutyl, cyclopentyl, cyclohexyl, cycloheptyl, and the like.

The term "heteroaryl" refers to a monocyclic or fused ring of 5 to 12 ring atoms having 5, 6, 7, 8, 9, 10, 11 or 12 ring atoms containing 1, 2, 3 or 4 ring atoms selected from N, O, S, the remaining ring atoms being C, and having a fully conjugated π-electron system. Heteroaryl groups may be unsubstituted or substituted and include, but are not limited to, alkyl, alkyloxy, aryl, aminyl, amino, halogen, hydroxy, cyano, nitro, carbonyl, and heteroalicyclic groups. Non-limiting examples of unsubstituted heteroaryl groups include, but are not limited to, pyrrolyl, furanyl, thienyl, imidazolyl, oxazolyl, pyrazolyl, pyridinyl, pyrimidinyl, pyrazinyl, quinolinyl, isoquinolinyl, tetrazolyl, and triazinyl.

The terms "heterocyclyl". "heterocycloalkyl". "heterocycle" as used herein alone or as part of another component, refer to a stable 3-18 membered monovalent non-aromatic ring containing from 2 to 12 carbon atoms and from 1 to 6 heteroatoms selected from nitrogen, oxygen and sulfur. Unless otherwise specified, a heterocyclyl group may be a monocyclic, bicyclic, tricyclic or tetracyclic ring system, which may contain fused, spiro or bridged ring systems, nitrogen, carbon or sulfur on the heterocyclyl may be optionally oxidized, the nitrogen atom may be optionally quaternized, and the heterocyclyl may be partially or completely saturated. The heterocyclyl may be attached to the rest of the molecule via a single bond through a carbon atom or heteroatom on the ring. A heterocyclyl containing fused rings may contain one or more aromatic or heteroaromatic rings as long as the atoms on the non-aromatic ring are attached to the rest of the molecule. For purposes of this application, the heterocyclyl is preferably a stable 4-11 membered monovalent non-aromatic monocyclic or bicyclic ring containing from 1 to 3 heteroatoms selected from nitrogen, oxygen and sulfur, more preferably a stable 4-8 membered monovalent non-aromatic monocyclic ring containing from 1 to 3 heteroatoms selected from nitrogen, oxygen and sulfur. Non-limiting examples of heterocyclyl include azepanyl, azetidinyl, decahydroisoquinolinyl, dihydrofuranyl, indolinyl, dioxolanyl. 1,1-dioxo-thiomorpholinyl, imidazolidinyl, imidazolinyl, isothiazolidinyl, isoxazolidinyl, morpholinyl, octahydroindolyl, octahydroisoindolyl, oxazinyl, piperazinyl, piperidinyl. 4-piperidonyl, pyranyl, pyrazolidinyl, pyrrolidinyl, quinolizinyl, quinuclidinyl, tetrahydrofuranyl, tetrahydropyranyl, and the like.

As used herein, the term "polymorph" or "polymorphy" refers to a compound of the present invention having a variety of lattice morphologies. Some of the compounds of the present invention may have more than one crystal form, and the present invention encompasses all polymorphs or mixtures thereof.

Intermediate compounds of the compounds of the present invention and polymorphs thereof are also within the scope of the present invention.

Unless otherwise specified, olefinic double bond contained in the compound of the present invention includes E and Z isomers.

It is to be understood that the compounds of the present invention may contain asymmetric centers. These asymmetric centers may independently be in the R or S configuration. Some of the compounds of the present invention may also show cis-trans isomerism, which is obvious to those skilled in the art. It is to be understood that the compounds of the present invention include individual geometric and stereoisomers thereof as well as mixtures thereof, including racemic mixtures. These isomers may be separated from their mixtures by practicing or modifying known methods, such as chromatographic techniques and recrystallization techniques, or they may be prepared separately from the appropriate isomers of their intermediates.

As used herein, the term "pharmaceutically acceptable salt" includes both acid and base addition salts.

"Pharmaceutically acceptable acid addition salts" refers to those salts formed with inorganic acids such as, but not limited to, hydrochloric acid, hydrobromic acid, sulfuric acid, nitric acid, and phosphoric acid; or with organic acids such as, but not limited to, acetic acid, 2,2-dichloroacetic acid, adipic acid, alginic acid, ascorbic acid, aspartic acid, benzenesulfonic, benzoic acid, capric acid caproic acid, carbonic acid, cinnamic acid, and citric acids, which retain the biological effectiveness and properties of the free base of the compound, and are not biologically or otherwise undesirable. "Pharmaceutically acceptable base addition salts" refers to those salts that retain the biological effectiveness and properties of the free acids of the compounds and are not biologically or otherwise undesirable. These salts are prepared by reacting free acids with an inorganic or organic bases. Salts formed by reaction with inorganic bases include, but are not limited to, sodium, potassium, lithium, ammonium, calcium, magnesium, iron, zinc, copper, manganese, aluminum salts and the like. Preferred inorganic salts are ammonium, sodium, potassium, calcium, and manganese salts.

Organic bases that form salts include, but are not limited to, primary, secondary, tertiary, and cyclic amines, such as ammonia, isopropylamine, trimethylamine, diethylamine, triethylamine, tripropylamine, ethanolamine, diethanolamine, ethanolamine, dicyclohexylamine, ethylenediamine, purine, piperazine, piperidine, choline, and caffeine. Particularly preferred organic bases include isopropylamine, diethylamine, ethanolamine, trimethylamine, dicyclohexylamine, choline, and caffeine.

Crystallization often produces solvates of the compounds of the invention. The term "solvate" as used herein refers to a complex composed of one or more molecules of the compound of the present invention and one or more solvent molecules.

The solvent may be water, in which case the solvate is a hydrate. It may additionally be an organic solvent. Thus, the compounds of the present invention may exist as hydrates, including monohydrate, dihydrate, hemihydrate, trihydrate, and tetrahydrate, as well as the corresponding solvated forms. The compounds of the present invention may be true solvates, but in other cases, the compounds of the present invention may simply accidentally retain water or a mixture of water with some other solvent. The compounds of the present invention may be reacted in a solvent or precipitated or crystallized in a solvent.

Solvates of the compounds of the present invention are also included in the scope of the present invention.

The term "pharmaceutical composition" as used herein refers to a formulation incorporating a compound of the present invention and a medium generally accepted in the art for delivering a biologically active compound to a mammal, such as a human. Such media comprise all pharmaceutically acceptable carriers.

The term "acceptable" as used herein in connection with a formulation, composition or ingredient means there is no sustained deleterious effect on the overall health of the subject being treated.

The term "pharmaceutically acceptable" as used herein refers to a substance (e.g., a carrier or diluent) that does not affect the biological activity or properties of the compounds of the present invention, and is relatively nontoxic, i.e., the substance can be administered to an individual without causing an undesirable biological response or interaction in an undesirable manner with any of the components contained in the composition.

"Pharmaceutically acceptable carrier" includes, but is not limited to, adjuvants, carriers, excipients, auxiliaries, deodorants, diluents, preservatives, dyes/colorants, flavor enhancers, surfactants and wetting agents, dispersing agents, suspending agents, stabilizers, isotonic agents, solvents, or emulsifying agents, which may be used in humans and domesticated animals, as approved by the relevant government administration.

As used herein, the terms "subject", "patient, "object", or "individual" refer to an individual suffering from a disease, disorder, or condition, etc., including mammals and non-mammals. Examples of mammals include, but are not limited to, any member of the class mammalia: humans, non-human primates (e.g., chimpanzees and other apes and monkeys); livestock, such as cattle, horses, sheep, goats, pigs; domestic animals such as rabbits, dogs, and cats; laboratory animals, including rodents, such as rats, mice and guinea pigs, etc. Non-mammals include, but are not limited to, birds, and fish. In an embodiment related to methods and compositions provided herein, the mammal is a human.

The term "treatment" as used herein refers to the treatment of a disease or condition associated with a mammal, particularly a human, including (i) preventing a mammal, particularly a mammal that has previously been exposed to a disease or condition but has not yet been diagnosed with the disease or condition, from developing the corresponding disease or condition;

(ii) inhibiting the disease or disorder, i.e., controlling its development;

(iii) alleviating the disease or disorder. i.e., causing regression of the disease or disorder, and (iv) alleviating symptoms caused by the disease or disorder.

The terms "disease" and "condition" as used herein may be used interchangeably and may have different meanings, as some specific diseases or conditions have no known pathogenic factors (so the cause of the disease remains unknown), and therefore they cannot be considered a disease but can only be considered an unwanted condition or syndrome, with more or less specific symptoms having been confirmed by clinical researchers.

As used herein, the terms "effective amount", "therapeutically effective amount", or "pharmaceutically effective amount" refer to an amount of at least one agent or compound that, upon administration, is sufficient to relieve to some extent one or more symptoms of the disease or disorder being treated. The result may be reduction and/or alleviation of signs, symptoms or causes, or any other desired change in the biological system. For example, an "effective amount" for therapy is the amount of a composition comprising a compound disclosed herein required to provide a clinically significant disease remission effect.

Effective amounts suitable for use in any individual case may be determined using techniques such as dose escalation test.

The terms "taking", "administration". "administering", etc., as used herein, refer to a method of delivering a compound or composition to a desired site for biological action. These methods include, but are not limited to, oral routes, duodenal routes, parenteral injection (including intravenous, subcutaneous, intraperitoneal, intramuscular, intraarterial injection or infusion), topical administration, and rectal administration. In preferred embodiments, the compounds and compositions discussed herein are administered orally.

Preparation of Compound of the Invention

The following reaction schemes show methods for preparing the compounds of the present application.

It is to be understood that in the following description, combinations of substituents and/or variables of the formula are permissible only if stable compounds are formed.

It will also be appreciated by those skilled in the art that in the schemes described below, functional groups of Intermediate compounds may need to be protected by suitable protecting groups. These functional groups include hydroxyl, amino, sulfhydryl, and carboxyl groups. Suitable hydroxy protecting groups include trialkylsilyl or diarylalkylsilyl (e.g., tert-butylmethylsilyl, tert-butyldiphenylsilyl or trimethylsilyl), tetrahydropyranyl, benzyl, etc. Suitable amino, amidino, and guanidine protecting groups include tert-butoxycarbonyl, benzyloxycarbonyl, etc. Suitable sulfhydryl protecting groups include —C(O)—R"(R" represents alkyl, aryl or arylalkyl), p-methoxybenzyl, trityl, etc. Suitable carboxy protecting groups include alkyl, aryl or arylalkyl esters. The protecting groups may be added or removed by standard techniques known to those skilled in the an.

EXAMPLE

The following non-limiting examples are merely illustrative and do not limit the invention in any way.

Unless otherwise stated, temperatures are in degrees Celsius. Reagents were purchased from commercial suppliers such as Sinopharm Chemical Reagent Beijing Co., Ltd., Alfa Aesar. or Beijing J&K Scientific Ltd., and these reagents were used without further purification unless otherwise specified.

Unless otherwise stated, the following reactions were carried out at room temperature, in an anhydrous solvent, under positive pressure of nitrogen or argon, or using a drying tube; the reaction bottle was provided with a rubber diaphragm so as to add a substrate and a reagent through a syringe; glassware was baked and/or dried by drying.

Unless otherwise stated, silica gel for column chromatography was supplied from Qingdao Haiyang Chemical Plant in 200-300 mesh size; thin layer chromatography silica gel precast slab (HSGF254) for preparative Thin Layer Chromatography was produced by Yantai Chemical Industry Research Institute; Thermo LCQ Fleet type (ESI) Liquid Chromatograph Mass Spectrometer was used for MS assay; SGW-3 Automtic Polarimeter from Shanghai Shenguang Instrument and Meter Co., Ltd. was used for polarimetry.

Nuclear magnetic data ($^1H$ NMR) were run at 400 MHz using a Varian apparatus. The solvents used for nuclear magnetic data are $CDCl_3$, $CD_3OD$, $D_2O$, DMSO-d6, etc., based on tetramethylsilane (0.00 ppm) or based on residual solvent ($CDCl_3$: 7.26 ppm; $CD_3OD$: 3.31 ppm; $D_2O$: 4.79 ppm; d6-DMSO: 2. 50 ppm). When peak shape diversity is indicated, the following abbreviations denote different peak shapes: s (singlet), d (doublet), t (triplet), q (quartet), m (multiplet), br (broad), dd (doublet of doublets), dt (doublet of triplets). If a coupling constant is given, it is in Hertz (Hz), Abbreviation:

| | |
|---|---|
| $Pd_2(dba)_3$ | tris(dibenzylideneacetone)dipalladium |
| (±)BINAP | (±)-2, 2'-Bis(diphenylphosphino)-1, 1'-binaphthalene |
| $Pd(dppf)Cl_2$ | [1, 1'-bis(diphenylphosphino)ferrocene] dichloropalladium(II) |
| TEA | triethylamine |
| TFA | Trifluoroacetic acid |
| $NaBH(OAc)_3$ | sodium triacetoxyborohydride |
| DMSO | dimethyl sulfoxide |
| KOAc | potassium acetate |
| Toluene | toluene |
| $K_2CO_3$ | potassium carbonate |
| $Pd(PPh_3)_4$ | tetrakis(triphenylphosphine)palladium |
| $Cs_2CO_3$ | cesium carbonate |

Intermediate 1: Synthesis of 6-(1-methyl-1H-pyrazol-4-yl)-4-(6-(piperazin-1-yl) pyridin-3-yl) pyrazolo[1,5-a]pyridine-3-carbonitrile (Synthesized According to the Method Described in Patent WO2017/11776)

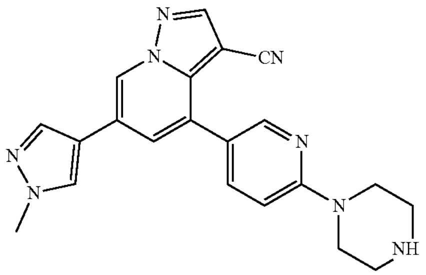 [SMILES: Cn1cc(-c2cc(-c3ccc(N4CCNCC4)nc3)c3c(C#N)cnn3c2)cn1]

Intermediate 2: Synthesis of 4-(6-(3,6-diazabicyclo[3.1.1]heptan-3-yl) pyridin-3-yl)-6-(1-methyl-1Hpyrazol-4-yl)pyrazolo[1,5-a]pyridine-3-carbonitrile (Synthesized According to the Method Described in Patent WO2017/11776)

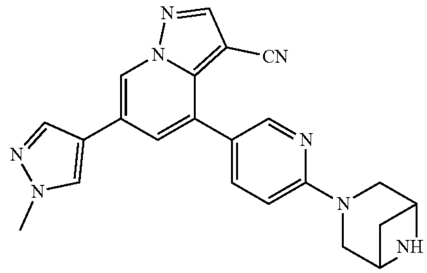 [SMILES: Cn1cc(-c2cc(-c3ccc(N4CC5CC(C4)N5)nc3)c3c(C#N)cnn3c2)cn1]

Intermediate 3: Synthesis of 6-(1-methyl-1Hpyrazol-4-yl)-4-(5-(piperazin- 1-yl) pyrazin-2-yl)pyrazolo[1,5-a]pyridine-3-carbonitrile (Synthesized According to the Method Described in Patent WO2017/11776)

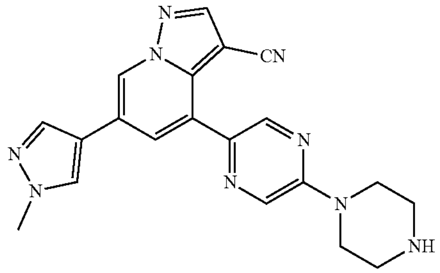 [SMILES: Cn1cc(-c2cc(-c3cnc(N4CCNCC4)cn3)c3c(C#N)cnn3c2)cn1]

Intermediate 4: Synthesis of 4-(5-(3,6-diazabicyclo[3.1.]heptan-3-yl) pyrazin-2-yl)-6-(1-methyl-1Hpyrazol-4-yl)pyrazolo[1,5-a]pyridine-3-carbonitrile

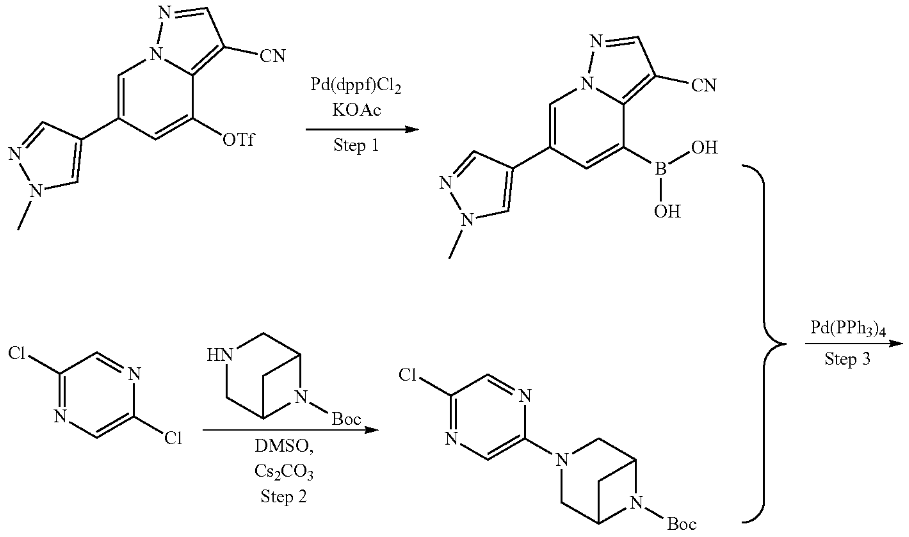

-continued

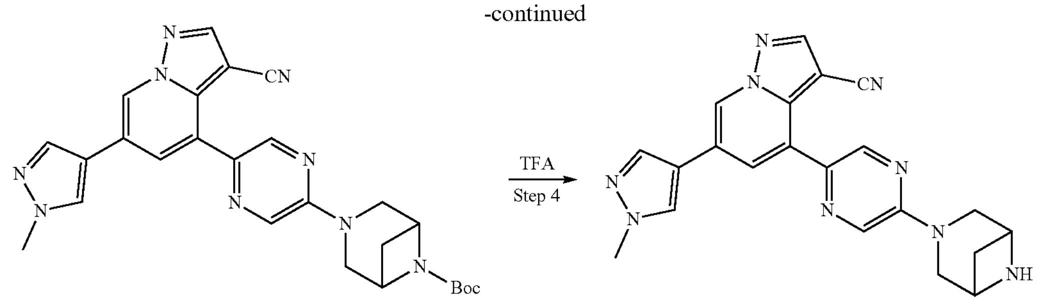

Step 1: (3-cyano-6-(1-methyl-1Hpyrazol-4-yl)pyrazolo[1,5-a]pyridine-4-yl)boronic acid Under protection of nitrogen, 3-cyano-6-(1-methyl-1Hpyrazol-4-yl)pyrazolo[1,5-a]pyridine-4-yl trifluoromethanesulfonate (371 mg) (synthesized according to patent WO2017/11776), bis(pinacolato)diboron (508 mg). [1,1'-bis (diphenylphosphino) ferrocene] dichloropalladium(II) (73 mg) and potassium acetate (196 mg) were added to dry dioxane (30 mL), the mixture was heated to 90° C. and stirred overnight, cooled to room temperature and filtered, the filter cake was cooled to room temperature and filtered, the filter cake was washed with dichloromethane, and the filtrate was evaporated under reduced pressure to dryness to obtain 3-cyano-6-(1-methyl-1Hpyrazol-4-yl) pyrazolo[1,5-a]pyridine-4-ylboronic acid as a crude product (300 mg), which was used directly in the next step.

Step 2: tert-butyl 3-(5-chloropyrazin-2-yl)-3,6-diazabicyclo[3.1.1] heptan-6-carboxylate At room temperature, to a solution of 2,5-dichloro pyrazine (149 mg) and tert-butyl 3,6-diazabicyclo[3.1.1]heptan-6-carboxylate (198 mg) in DMSO (10 mL) was added cesium carbonate powder (653 mg), and the mixture was heated to 85° C. and stirred for 4 hours. The reaction solution was cooled, poured into 50 mL water, and extracted with ethyl acetate; the extract was washed twice with brine, dried over anhydrous sodium sulphate and filtered, the filtrate was concentrated under reduced pressure, and the residue was purified through silica gel chromatography (eluent: petroleum ether:ethyl acetate=3:1 (V:V)) to obtain the title compound (250 mg).

Step 3: tert-butyl 3-(5-(3-cyano-6-(1-methyl-1Hpyrazol-4-yl)pyrazolo[1,5-a]pyridine-4-yl) pyrazin-2-yl)-3,6-diazabicyclo[3.1.1]heptan-6-carboxylate Under protection of nitrogen, 3-cyano-6-(n-methyl-1Hpyrazol-4-yl)pyrazolo[1,5-a] pyridine-4-yl boronic acid (300 mg) of step 1 and tert-butyl 3-(5-chloropyrazin-2-yl)-3,6-diazabicyclo[3.1.1]heptan-6-carboxy late (250 mg) of step 2 were dissolved in a mixed solvent of dioxane and water (5:1) (50 mL), and to the mixture were sequentially added tetrakis(triphenylphosphine)palladium (110 mg) and anhydrous potassium carbonate powder (278 mg). Then, the mixture was heated to 85° C. and stirred for 2 hours. The reaction solution was cooled, poured into water (150 mL), and extracted with dichloromethane, the extract was washed with brine, dried over anhydrous sodium sulphate and filtered, the filtrate was concentrated under reduced pressure, and the residue was purified through silica gel chromatography (eluent: petroleum ether:ethyl acetate=3:1 (V:V)) to obtain the title compound (200 mg).

Step 4: 4-(5-(3,6-diazabicyclo[3.1.1]heptan-3-yl) pyrazin-2-yl)-6-(1-methyl-1H pyrazol-4-yl) pyrazolo[1,5-a]pyridine-3-carbonitrile At 0° C. to a solution of tert-butyl 3-(5-(3-cyano-6-(1-methyl-1Hpyrazol-4-yl) pyrazolo[1,5-a]pyridine-4-yl) pyrazin-2-yl)-3,6-diazabicyclo [3.1.1]heptan-6-carboxylate obtained in step 3 (200 mg) in dichloromethane (20 mL) was slowly dropwise added trifluoroacetic acid (4 mL), after the dropwise addition was completed, the mixture was let warm up to room temperature and stirred for 1 hour. The reaction solution was concentrated, an aqueous solution of saturated sodium bicarbonate was added to adjust pH to weak basic, the solid thus formed was filtered and dried to obtain the title compound (140 mg).

Intermediate 5: Synthesis of 3-cyano-4-(6-(6-((6-methoxypyridin-3-yl) methyl)-3,6-diazabicyclo [3.1.1]heptan-3-yl)pyridin-3-yl)pyrazolo[1,5-a]pyridine-6-yl trifluoromethane sulfonate

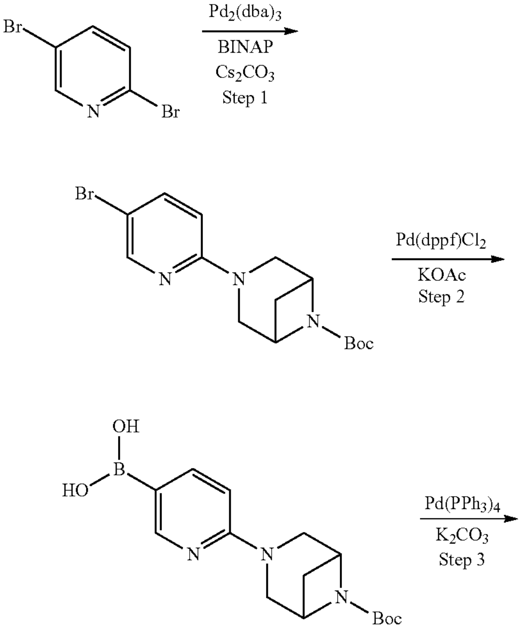

-continued

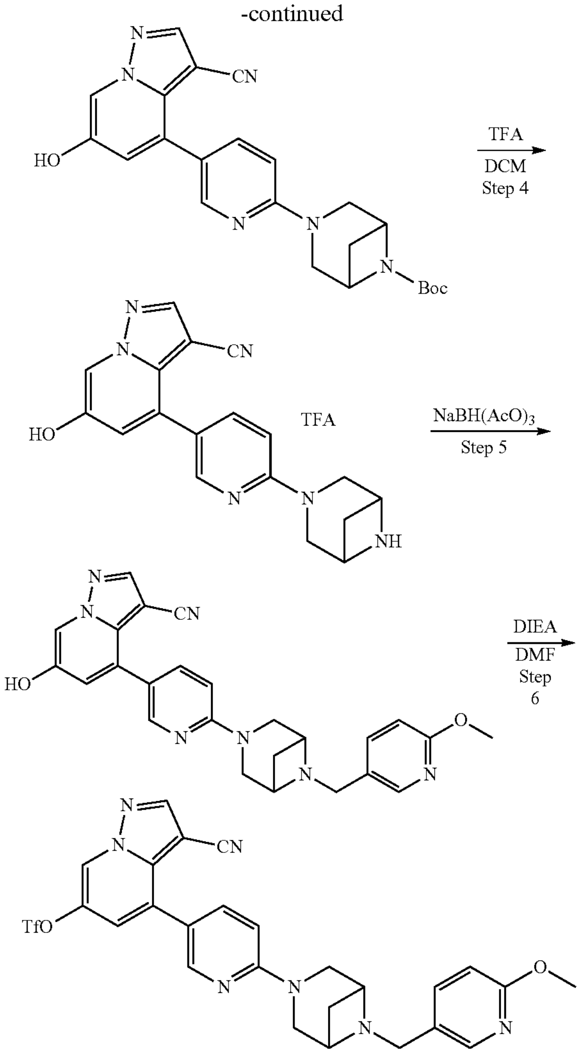

Step 1: tert-butyl 3-(5-bromopyridin-2-yl)-3,6-diazabicyclo[3.1.1]heptan-6-carboxylate Under protection of nitrogen, 2,5-dibromopyridine (4.74 g), tert-butyl 3,6-diazabicyclo[3.1.1]heptan-6-carboxylate (2.0 g), tris(dibenzylideneacetone)dipalladium (0.92 g), (t)-2,2'-Bis(diphenyl phosphino)-1,1'-binaphthalene (1.24 g) and cesium carbonate (6.52 g) were added to toluene (200 mL), and the mixture was heated to 110° C. and stirred overnight. The mixture was cooled to room temperature and filtered, the filter cake was washed with dichloromethane, and the filtrate was combined, concentrated, and purified through column chromatography (eluent: petroleum ether: ethyl acetate=4:1 (V:V)) to obtain tert-butyl 3-(5-bromopyridin-2-yl)-3,6-diazabicyclo[3.1.1]heptan-6-carboxylate (1.2 g).

Step 2: (6-(6-(tert-butoxycarbonyl)-3,6-diazabicyclo [3.1.1]heptan-3-yl) pyridin-3-yl) boronic acid Under protection of nitrogen, tert-butyl 3-(5-bromopyridin-2-yl)-3,6-diazabicyclo[3.1.1]heptan-6-carboxylate (354 mg), bis(pinacolato)diboron (510 mg), [1,1'-bis(diphenyl phosphino) ferrocene]dichloropalladium(II) (73 mg) and potassium acetate (196 mg) were sequentially added to dry dioxane (50 mL), and the reaction solution was heated to 90° C. and stirred overnight. After the reaction was completed, the mixture was cooled to room temperature and filtered through celite, the filter cake was washed with dichloromethane, and the filtrate was combined and concentrated to obtain (6-(6-(tert-butoxy carbonyl)-3,6-diazabicyclo [3.1.1]heptan-3-yl)pyridin-3-yl)boronic acid as a crude product, which was used directly in the next step.

Step 3: tert-butyl 3-(5-(3-cyano-6-hydroxypyrazolo [1,5-a]pyridine-4-yl)pyridin-2-yl)-3,6-diazabicyclo [3.1.1]heptan-6-carboxylate The crude product of (6-(6-(tert-butoxycarbonyl)-3,6-diazabicyclo[3.1.1]heptan-yl) pyridin-3-yl)boronic acid described above, 4-bromo-6-hydroxypyrazolo[1,5-a] pyridine-3-carbonitrile (238 mg) (synthesized according to patent WO2017/11776), and potassium carbonate (278 mg) were dissolved in a mixed solvent of dioxane and water (4:1) 50 mL. Under protection of nitrogen, tetrakis(triphenyl phosphine)palladium (110 mg) was added, and the mixture was heated to 90° C. and stirred for 4 hours. The reaction solution was cooled to room temperature, water (100 mL) was added, the mixture was extracted twice with ethyl acetate, and the organic phase was washed with brine, dried over anhydrous sodium sulphate, and evaporated under reduced pressure to dryness. The residue was purified through column chromatography (eluent: petroleum ether: ethyl acetate=2:1 (V:V)) to obtain tert-butyl 3-(5-(3-cyano-6-hydroxypyrazolo[1,5-a]pyridine-4-yl)pyridin-2-yl)-3,6-diazabicyclo[3.1.1]heptan-6-carboxylate (300 mg).

Step 4: 4-(6-(3,6-diazabicyclo[3.1.1]heptan-3-yl) pyridin-3-yl)-6-hydroxypyrazolo[1,5-a] pyridine-3-carbonitrile trifluoroacetate At room temperature, tertbutyl 3-(5-(3-cyano-6-hydroxypyrazolo[1,5-a]pyridine-4-yl) pyridin-2-yl)-3,6-diazabicyclo[3.1.1]heptan-6-carboxylate described above was dissolved in dichloromethane (20 mL), trifluoroacetic acid (4 mL) was added, the mixture was stirred for 2 hours, the reaction was completed, and the solvent was removed through vacuum evaporation under reduced pressure. To the residue was added tert-Butyl methyl ether (50 mL), the mixture was ultra-sonicated, the solid was precipitated and filtered, and the filter cake was washed twice with tert-butyl methyl ether and dried in vacuum to obtain 4-(6-(3,6-diazabicyclo[3.1.1]heptan-3-yl)pyridin-3-yl)-6-hydroxypyrazolo[1,5-a]pyridine-3-carbonitrile trifluoroacetate (250 mg).

Step 5: 6-hydroxy-4-(6-(6-((6-methoxypyridin-3-yl) methyl)-3,6-diazabicyclo[3.1.1] heptan-3-yl) pyridin-3-yl)pyrazolo[1,5-a]pyridine-3-carbonitrile At room temperature, 4-(6-(3,6-diazabicyclo[3.1.1]heptan-3-yl)pyridin-3-yl)-6-hydroxypyrazolo[1,5-a] pyridine-3-carbonitrile trifluoroacetate (25) mg) was dissolved in tetrahydrofuran (50 mL), 6-methoxypyridine-3-aldehyde (274 mg) was added, the mixture was stirred for 5 minutes, and sodium triacetoxyborohydride (500 mg) was added. The mixture was stirred until the reaction was completed, and the reaction solution was poured into an aqueous solution of saturated sodium bicarbonate, the mixture was extracted twice with ethyl acetate, the organic phase was washed with brine, dried over anhydrous sodium sulphate, evaporated under reduced pressure to remove the solvent, and purified through column chromatography (eluent: dichloromethane: methanol=30:1 (V:V)) to obtain 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (200 mg).

Step 6: 3-cyano-4-(6-(6-((6-methoxypyridin-3-yl)methyl)-3,6-diazabicyclo[3.1.1] heptan-3-yl) pyridin-3-yl)pyrazolo[1,5-a]pyridine-6-yl trifluoromethanesulfonate At room temperature, 6-hydroxy-4-(6-(6-((6-methoxypyridin-3-yl)methyl)-3,6-diazabicyclo[3.1.1]heptan-3-yl) pyridin-3-yl)pyrazolo[1,5-a]pyridine-3-carbonitrile (200 mg) was dissolved in DMF (30 mL), to the mixture was added DIEA (300 mg), then N-Phenyl-bis(trifluoromethanesulfonimide) (200 mg) was added. After the mixture was stirred at room temperature overnight, the reaction was completed, the mixture was poured into water (50 mL) and extracted twice with ethyl acetate. The organic phase was washed twice with brine, dried over anhydrous sodium sulphate, evaporated under reduced pressure to dryness, and purified through column chromatography (eluent: petroleum ether:ethyl acetate=3:1 (V:V)) to obtain 1,3-cyano-4-(6-(6-((6-methoxypyridin-3-yl) methyl)-3,6-diazabicyclo[3.1.1] heptan-3-yl) pyridin-3-yl) pyrazolo[1,5-a] pyridine-6-yl trifluoromethane sulfonate (210 mg).

Intermediate 6: 3-cyano-4-(6-(6-(4-(methylsulfonyl) benzyl)-3,6-diazabicyclo[3.1.1] heptan-3-yl) pyridin-3-yl)pyrazolo[1,5-a]pyridin-6-yl trifluoromethanesulfonate

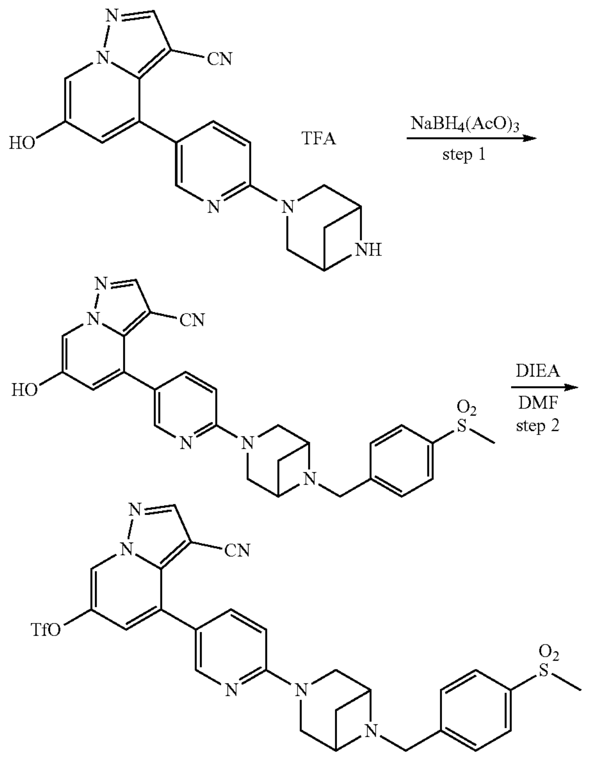

Step 1: 6-hydroxy-4-(6-(6-(4-(methylsulfonyl)benzyl)-3,6-diazabicyclo[3.1.1]heptan-3-yl) pyridin-3-yl)pyrazolo[1,5-a]pyridine-3-carbonitrile According to the method of step 5 of Intermediate 5, 4-(methylsulfonyl)benzaldehyde was used in place of 6-methoxypyridine-3-aldehyde to obtain the title compound.

Step 2: 3-cyano-4-(6-(6-(4-(methylsulfonyl)benzyl)-3,6-diazabicyclo[3.1.1] heptan-3-yl) pyridin-3-yl) pyrazolo[1,5-a]pyridin-6-yl trifluoromethanesulfonate According to the method of step 6 of Intermediate 5, 6-hydroxy-4-(6-(6-(4-methyl sulfonyl) benzyl)-3,6-diazabicyclo[3.1.1]heptan-3-yl) pyridin-3-yl) pyrazolo[1,5-a]pyridine-3-carbonitrile was used in place of 6-methoxy pyridin-3-yl) methyl)-3,6-diazabicyclo[3.1.1] heptan-3-yl) pyridin-3-yl) pyrazolo[1,5-a]pyridine-3-carbonitrile to obtain the title compound.

Intermediate 7: 3-cyano-4-(6-(4-((6-methoxy pyridin-3-yl) methyl) piperazin-1-yl) pyridin-3-yl) pyrazolo[1,5-a]pyridine-6-yl trifluoromethanesulfonate

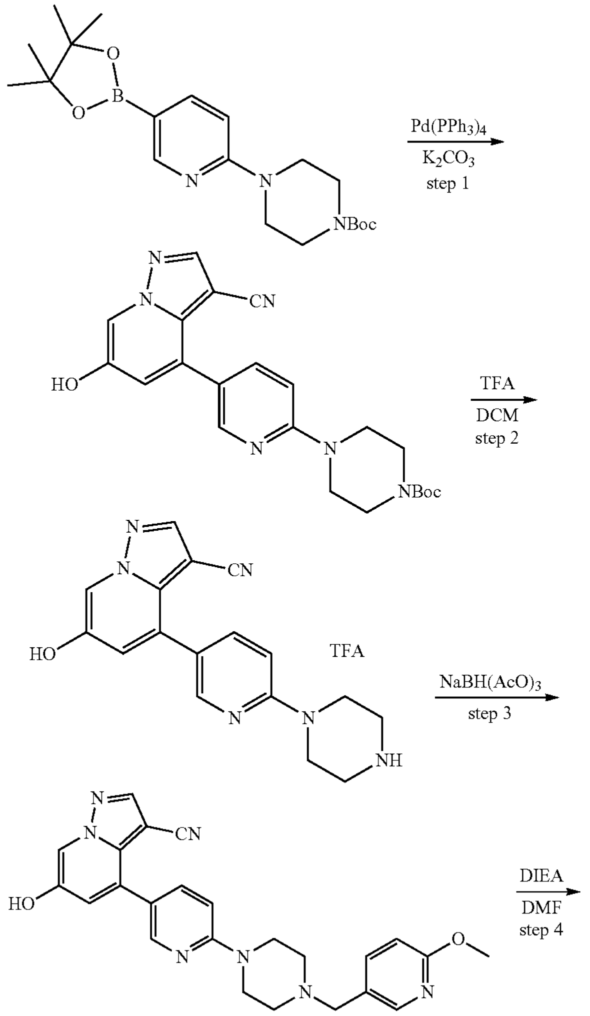

-continued

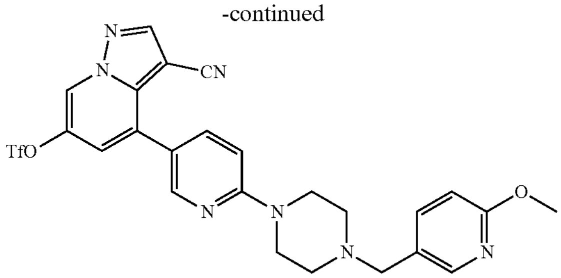

Step 1: tert-butyl 4-(5-(3-cyano-6-hydroxypyrazolo[1,5-a]pyridine-4-yl)pyridin-2-yl) piperazin-1-carboxylate According to the method of step 3 of Intermediate 5. tert-butyl 4-(5-(4,4,5,5-tetramethyl-1,3,2-dioxaborolan-2-yl)pyridin-2-yl)piperazin-1-carboxylate was used in place of (6-(6-(tert-butoxy carbonyl)-3,6-diazabicyclo[3.1.1]heptan-3-yl) pyridin-3-yl) boronic acid to obtain the title compound.

Step 2: 6-hydroxy-4-(6-(piperazin-1-yl) pyridin-3-yl) pyrazolo[1,5-a] pyridine-3-carbonitrile trifluoroacetate According to the method of step 4 of Intermediate 5. tert-butyl 4-(5-(3-cyano-6-hydroxy pyrazolo[1,5-a]pyridine-4-yl)pyridin-2-yl)piperazin-1-carboxylate was used in place of tert-butyl 3-(5-(3-cyano-6-hydroxypyrazolo[1,5-a] pyridine-4-yl) pyridin-2-yl)-3,6-diazabicyclo[3.1.1]heptan-6-carboxylate to obtain the title compound.

Step 3: 6-hydroxy-4-(6-(4-((6-methoxypyridin-3-yl) methyl)piperazin-1-yl) pyridin-3-yl) pyrazolo[1,5-a] pyridine-3-carbonitrile According to the method of step 5 of Intermediate 5, 6-hydroxy-4-(6-(piperazin-1-yl) pyridin-3-yl) pyrazolo[1,5-a]pyridine-3-carbonitrile trifluoroacetate was used in place of 4-(6-(3,6-diazabicyclo[3.1.1]heptan-3-yl)pyridin-3-yl)-6-hydroxypyrazolo[1,5-a]pyridine-3-carbonitrile trifluoroacetate to obtain the title compound.

Step 4: 3-cyano-4-(6-((6-methoxypyridin-3-yl) methyl)piperazin-1-yl)pyridin-3-yl) pyrazolo[1,5-a] pyridine-6-yl trifluoromethanesulfonate According to the method of step 6 of Intermediate 5, 6-hydroxy-4-(6-(4-((6-methoxy pyridin-3-yl)methyl)piperazin-1-yl)pyridin-3-yl)pyrazolo[1,5-a]pyridine-3-carbonitrile was used in place of 6-hydroxy-4-(6-(6-((6-methoxypyridin-3-yl) methyl)-3,6-diazabicyclo[3.1.1]heptan-3-yl) pyridin-3-yl) pyrazolo[1,5-a]pyridine-3-carbonitrile to obtain the title compound.

Intermediate 8: 3-cyano-4-(6-(4-(4-(methylsulfonyl) benzyl)piperazin-1-yl)pyridin-3-yl) pyrazolo[1,5-a] pyridine-6-yl trifluoromethanesulfonate

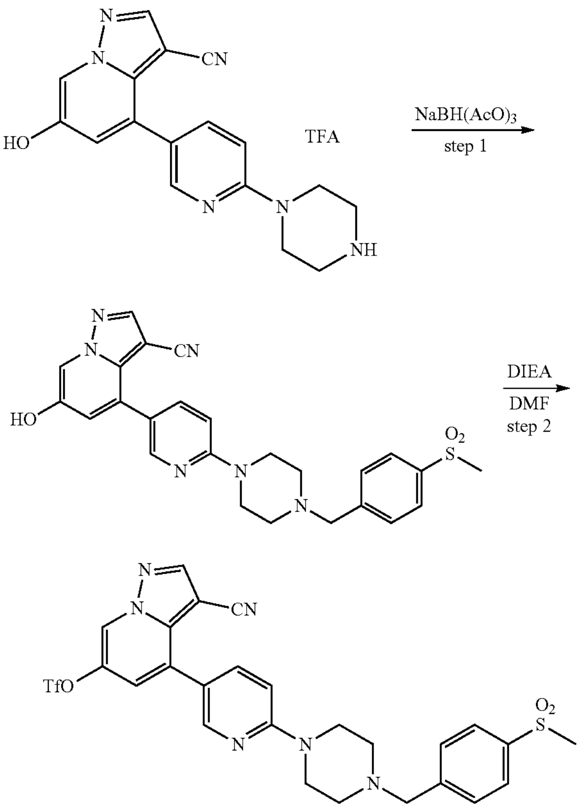

Step 1: 6-hydroxy-4-(6-(4-(4-(methylsulfonyl)benzyl)piperazin-1-yl)pyridin-3-yl) pyrazolo[1,5-a]pyridine-3-carbonitrile According to the method of step 3 of Intermediate 7, 4-(methylsulfonyl)benzaldehyde was used in place of 6-methoxypyridine-3-aldehyde to obtain the title compound.

Step 2: 3-cyano-4-(6-(4-(4-(methylsulfonyl)benzyl) piperazin-1-yl)pyridin-3-yl) pyrazolo[1,5-a]pyridine-6-yl trifluoromethanesulfonate According to the method of step 4 of Intermediate 7, 6-hydroxy-4-(6-(4-(4-methyl sulfonyl) benzyl) piperazin-1-yl) pyridin-3-yl)pyrazolo[1,5-a]pyridine-3-carbonitrile was used in place of 6-hydroxy-4-(6-(4-((6-methoxypyridin-3-yl) methyl) piperazin-1-yl) pyridin-3-yl) pyrazolo[1,5-a] pyridine-3-carbonitrile to obtain the title compound.

Intermediate 9: 3-cyano-4-(6-(6-(3-(methylsulfonyl)benzyl)-3,6-diazabicyclo[3.1.1] heptan-3-yl) pyridin-3-yl)pyrazolo[1,5-a]pyridin-6-yl trifluoromethanesulfonate

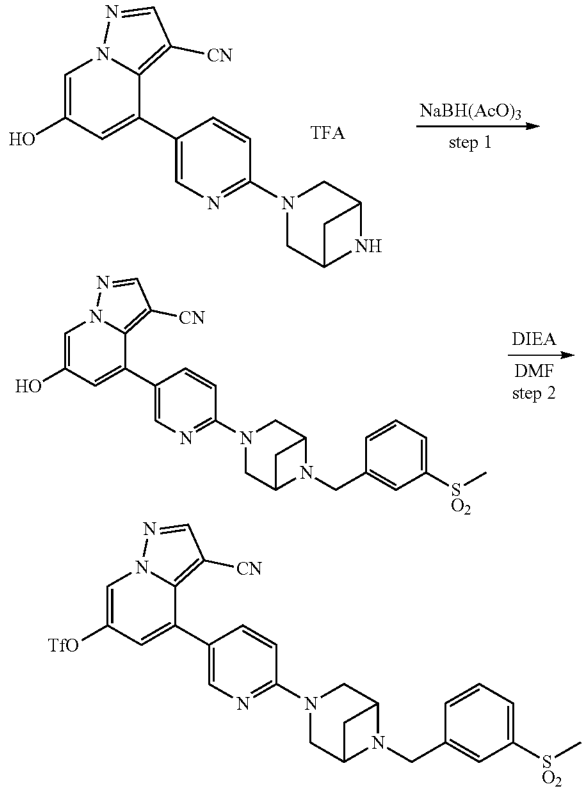

Step 1: 6-hydroxy-4-(6-(6-(3-(methylsulfonyl)benzyl)-3,6-diazabicyclo[3.1.1]heptan-3-yl) pyridin-3-yl)pyrazolo[1,5-a]pyridin-3-carbonitrile According to the method of step 5 of Intermediate 5, 3-(methylsulfonyl)benzaldehyde was used in place of 6-methoxypyridine-3-aldehyde to obtain the title compound.

Step 2: 3-cyano-4-(6-(6-(3-(methylsulfonyl)benzyl)-3,6-diazabicyclo[3.1.1]heptan-3-yl) pyridin-3-yl) pyrazolo[1,5-a]pyridin-6-yl trifluoromethanesulfonate According to the method of step 6 of Intermediate 5, 6-hydroxy-4-(6-(6-(3-(methyl sulfonyl) benzyl)-3,6-diazabicyclo[3.1.1]heptan-3-yl)pyridin-3-yl)pyrazolo[1,5-a] pyridin-3-carbonitrile was used in place of 6-methoxypyridin-3-yl) methyl)-3,6-diazabicyclo[3.1.1]heptan-3-yl) pyridin-3-yl) pyrazolo[1,5-a]pyridine-3-carbonitrile to obtain the title compound.

Intermediate 10: 3-cyano-4-(6-(4-(3-(methylsulfonyl)benzyl)piperazin-1-yl)pyridin-3-yl) pyrazolo[1,5-a]pyridine-6-yl trifluoromethanesulfonate

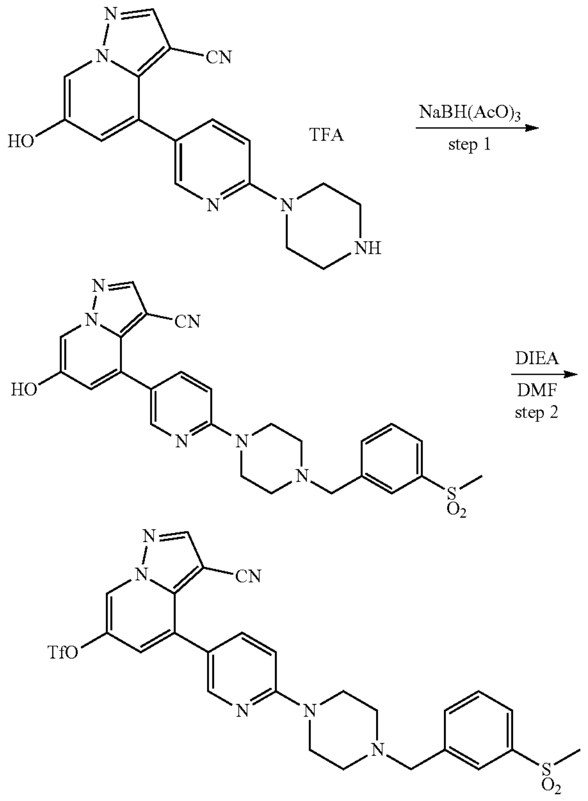

Step 1: 6-hydroxy-4-(6-(4-(3-(methylsulfonyl)benzyl)piperazin-1-yl)pyridin-3-yl) pyrazolo[1,5-a]pyridine-3-carbonitrile According to the method of step 3 of Intermediate 7, 3-(methylsulfonyl)benzaldehyde was used in place of 6-methoxypyridine-3-aldehyde to obtain the title compound.

Step 2: 3-cyano-4-(6-(4-(3-(methylsulfonyl)benzyl) piperazin-1-yl)pyridin-3-yl) pyrazolo[1,5-a]pyridine-6-yl trifluoromethansulfonate According to the method of step 4 of Intermediate 7, 6-hydroxy-4-(6-(4-(3-(methyl sulfonyl) benzyl) piperazin-1-yl) pyridin-3-yl) pyrazolo[1,5-a] pyridine-3-carbonitrile was used in place of 6-hydroxy-4-(4-(6-(4-((6-methoxypyridin-3-yl) methyl) piperazin-1-yl) pyridin-3-yl) pyrazolo[1,5-a]pyridine-3-carbonitrile to obtain the title compound.

Intermediate 11: 3-cyano-4-(6-(6-(4-(methylthio) benzyl)-3,6-diazabicyclo[3.1.1]heptan-3-yl) pyridin-3-yl)pyrazolo[1,5-a]pyridin-4-yl trifluoromethane-sulfonate

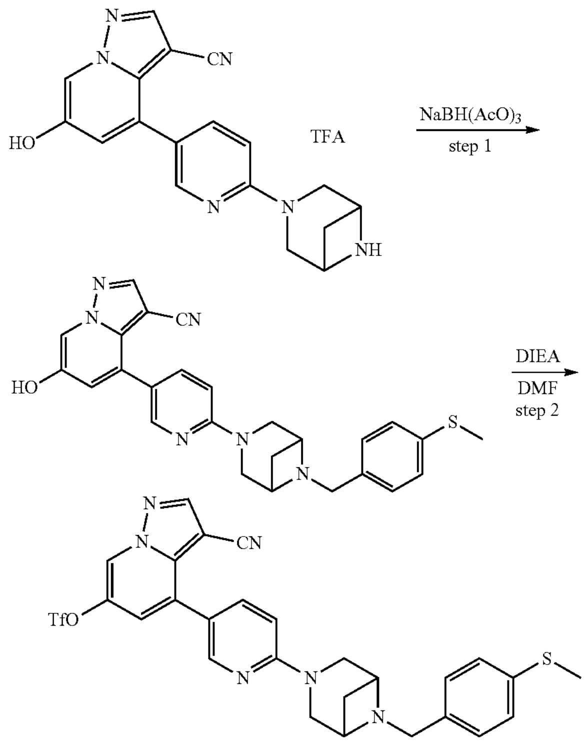

Step 1: 6-hydroxy-4-(6-(6-(4-(methylthio)benzyl)-3,6-diazabicyclo[3.1.1] heptan-3-yl) pyridin-3-yl) pyrazolo[1,5-a]pyridine-3-carbonitrile According to the method of step 5 of Intermediate 5, 4-(methylthio)benzaldehyde was used in place of 6-methoxypyridine-3-aldehyde to obtain the title compound.

Step 2: 3-cyano-4-(6-(6-(4-(methylthio)benzyl)-3,6-diazabicyclo[3.1.1]heptan-3-yl) pyridin-3-yl) pyrazolo[1,5-a]pyridin-4-yl trifluoromethanesulfonate According to the method of step 6 of Intermediate 5, 6-hydroxy-4-(6-(6-(4-(methylthio) benzyl)-3,6-diazabicyclo [3.1.1]heptan-3-yl) pyridin-3-yl) pyrazolo[1,5-a]pyridine-3-carbonitrile was used in place of 6-methoxy pyridin-3-yl) methyl)-3,6-diazabicyclo[3.1.1]heptan-3-yl) pyridin-3-yl) pyrazolo[1,5-a]pyridine-3-carbonitrile to obtain the title compound.

Intermediate 12: 3-cyano-4-(6-(4-(4-(methylthio) benzyl)piperazin-1-yl)pyridin-3-yl) pyrazolo[1,5-a] pyridine-6-yl trifluoromethanesulfonate

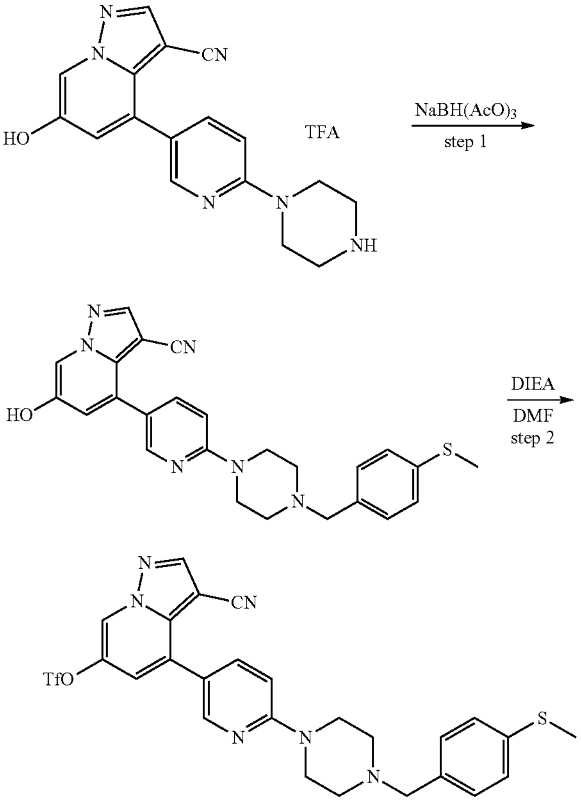

Step 1: 6-hydroxy-4-(6-(4-(4-(methylthio)benzyl) piperazin-1-yl)pyridin-3-yl) pyrazolo[1,5-a]pyridine-3-carbonitrile According to the method of step 3 of Intermediate 7, 4-(methylthio)benzaldehyde was used in place of 6-methoxypyridine-3-aldehyde to obtain the title compound.

Step 2: 3-cyano-4-(6-(4-(4-(methylthio)benzyl)piperazin-1-yl)pyridin-3-yl) pyrazolo[1,5-a]pyridine-6-yl trifluoromethanesulfonate According to the method of step 4 of Intermediate 7, 6-hydroxy-4-(6-(4-(4-(methylthio) benzyl) piperazin-1-yl) pyridin-3-yl)pyrazolo[1,5-a]pyridine-3-carbonitrile was used in place of 6-hydroxy-4-(6-(4-((6-methoxypyridin-3-yl)methyl)piperazin-1-yl)pyridin-3-yl)pyrazolo[1,5-a]pyridine-3-carbonitrile to obtain the title compound.

Intermediate 13: 3-cyano-4-(6-(6-((6-(methylthio) pyridin-3-yl) methyl)-3,6-diazabicyclo[3.1.1]heptan-3-yl) pyridin-3-yl) pyrazolo[1,5-a]pyridine-6-yl trifluoromethanesulfonate

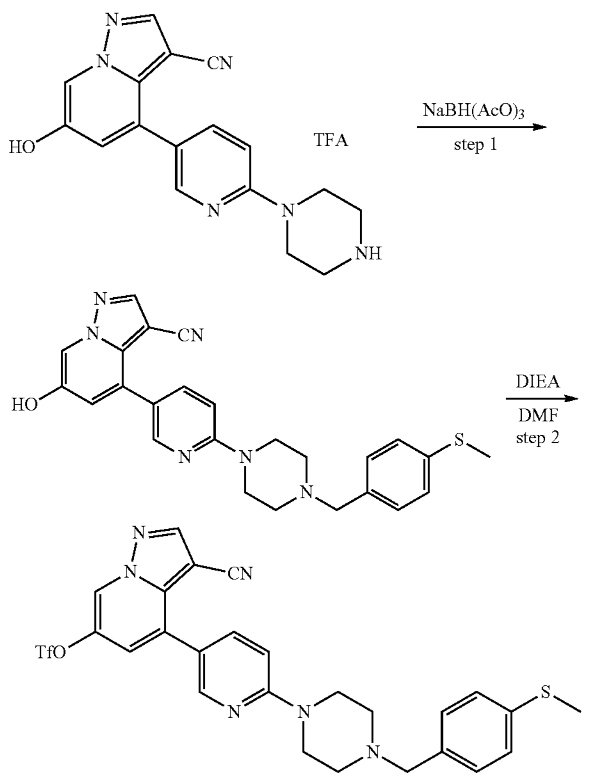

Step 1: 6-hydroxy-4-(6-(6-((6-(methylthio)pyridin-3-yl)methyl)-3,6-diazabicyclo[3.1.1]heptan-3-yl) pyridin-3-yl)pyrazolo[1,5-a]pyridine-3-carbonitrile According to the method of step 5 of Intermediate 5, 6-(methylthio)nicotinaldehyde was used in place of 6-methoxypyridine-3-aldehyde to obtain the title compound.

Step 2: 3-cyano-4-(6-(6-((6-(methylthio)pyridin-3-yl)methyl)-3,6-diazabicyclo[3.1.1]heptan-3-yl) pyridin-3-yl)pyrazolo[1,5-a]pyridine-6-yl trifluoromethanesulfonate According to the method of step 6 of Intermediate 5, 6-hydroxy-4-(6-(6-((6-(methyl thio) pyridin-3-yl)methyl)-3,6-diazabicyclo[3.1.1]heptan-3-yl)pyridin-3-yl)pyrazolo[1,5-a]pyridine-3-carbonitrile was used in place of 6-methoxypyridin-3-yl) methyl)-3,6-diazabicyclo[3.1.1]heptan-3-yl) pyridin-3-yl)pyrazolo[1,5-a]pyridine-3-carbonitrile to obtain the title compound.

Intermediate 14: 3-cyano-4-(64(4-4(6-(methylthio) pyridin-3-yl) methyl) piperazin-1-yl) pyridin-3-yl) pyrazolo[1,5-a]pyridine-6-yl-trifluoromethanesulfonate

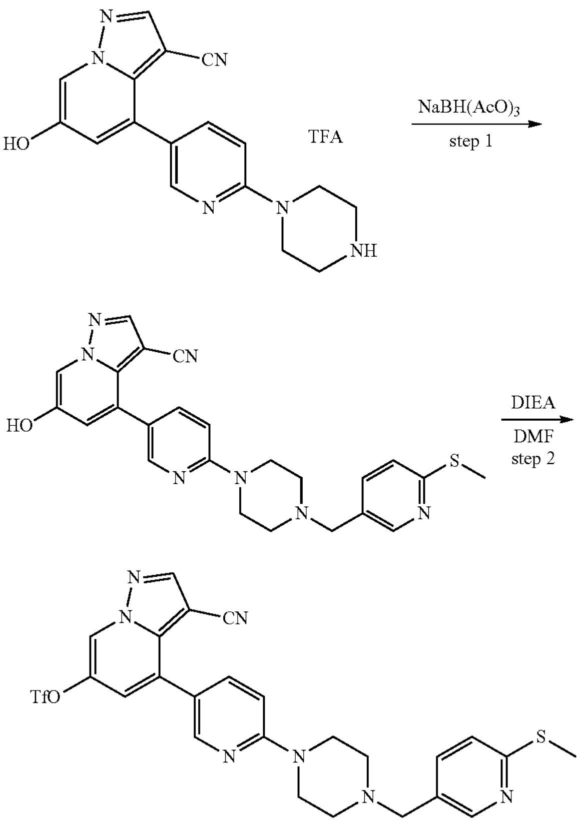

Step 1: 6-hydroxy-4-(6-(4-((6-(methylthio)pyridin-3-yl) methyl) piperazin-1-yl) pyridin-3-yl) pyrazolo [1,5-a]pyridine-3-carbonitrile According to the method of step 3 of Intermediate 7, 6-(methylthio)nicotinaldehyde was used in place of 6-methoxypyridine-3-aldehyde to obtain the title compound.

Step 2: 3-cyano-4-(6-(4-(4-(methylthio)benzyl)piperazin-1-yl)pyridin-3-yl) pyrazolo[1,5-a]pyridine-6-yl trifluoromethanesulfonate According to the method of step 4 of Intermediate 7, 6-hydroxy-4-(6-(4-(6-(methyl thio) pyridin-3-yl)methyl) piperazin-1-yl)pyridin-3-yl)pyrazolo[1,5-a]pyridine-3-carbonitrile was used in place of 6-hydroxy-4-(6-(4-((6-methoxypyridin-3-yl) methyl) piperazin-1-yl) pyridin-3-yl) pyrazolo[1,5-a]pyridine-3-carbonitrile to obtain the title compound.

Intermediate 15: 3-cyano-4-(6-(6-((5-(methylthio) pyridin-2-yl)methyl)-3,6-diaza bicyclo[3.1.1]heptan-3-yl) pyridin-3-yl) pyrazolo[1,5-a]pyridine-6-yl trifluoromethane sulfonate

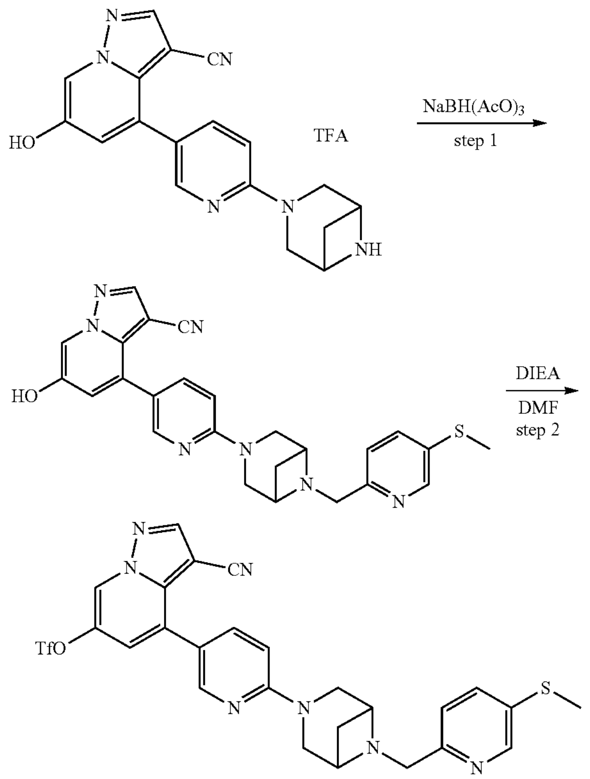

Step 1: 6-hydroxy-4-(6-(6-((5-(methylthio)pyridin-2-yl)methyl)-3,6-diazabicyclo[3.1.1]heptan-3-yl) pyridin-3-yl)pyrazolo[1,5-a]pyridine-3-carbonitrile According to the method of step 5 of Intermediate 5, 5-(methylthio)picolinaldehyde was used in place of 6-methoxypyridine-3-aldehyde to obtain the title compound.

Step 2: 3-cyano-4-(6-(6-((5-(methylthio)pyridin-2-yl)methyl)-3,6-diazabicyclo[3.1.1]heptan-3-yl) pyridin-3-yl)pyrazolo[1,5-a]pyridine-6-yl-trifluoromethanesulfonate According to the method of step 6 of Intermediate 5, 6-hydroxy-4-(6-(6-((5-(methyl thio) pyridin-2-yl)methyl)-3,6-diazabicyclo[3.1.1]heptan-3-yl)pyridin-3-yl)pyrazolo[1,5-a]pyridine-3-carbonitrile was used in place of 6-methoxy-pyridin-3-yl) methyl)-3,6-diazabicyclo[3.1.1] heptan-3-yl) pyridin-3-yl)pyrazolo[1,5-a]pyridine-3-carbonitrile to obtain the title compound.

Intermediate 16: 3-cyano-4-(6-(4-((5-(methylthio) pyridin-2-yl) methyl) piperazin-1-yl) pyridin-3-yl) pyrazolo[1,5-a]pyridine-6-yl-trifluoromethane-sulfonate

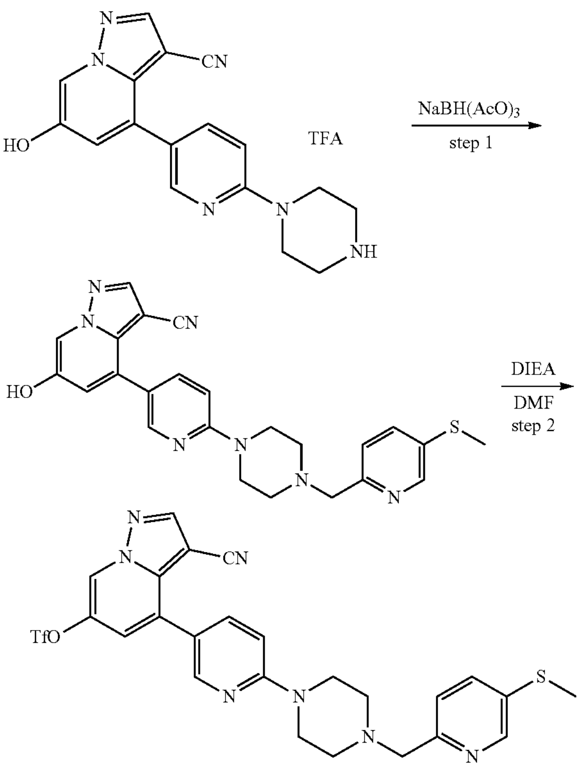

Step 1: 6-hydroxy-4-(6-(4-((5-(methylthio)pyridin-2-yl)methyl)piperazin-1-yl)pyridin-3-yl) pyrazolo[1,5-a]pyridine-3-carbonitrile According to the method of step 3 of Intermediate 7, 5-(methylthio)picolinaldehyde was used in place of 6-methoxypyridine-3-aldehyde to obtain the title compound.

Step 2: 3-cyano-4-(6-(4-((5-(methylthio)pyridin-2-yl)methyl)piperazin-1-yl) pyridin-3-yl) pyrazolo[1,5-a]pyridine-6-yl trifluoromethanesulfonate According to the method of step 4 of Intermediate 7, 6-hydroxy-4-(6-(4-((5-(methylthio) pyridin-2-yl)methyl) piperazin-1-yl)pyridin-3-yl)pyrazolo[1,5-a]pyridine-3-carbonitrile was used in place of 6-hydroxy-4-(6-(4-((6-methoxypyridin-3-yl) methyl) piperazin-1-yl) pyridin-3-yl) pyrazolo[1,5-a]pyridine-3-carbonitrile to obtain the title compound.

Intermediate 17: Synthesis of 3-cyano-4-(6-(6-((5-methoxypyridin-2-yl)methyl)-3,6-diazabicyclo [3.1.1]heptan-3-yl) pyridin-3-yl) pyrazolo[1,5-a] pyridine-4-yl trifluoromethanesulfonate

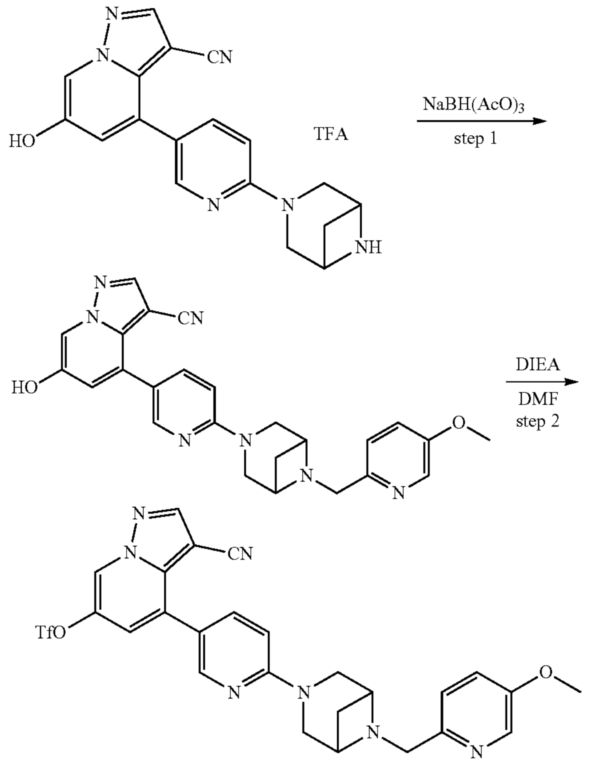

Step 1: 6-hydroxy-4-(6-(6-((5-methoxypyridin-2-yl) methyl)-3,6-diazabicyclo[3.1.1] heptan-3-yl) pyridin-3-yl)pyrazolo[1,5-a]pyridine-3-carbonitrile At room temperature, 4-(6-(3,6-diazabicyclo[3.1.1]heptan-3-yl) pyridin-3-yl)-6-hydroxy pyrazolo[1,5-a]pyridine-3-carbonitrile trifluoroacetate (250 mg) was dissolved in tetrahydrofuran (50 mL). 5-methoxy picolinaldehyde (274 mg) was added, the mixture was stirred for 5 minutes, and sodium triacetoxyborohydride (500 mg) was added. The mixture was stirred until the reaction was completed, and the reaction solution was poured into an aqueous solution of saturated sodium bicarbonate, the mixture was extracted twice with ethyl acetate, and the organic phase was washed with brine, dried over anhydrous sodium sulphate, evaporated under reduced pressure to remove the solvent, and purified through column chromatography (eluent: dichloromethane:methanol=30:1 (V:V)) to obtain 6-hydroxy-4-(6-(6-((6-methoxypyridin-3-yl)methyl)-3,6-diazabicyclo [3.1.1]heptan-3-yl) pyridin-3-yl) pyrazolo[1,5-a]pyridine-3-carbonitrile (210 mg).

Step 6: 3-cyano-4-(6-(6-((5-methoxypyridin-2-yl) methyl)-3,6-diazabicyclo[3.1.1]heptan-3-yl) pyridin-3-yl)pyrazolo[1,5-a]pyridine-6-yl trifluoromethane-sulfonate At room temperature. 6-hydroxy-4-(6-(6-((5-methoxy-pyridin-2-yl) methyl)-3,6-diazabicyclo[3.1.1]heptan-3-yl) pyridin-3-yl)pyrazolo[1,5-a]pyridine-3-carbonitrile (210 mg) was dissolved in DMF (30 mL), to the mixture was added DIEA (300 mg), and N-Phenyl-bis(trifluoromethane sulfonimide) (200 mg) was added. After the mixture was stirred at room temperature overnight, the reaction was completed, and the mixture was poured into water (50 mL) and extracted twice with ethyl acetate. The organic phase was washed twice with brine, dried over anhydrous sodium sulphate, evaporated under reduced pressure to dryness, and purified through column chromatography (eluent: petroleum ether:ethyl acetate=2:1 (V:V)) to obtain 1,3-cyano-4-(6-(6-((6-methoxypyridin-3-yl) methyl)-3,6-diazabicyclo[3.1.1] heptan-3-yl) pyridin-3-yl)pyrazolo[1,5-a]pyridine-6-yl trifluoromethanesulfonate (270 mg).

Intermediate 18: 3-cyano-4-(6-(4-(2-(methylsulfonyl)benzyl)piperazin-1-yl) pyridin-3-yl) pyrazolo[1,5-a]pyridine-6-yl trifluoromethanesulfonate

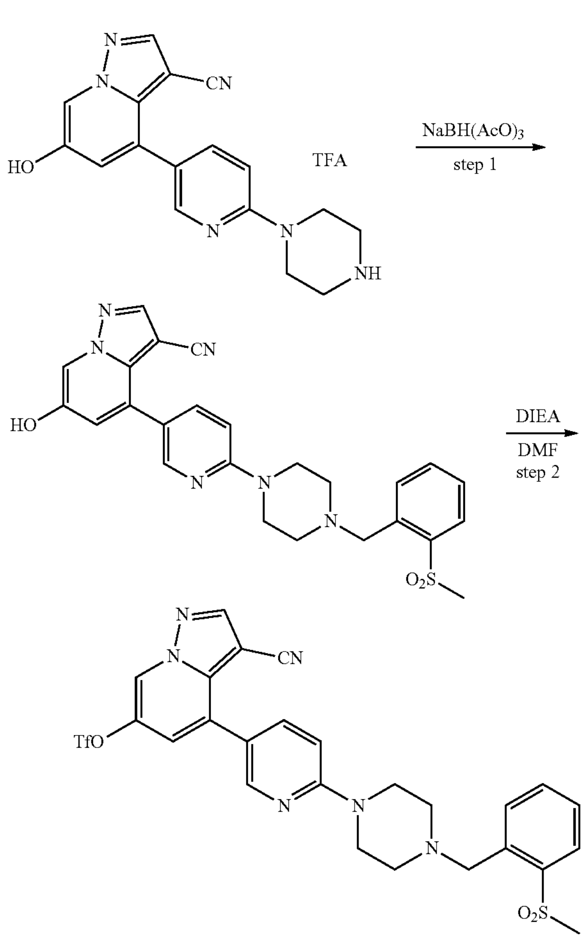

Step 1: 6-hydroxy-4-(6-(4-(2-(methylsulfonyl)benzyl)piperazin-1-yl)pyridin-3-yl) pyrazolo[1,5-a]pyridine-3-carbonitrile According to the method of step 3 of Intermediate 7, 2-(methylsulfonyl)benzaldehyde was used in place of 6-methoxypyridine-3-aldehyde to obtain the title compound.

Step 2: 3-cyano-4-(6-(4-(2-(methylsulfonyl) benzyl) piperazin-1-yl) pyridin-3-yl) pyrazolo[1,5-a]pyridine-6-yl trifluoromethanesulfonate According to the method of step 4 of Intermediate 7, 6-hydroxy-4-(6-(4-(2-(methyl sulfonyl) benzyl) piperazin-1-yl) pyridin-3-yl) pyrazolo[1,5-a]pyridine-3-carbonitrile was used in place of 6-hydroxy-4-(6-(4-((6-methoxypyridin-3-yl) methyl) piperazin-1-yl) pyridin-3-yl) pyrazolo[1,5-a] pyridine-3-carbonitrile to obtain the title compound.

Intermediate 19: 3-cyano-4-(6-(4-((5-methoxypyridin-2-yl)methyl)piperazin-1-yl) pyridin-3-yl) pyrazolo[1,5-a]pyridine-6-yl trifluoromethanesulfonate

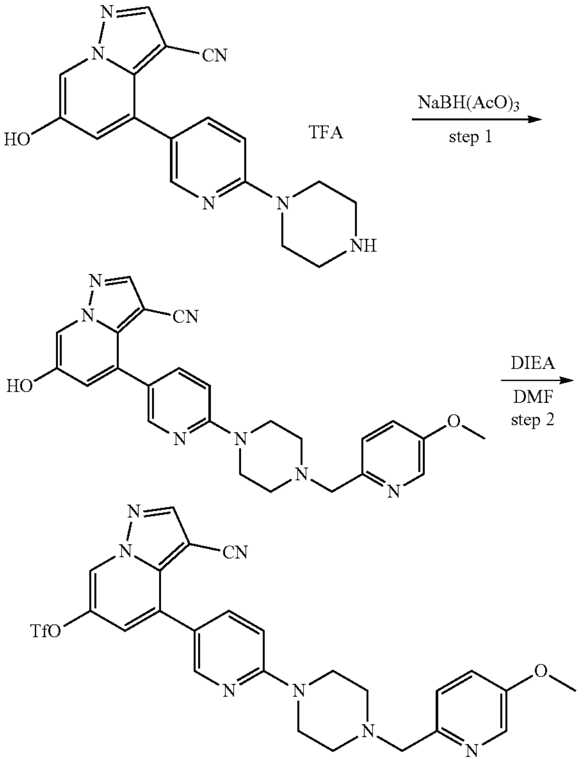

Step 1: 6-hydroxy-4-(6-(4-((5-methoxypyridin-2-yl) methyl) piperazin-1-yl) pyridin-3-yl) pyrazolo[1,5-a]pyridine-3-carbonitrile According to the method of step 3 of Intermediate 7, 5-methoxypicolinaldehyde was used in place of 6-methoxypyridine-3-aldehyde to obtain the title compound.

Step 2: 3-cyano-4-(6-(4-((5-methoxypyridin-2-yl) methyl)piperazin-1-yl)pyridin-3-yl) pyrazolo[1,5-a] pyridine-6-yl trifluoromethanesulfonate According to the method of step 4 of Intermediate 7, 6-hydroxy-4-(6-(4-((5-methoxy pyridin-2-yl) methyl)piperazin-1-yl)pyridin-3-yl)pyrazolo[1,5-a]pyridine-3-carbonitrile was used in place of 6-hydroxy-4-(6-(6-((6-methoxy pyridin-3-yl) methyl)-3,6-diazabicyclo[3.1.1]heptan-3-yl) pyridin-3-yl) pyrazolo[1,5-a]pyridine-3-carbonitrile to obtain the title compound.

Intermediate 20: 3-cyano-4-(6-(6-(2-(methylsulfonyl)benzyl)-3,6-diazabicyclo[3.1.1] heptan-3-yl) pyridin-3-yl)pyrazolo[1,5-a]pyridin-6-yl trifluoromethanesulfonate

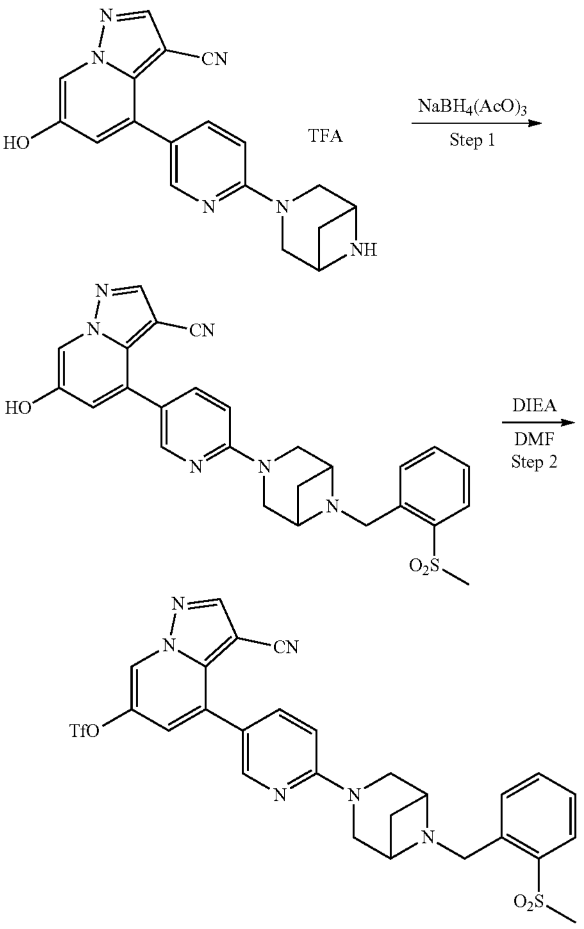

Step 1: 6-hydroxy-4-(6-(6-(2-(methylsulfonyl) benzyl)-3,6-diazabicyclo[3.1.1]heptan-3-yl) pyridin-3-yl)pyrazolo[1,5-a]pyridine-3-carbonitrile According to the method of step 5 of Intermediate 5, 2-(methylsulfonyl) benzaldehyde was used in place of 6-methoxypyridine-3-aldehyde to obtain the title compound.

Step 2: 3-cyano-4-(6-(6-(2-(methylsulfonyl)benzyl)-3,6-diazabicyclo[3.1.1] heptan-3-yl) pyridin-3-yl) pyrazolo[1,5-a]pyridin-6-yl trifluoromethanesulfonate According to the method of step 6 of Intermediate 5, 6-hydroxy-4-(6-(6-(2-(methyl sulfonyl) benzyl)-3,6-diazabicyclo[3.1.1]heptan-3-yl)pyridin-3-yl)pyrazolo[1,5-a] pyridine-3-carbonitrile was used in place of 6-methoxypyridin-3-yl)methyl)-3,6-diazabicyclo[3.1.1] heptan-3-yl) pyridin-3-yl) pyrazolo[1,5-a]pyridine-3-carbonitrile to obtain the title compound.

Intermediate 21: Synthesis of 4-(6-(3,6-diazabicyclo [3.1.1] heptan-3-yl) pyridin-3-yl)-6-(1-difluoro methyl-1Hpyrazol-4-yl)pyrazolo[1,5-a]pyridine-3-carbonitrile

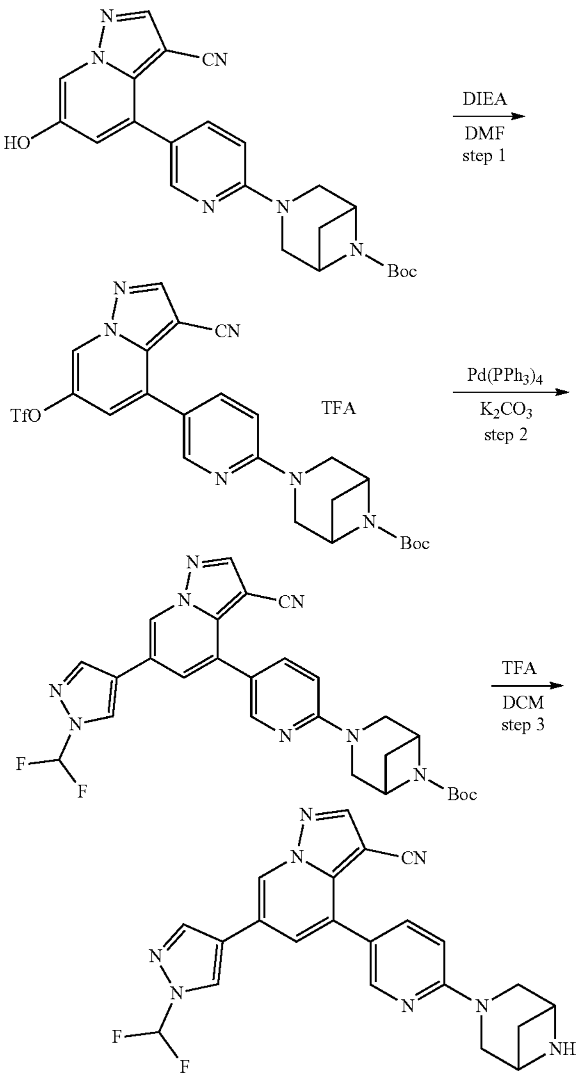

Step 1: tert-butyl 3-(5-(3-cyano-6-(trifluoromethane sulfonate) pyrazolo[1,5-a]pyridine-4-yl) pyridin-2-yl)-3,6-diazabicyclo[3.1.1]heptan-6-carboxylate tert-butyl 3-(5-(3-cyano-6-hydroxy pyrazolo[1,5-a]pyridine-4-yl) pyridin-2-yl)-3,6-diazabicyclo[3.1.1]heptan-6-carboxylate (432 mg) was dissolved in DMF (20 mL), to the mixture was added DIEA (260 mg), and N-Phenyl-bis (trifluoromethane sulfonimide) (400 mg) was added. The mixture was stirred at room temperature for 2 hours and poured into water (100 mL), and the mixture was extracted with ethyl acetate. The organic phase was washed with brine, dried over anhydrous sodium sulphate and filtered, the filtrate was concentrated under reduced pressure, and the residue was purified through column chromatography (eluent: petroleum ether:ethyl acetate=2:1 (V:V)) to obtain the target compound (450 mg).

Step 2: tert-butyl 3-(5-(3-cyano-6-(1-(difluoromethyl)-1Hpyrazol-4-yl)pyrazolo[1,5-a] pyridine-4-yl) pyridin-2-yl)-3,6-diazabicyclo[3.1.1]heptan-6-carboxylate To a flask charged with dioxane and water (50 mL, volume ratio 5:1) were sequentially added tert-butyl 3-(5-(3-cyano-6-(trifluoromethane sulfonate) pyrazolo[1,5-a] pyridine-4-yl) pyridin-2-yl)-3,6-diazabicyclo[3.1.1]heptan-6-carboxylate (282 mg), (1-(difluoromethyl)-1H-pyrazol-4-yl) boronic acid (100 mg), tetrakis (triphenyl phosphine) palladium (55 mg) and potassium carbonate (139 mg), and the flask was purged 3 times with nitrogen. The mixture was heated to 80° C. and stirred overnight. The mixture was cooled to room temperature, the reaction solution was poured into water (150 mL), and the mixture was extracted with ethyl acetate. The organic phase was dried over anhydrous sodium sulphate and filtered, the filtrate was concentrated under reduced pressure, and the residue was purified through column chromatography (eluent: dichloromethane: methanol=20:1 (V:V)) to obtain the target compound (200 mg).

Step 3: 4-(6-(3,6-diazabicyclo[3.1.1]heptan-3-yl) pyridin-3-yl)-6-(1-(difluoromethyl)-1Hpyrazol-4-yl) pyrazolo[1,5-a]pyridine-3-carbonitrile At room temperature, tert-butyl 3-(5-(3-cyano-6-(1-(difluoromethyl)-1Hpyrazol-4-yl) pyrazolo[1,5-a]pyridine-4-yl)pyridin-2-yl)-3,6-diazabicyclo[3.1.1]heptan-6-carboxylate (200 mg) above was dissolved in dichloromethane (20 mL), trifluoroacetic acid (4 mL) was added, and the mixture was stirred for 2 hours and evaporated under reduced pressure in vacuum to remove the solvent. To the residue was added an aqueous solution of saturated sodium bicarbonate until the system was weak basic, and the solid thus formed was filtered and dried to obtain the target compound (130 mg).

Intermediate 22: Synthesis of 4-(6-(3,8-diazabicyclo [3.2.1]octane-3-yl) pyridin-3-yl)-6-(1-(difluoro methyl)-1Hpyrazol-4-yl)pyrazolo[1,5-a]pyridine-3-carbonitrile

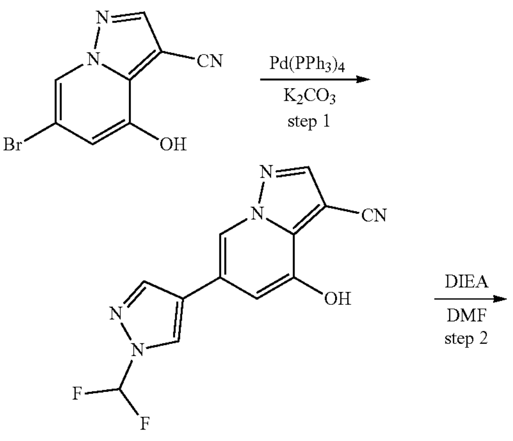

-continued

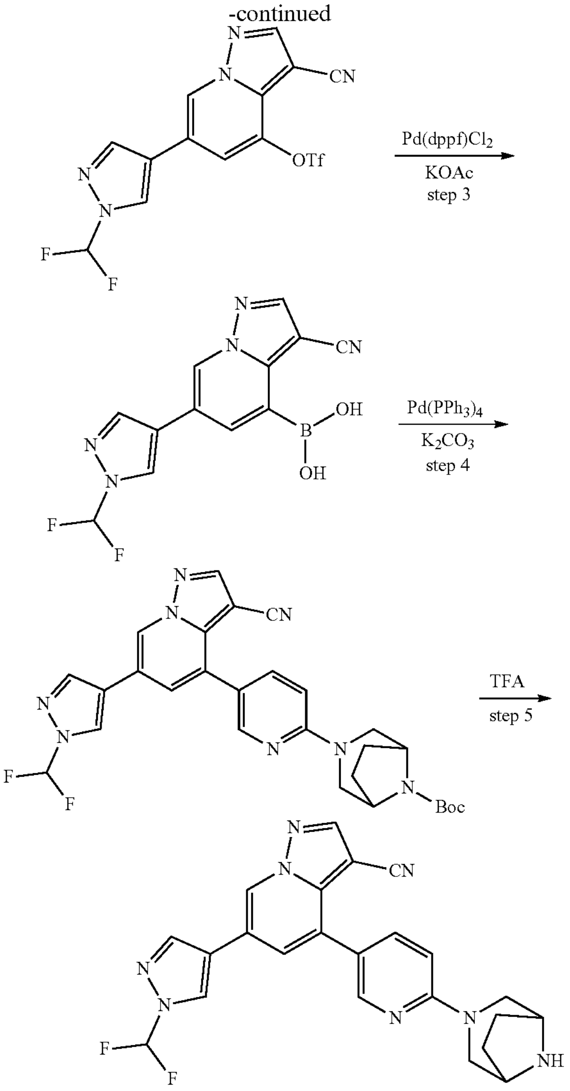

Step 1: 6-(1-(difluoromethyl)-1Hpyrazol-4-yl)-4-hydroxypyrazolo[1,5-a]pyridine-3-carbonitrile To a flask charged with dioxane and water (50 mL, volume ratio 5:1) were sequentially added 6-bromo-4-hydroxypyrazolo[1,5-a]pyridine-3-carbonitrile (238 mg), (1-(difluoromethyl)-1H-pyrazol-4-yl)boronic acid (200 mg), tetrakis(triphenylphosphine) palladium (110 mg) and potassium carbonate (278 mg), and the flask was purged 3 times with nitrogen. The mixture was heated to 80° C. and stirred overnight. The mixture was cooled to room temperature, the reaction solution was poured into water (150 mL), and the mixture was extracted with ethyl acetate. The organic phase was dried over anhydrous sodium sulphate and filtered, the filtrate was concentrated under reduced pressure, and the residue was purified through column chromatography (eluent: dichloromethane:methanol=20:1 (V:V)) to obtain the target compound (250 mg).

Step 2: 3-cyano-6-(1-(difluoromethyl)-1Hpyrazol-4-yl)pyrazolo[1,5-a]pyridine-4-yl trifluoro methanesulfonate 6-(1-(difluoromethyl)-1Hpyrazol-4-yl)-4-hydroxypyrazolo[1,5-a]pyridine-3-carbonitrile (250 mg) was dissolved in DMF (20 mL), to the mixture was added DIEA (300 mg), and N-Phenyl-bis (trifluoromethanesulfonimide) (400 mg) was added. The mixture was stirred at room temperature for 2 hours and poured into water (50 mL), and the mixture was extracted with ethyl acetate. The organic phase was washed with brine, dried over anhydrous sodium sulphate and filtered, the filtrate was concentrated under reduced pressure, and the residue was purified through column chromatography (eluent: petroleum ether:ethyl acetate=1:1 (V:V)) to obtain the target compound (300 mg).

Step 3: 3-cyano-6-(1-(difluoromethyl)-1Hpyrazol-4-yl) pyrazolo[1,5-a]pyridine-4-yl boronic acid Under protection of nitrogen, 3-cyano-6-(1-(difluoromethyl)-1Hpyrazol-4-yl) pyrazolo[1,5-a]pyridine-4-yl trifluoromethanesulfonate (300 mg), bis(pinacolato)diboron (254 mg). [1,1'-bis(diphenyl phosphino)ferrocene]dichloropalladium(II) (73 mg) and potassium acetate (196 mg) were added to dry dioxane (30 mL), and the mixture was heated to 90° C. and stirred overnight. The mixture was cooled to room temperature and filtered, the filter cake was washed with dichloromethane, and the filtrate was evaporated under reduced pressure to dryness to obtain the target compound as a crude product, which was used directly in the next step.

Step 4: tert-butyl 3-(5-(3-cyano-6-(1-(difluoromethyl)-1Hpyrazol-4-yl)pyrazolo[1,5-a]pyridine-4-yl) pyridin-2-yl)-3,6-diazabicyclo[3.2.1]octane-6-carboxylate To a flask charged with dioxane and water (50 mL, volume ratio 5:1) were sequentially added the boronic acid obtained above (150 mg), tert-butyl 3-(5-bromopyridin-2-yl)-3,8-diazabicyclo[3.2.1]octane-8-carboxylate (183 mg), tetrakis (triphenyl phosphine)palladium (50 mg) and potassium carbonate (139 mg), and the flask was purged 3 times with nitrogen. The mixture was heated to 80° C. and stirred overnight. The mixture was cooled to room temperature, the reaction solution was poured into water (150 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the target compound (250 mg).

Step 5: 4-(6-(3,8-diazabicyclo[3.2.1]octane-3-yl) pyridin-3-yl)-6-(1-(difluoromethyl)-1H-pyrazol-4-yl) pyrazolo[1,5-a]pyridine-3-carbonitrile At room temperature, tert-butyl 3-(5-(3-cyano-6-(1-(difluoromethyl)-1Hpyrazol-4-yl) pyrazolo[1,5-a]pyridine-4-yl)pyridin-2-yl)-3,6-diazabicyclo[3.2.1]octane-6-carboxylate above (250 mg) was dissolved in dichloromethane (20 mL), trifluoroacetic acid (5 mL) was added, and the mixture was stirred for 1 hour and evaporated under reduced pressure in vacuum to remove the solvent. To the residue was added an aqueous solution of saturated sodium bicarbonate until the system was weak basic, and the solid thus formed was filtered and dried to obtain the target compound (180 mg).

Intermediate 23: Synthesis of 4-(5-(3,6-diazabicyclo[3.1.1]heptan-3-yl)pyrazin-2-yl)-6-(1-(difluoro methyl)-1Hpyrazol-4-yl)pyrazolo[1,5-a]pyridine-3-carbonitrile

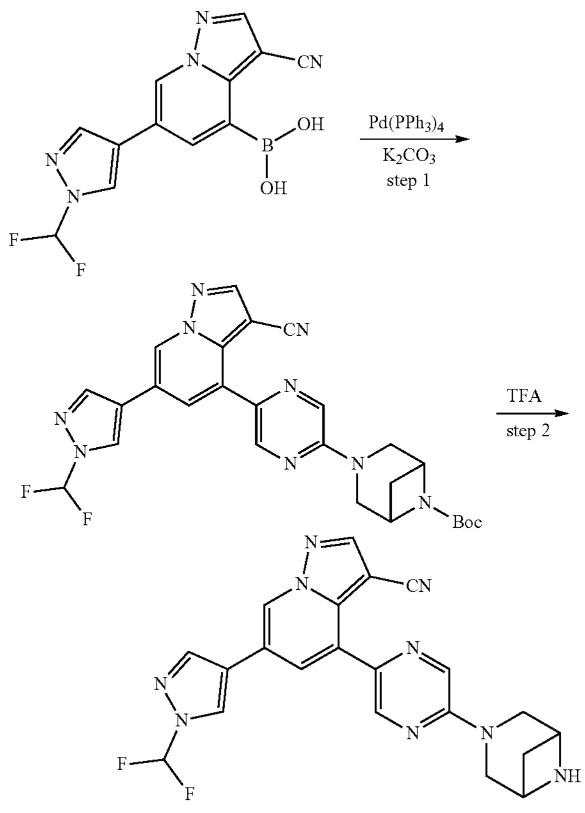

Step 1: tert-butyl 3-(5-(3-cyano-6-(1-difluoromethyl-1Hpyrazol-4-yl)pyrazolo[1,5-a] pyridine-4-yl) pyrazin-2-yl)-3,6-diazabicyclo[3.1.1]heptan-6-carboxylate Under protection of nitrogen, 3-cyano-6-(1-(difluoromethyl)-1Hpyrazol-4-yl)pyrazolo[1,5-a]pyridine-4-ylboronic acid (303 mg) and tert-butyl 3-(5-chloropyrazin-2-yl)-3,6-diazabicyclo[3.1.1]heptan-6-carboxylate of step 2 of Intermediate 4 (250 mg) were dissolved in a mixed solvent of dioxane and water (5:1) (50 mL), and tetrakis(triphenylphosphine)palladium (110 mg) and anhydrous potassium carbonate powder (278 mg) were sequentially added. Then the mixture was heated to 85° C. stirred for 2 hours and cooled to room temperature, the reaction solution was poured into water (150 mL), the mixture was extracted with dichloromethane, the extract was washed with brine, dried over anhydrous sodium sulphate and filtered, the filtrate was concentrated under reduced pressure, and the residue was purified through silica gel chromatography (eluent: petroleum ether:ethyl acetate=2:1 (V:V)) to obtain the title compound (400 mg).

Step 2: 4-(5-(3,6-diazabicyclo[3.1.1]heptan-3-yl) pyrazin-2-yl)-6-(1-(difluoromethyl)-1H-pyrazol-4-yl)pyrazolo[1,5-a]pyridine-3-carbonitrile At 0° C., to a solution of tert-butyl 3-(5-(3-cyano-6-(1-difluoromethyl-1Hpyrazol-4-yl) pyrazolo[1,5-a]pyridine-4-yl)pyrazin-2-yl)-3,6-diazabicyclo[3.1.1]heptan-6-carboxylate obtained in step 1 (400 mg) in dichloromethane (20 mL) was slowly dropwise added trifluoroacetic acid (5 mL), after the dropwise addition was completed, the mixture was let warm up to room temperature and stirred for 1 hour. The reaction solution was concentrated, an aqueous solution of saturated sodium bicarbonate was added to adjust the pH to weak basic, and the solid thus formed was filtered and dried to obtain the title compound (240 mg).

Intermediate 24: Synthesis of 6-(1-(difluoromethyl)-1Hpyrazol-4-yl)-4-(6-(piperazin-1-yl) pyridin-3-yl) pyrazolo[1,5-a]pyridine-3-carbonitrile

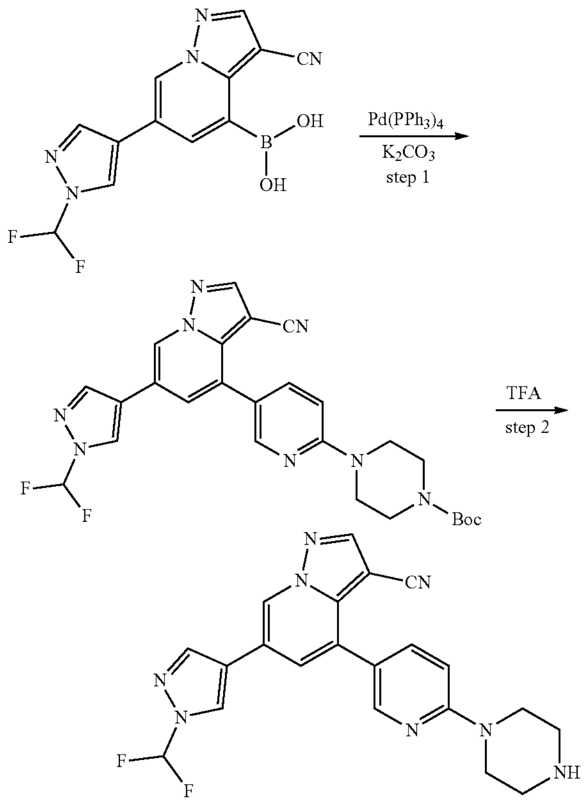

Step 1: tert-butyl 4-(5-(3-cyano-4-(1-(difluoromethyl)-1Hpyrazol-4-yl)pyrazolo[1,5-a] pyridine-4-yl) pyridin-2-yl)piperazin-1-carboxylate Under protection of nitrogen, 3-cyano-6-(1-(difluoromethyl)-1Hpyrazol-4-yl)pyrazolo[1,5-a]pyridine-4-ylboronic acid (303 mg) and tert-butyl 4-(5-bromopyridin-2-yl) piperazin-1-carboxylate (342 mg) were dissolved in a mixed solvent of dioxane and water (5:1) (50 mL), and tetrakis (triphenylphosphine)palladium (110 mg) and anhydrous potassium carbonate powder (278 mg) were sequentially added. Then the mixture was heated to 85° C. and stirred for 2 hours, after the mixture was cooled to room temperature, the reaction solution was poured into water (150 mL), the mixture was extracted with dichloromethane, the extract was washed with brine, dried over anhydrous sodium sulphate and filtered, the filtrate was concentrated under reduced pressure, and the residue was purified through silica gel chromatography (eluent: petroleum ether:ethyl acetate=2:1 (V:V)) to obtain the title compound (410 mg).

Step 2: 6-(1-(difluoromethyl)-1Hpyrazol-4-yl)-4-(6-(piperazin-1-yl)pyridin-3-yl) pyrazolo[1,5-a]pyridine-3-carbonitrile At 0° C. to a solution of tert-butyl 4-(5-(3-cyano-6-(1-(difluoromethyl)-1Hpyrazol-4-yl) pyrazolo[1,5-a]pyridine-4-yl)pyridin-2-yl)piperazin-1-carboxylate obtained in step 1 (410 mg) in dichloromethane (20 mL) was slowly dropwise added trifluoroacetic acid (5 mL), after the dropwise addition was completed, the mixture was let warm up to room temperature and stirred for 1 hour. After the reaction solution was concentrated, an aqueous solution of saturated sodium bicarbonate was added to adjust the pH to weak basic, and the solid thus formed was filtered and dried to obtain the title compound (220 mg).

Intermediate 25: Synthesis of 4-(6-(3,6-diazabicyclo [3.1.1]heptan-3-yl)pyridin-3-yl)-6-(1-trifluoro methyl-1Hpyrazol-4-yl)pyrazolo[1,5-a]pyridine-3-carbonitrile

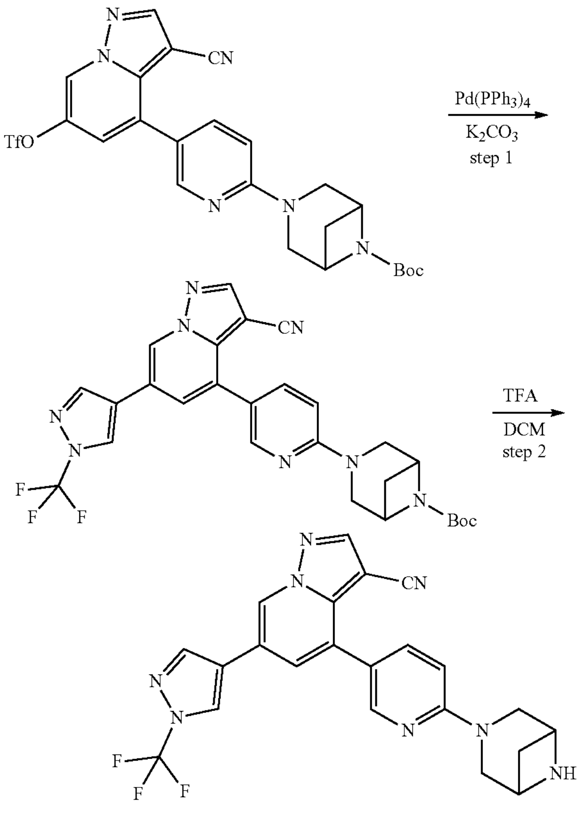

Step 1: tert-butyl 34(54(3-cyano-6-(1-(trifluoromethyl)-1Hpyrazol-4-yl)pyrazolo[1,5-a]pyridine-4-yl) pyridin-2-yl)-3,6-diazabicyclo[3.1.1]heptan-6-carboxylate To a flask charged with dioxane and water (40 mL, volume ratio 5:1) were sequentially added tert-butyl 3-(5-(3-cyano-6-(trifluoromethanesulfonate)pyrazolo[1,5-a]pyridine-4-yl) pyridin-2-yl)-3,6-diazabicyclo[3.1.1]heptan-6-carboxylate (282 mg), 1-trifluoromethyl pyrazol-4-boronic acid (110 mg), tetrakis(triphenylphosphine)palladium (50 mg) and potassium carbonate (139 mg), and the flask was purged 3 times with nitrogen. The mixture was heated to 80° C. and stirred overnight. The mixture was cooled to room temperature, the reaction solution was poured into water (150 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the target compound (170 mg).

Step 2: Synthesis of 4-(6-(3,6-diazabicyclo[3.1.1] heptan-3-yl)pyridin-3-yl)-6-(1-trifluoro methyl-1Hpyrazol-4-yl)pyrazolo[1,5-a]pyridine-3-carbonitrile At room temperature, tert-butyl 3-(5-(3-cyano-6-(1-(trifluoromethyl)-1Hpyrazol-4-yl) pyrazolo[1,5-a]pyridine-4-yl)pyridin-2-yl)-3,6-diazabicyclo[3.1.1]heptan-6-carboxylate above (170 mg) was dissolved in dichloromethane (20 mL), trifluoroacetic acid (4 mL) was added, and the mixture was stirred for 2 hours and evaporated under reduced pressure in vacuum to remove the solvent. To the residue was added an aqueous solution of saturated sodium bicarbonate until the system was weak basic, and the solid thus formed was filtered and dried to obtain the target compound (120 mg).

Example 1: 4-(6-(4-acryloylpiperazin-1-yl)pyridin-3-yl)-6-(1-methyl-1Hpyrazol-4-yl)pyrazolo[1,5-a] pyridine-3-carbonitrile

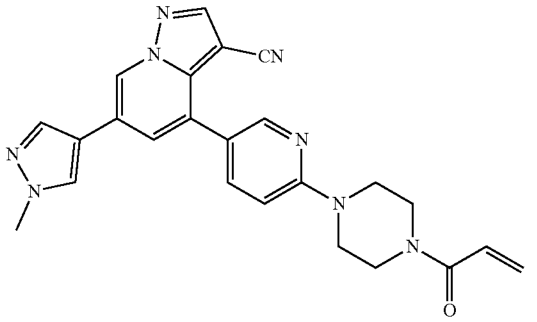 [SMILES: C=CC(=O)N1CCN(c2ccc(-c3cc(-c4cnn(C)c4)cn4ncc(C#N)c34)cn2)CC1]

At 0° C. Intermediate 1 (39 mg) was dissolved in THF (10 mL), acrylylchloride (15 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (30 mg).

$^1H$ NMR (400 MHz, $CDCl_3$) δ 8.64 (1H, d, J=1.2 Hz), 8.38 (1H, d, J=2.8 Hz), 8.26 (1H, s), 7.76-7.78 (2H, m), 7.68 (1H, s), 7.39 (1H, d, J=1.6 Hz), 6.79 (1H, d, J=8.8 Hz), 6.62

(1H, dd, J=16.8 Hz, 10.4 Hz), 6.35 (1H, dd, J=16.8 Hz, 2.0 Hz), 5.75 (1H, dd, J=10.4 Hz, 2.0 Hz), 3.99 (3H, s). 3.66-3.88 (8H, m).

Example 2: 4-(6-(4-(cyclopent-1-ene-1-carbonyl) piperazin-1-yl) pyridin-3-yl)-6-(1-methyl-1Hpyrazol-4-yl)pyrazolo[1,5-a]pyridine-3-carbonitrile

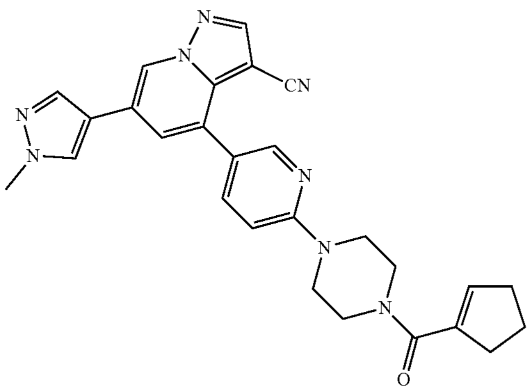 [SMILES: Cn1cc(-c2cc(-c3ccc(N4CCN(C(=O)C5=CCCC5)CC4)nc3)c3c(C#N)cnn3c2)cn1]

At 0° C., Intermediate 1 (39 mg) was dissolved in THF (10 mL), cyclopent-1-ene-1-carbonyl chloride (20 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (40 mg).

$^1$H NMR (400 MHz, $CDCl_3$) δ 8.63 (1H, s), 8.38 (1H, d, J=2.4 Hz), 8.26 (1H, s), 7.75-7.78 (2H, m), 7.68 (1H, s), 7.39 (1H, s), 6.79 (1H, d, J=8.4 Hz), 5.92-5.95 (1H, m), 3.99 (3H, s), 3.66-3.82 (8H, m), 2.62-2.68 (2H, m), 2.48-2.52 (2H, m), 1.94-2.02 (2H, m).

Example 3: 4-(5-(6-((6-methoxypyridin-3-yl) methyl)-3,6-diazabicyclo[3.1.1] heptan-3-yl) pyrazin-2-yl)-6-(1-methyl-1Hpyrazol-4-yl) pyrazolo [1,5-a]pyridine-3-carbonitride

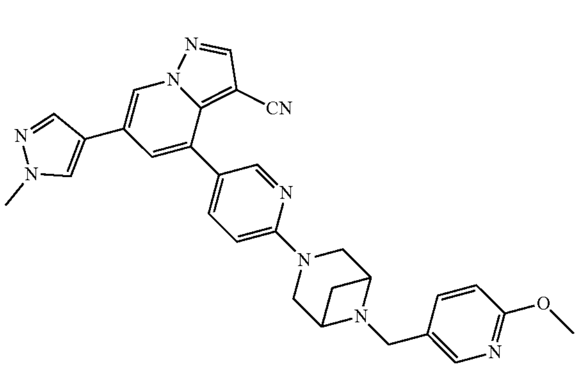

At 0° C. Intermediate 4 (40 mg) was dissolved in THF (10 mL). 6-methoxy nicotinaldehyde (27 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (35 mg).

$^1$H NMR (400 MHz, $CDCl_3$) δ 8.67 (1H, s), 8.56 (1H, s), 8.31 (1H, s), 8.28 (1H, s), 8.11 (1H, s), 7.82 (1H, s), 7.66-7.72 (3H, m), 6.74 (1H, d, J=8.8 Hz), 4.00 (3H, s), 3.77-3.87 (7H, m), 3.58-3.76 (4H, m), 2.69-2.86 (1H, m), 1.66-1.73 (1H, m).

Example 4: 6-(4-hydroxy-4-methylpiperidin-1-yl)-4-(6-(4-((6-methoxypyridin-3-yl) methyl) piperazin-1-yl) pyridin-3-yl)pyrazolo[1,5-a]pyridine-3-carbonitrile

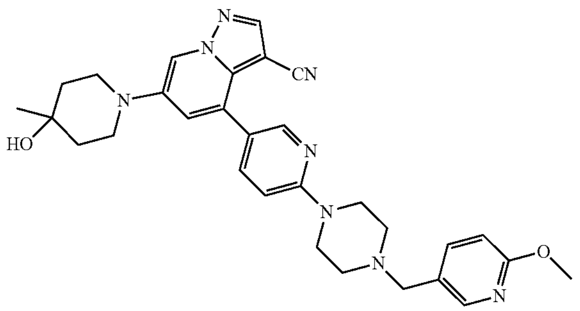

To a flask charged with toluene (20 mL) were sequentially added Intermediate 7 (57 mg). 4-methyl-4-hydroxy piperidine (23 mg), tris(dibenzylideneacetone)dipalladium (9 mg), (±)-2,2'-Bis (diphenylphosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography (developing solvent: dichloromethane: methanol=20:1 (V:V)) to obtain the target compound (25 mg).

$^1$H NMR (400 MHz, $CDCl_3$) δ 8.30 (1H, d, J=2.8 Hz), 8.15 (1H, s), 8.07 (1H, d, J=2.0 Hz), 8.02 (1H, d, J=2.0 Hz), 7.70 (1H, dd, J=8.8 Hz, 2.8 Hz), 7.59-7.63 (1H, m), 7.16 (1H, d, J=2.0 Hz), 6.72-6.75 (2H, m), 3.94 (3H, s), 3.60-3.66 (4H, m), 3.49 (2H, s), 3.27-3.33 (2H, m), 3.14-3.20 (2H, m), 2.52-2.58 (4H, m), 1.71-1.86 (4H, m), 1.33 (3H, s), 1.15 (1H, s).

Example 5: 6-(4-(2-hydroxypropan-2-yl)piperidin-1-yl)-4-(6-(4-((6-methoxy pyridin-3-yl) methyl) piperazin-1-yl)pyridin-3-yl)pyrazolo[1,5-a]pyridine-3-carbonitrile

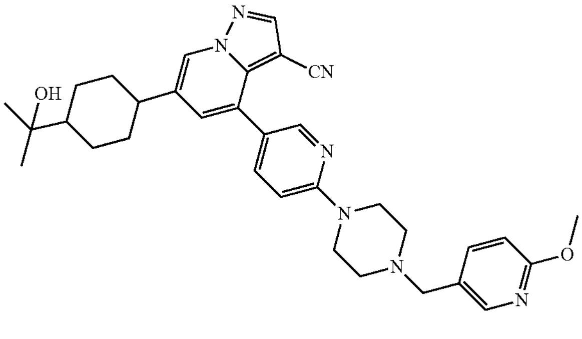 [SMILES: COc1ccc(CN2CCN(c3ccc(-c4cc(C5CCC(C(C)(C)O)CC5)cn5ncc(C#N)c45)cn3)CC2)cn1]

To a flask charged with toluene (20 mL) were sequentially added Intermediate 7 (57 mg). 2-(piperidin-4-yl)propan-2-ol (29 mg), tris(dibenzylideneacetone)dipalladium (9 mg), (±)-2,2'-Bis(diphenylphosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (22 mg).

$^1$H NMR (400 MHz, $CDCl_3$) δ 8.30 (1H, d, J=2.4 Hz), 8.15 (1H, s), 8.07 (1H, d, J=2.0 Hz), 7.99 (1H, d, J=2.0 Hz), 7.70 (1H, dd, J=8.8 Hz, 2.0 Hz), 7.62 (1H, d, J=8.8 Hz), 7.16 (1H, d, J=1.6 Hz), 6.75 (1H, s), 6.73 (1H, s), 3.94 (3H, s), 3.60-3.70 (6H, m), 3.49 (2H, s), 2.65-2.72 (2H, m), 2.52-2.58 (4H, m), 1.92 (2H, d, J=12.0 Hz), 1.41-1.62 (3H, n), 1.23 (6H, s).

Example 6: 6-(1-methyl-1Hpyrazol-4-yl)-4-(6-(4-(2-methylcyclopent-1-ene-1-carbonyl) piperazin-1-yl) pyridin-3-yl)pyrazolo[1,5-a]pyridine-3-carbonitrile

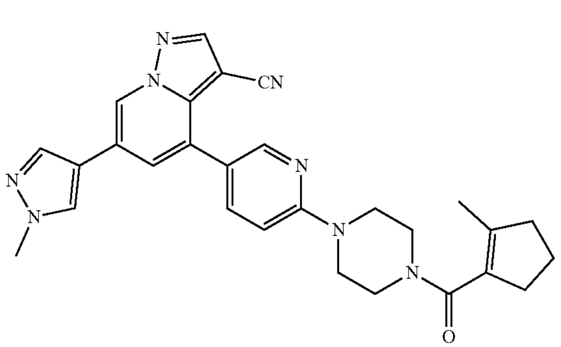 [SMILES: CC1=C(C(=O)N2CCN(c3ccc(-c4cc(-c5cnn(C)c5)cn5ncc(C#N)c45)cn3)CC2)CCC1]

At 0° C., Intermediate 1 (39 mg) was dissolved in THE (10 mL), 2-methylcyclopent-1-ene-1-carbonyl chloride (23 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (36 mg).

$^1$H NMR (400 MHz, $CDCl_3$) δ 8.63 (1H, s), 8.38 (1H, d, J=2.4 Hz), 8.25 (1H, s), 7.75-7.78 (2H, m), 7.68 (1H, s), 7.39 (1H, s), 6.80 (0H, d, J=8.0 Hz), 3.99 (3H, s), 3.78-3.85 (2H, m), 3.64-3.70 (4H, m) 3.53-3.61 (2H, m), 2.59-2.65 (2H, m), 2.41 (2H, t, J=7.2 Hz), 1.90-1.98 (2H, m), 1.74 (3H, s).

Example 7: 6-(3-hydroxy-3-methyl azetidin-1-yl)-4-(6-(6-((6-methoxypyridin-3-yl) methyl)-3,6-diazabicyclo[3.1.1]heptan-3-yl)pyridin-3-yl)pyrazolo[1,5-a]pyridine-3-carbonitrile

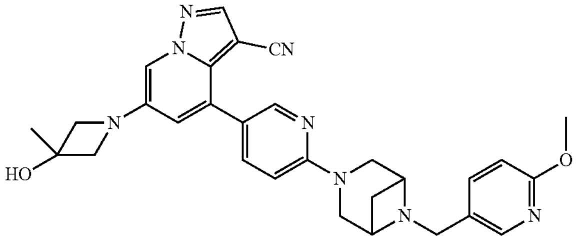 [SMILES: COc1ccc(CN2C3CC2CN(c2ccc(-c4cc(N5CC(C)(O)C5)cn5ncc(C#N)c45)cn2)C3)cn1]

To a flask charged with toluene (20 mL) were sequentially added Intermediate 5 (59 mg), 3-methylazetidin-3-ol hydrochloride (27 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane: methanol=20:1 (V:V)) to obtain the target compound (15 mg).

$^1$H NMR (400 MHz, $CDCl_3$) s 8.37 (1H, d, J=2.4 Hz), 8.15 (1H, s), 8.10 (1H, d, J=2.4 Hz), 7.78 (1H, dd, J=8.8 Hz, 2.4 Hz), 7.71 (1H, d, J=1.6 Hz), 7.63 (1H, dd, J=8.8 Hz, 2.4 Hz), 6.73 (1H, d, J=1.6 Hz), 6.71 (1H, d, J=8.4 Hz), 6.68 (1H, d, J=8.4 Hz), 3.90-3.93 (5H, m), 3.76-3.87 (6H, m). 3.56-3.64 (4H, m), 2.66-2.72 (1H, m), 1.67 (3H, s), 1.62-1.66 (1H, m).

Example 8: 4-(5-(3-cyano-6-(1-methyl-1Hpyrazol-4-yl)pyrazolo[1,5-a]pyridine-4-yl)pyridin-2-yl)-N,N-dimethylpiperazin-1-carbothioamide

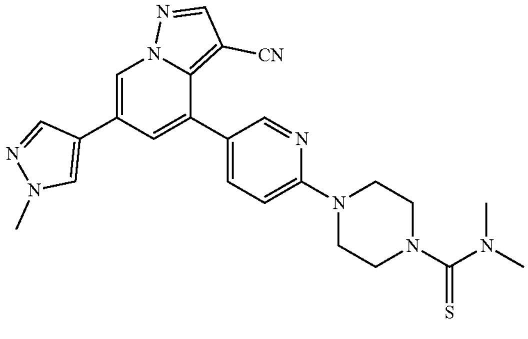 [SMILES: CN(C)C(=S)N1CCN(c2ccc(-c3cc(-c4cnn(C)c4)cn4ncc(C#N)c34)cn2)CC1]

At 0° C., Intermediate 1 (39 mg) was dissolved in THF (10 mL), dimethylcarbamothioic chloride (20 mg) and triethylamine (50 mg) were added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (27 mg).

$^1$H NMR (400 MHz, $CDCl_3$) δ 8.64 (1H, d, J=1.6 Hz), 8.38 (1H, d, J=2.4 Hz), 8.26 (1H, s), 7.79 (1H, s), 7.77 (1H, dd, J=8.4 Hz, 2.4 Hz), 7.68 (1H, s), 7.40 (1H, d, J=1.6 Hz), 6.80 (1H, d, J=8.4 Hz), 3.99 (3H, s), 3.74-3.77 (4H, m), 3.63-3.66 (4H, m), 3.20 (6H, s).

Example 9: 6-(1-methyl-1Hpyrazol-4-yl)-4(6-(4-((5-(methylthio)pyridin-2-yl) methyl) piperazin-1-yl) pyridin-3-yl)pyrazolo[1,5-a]pyridine-3-carbonitrile

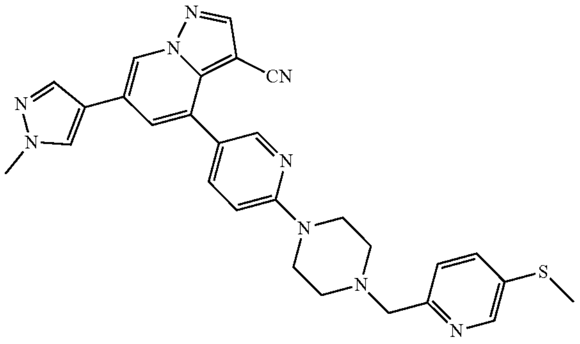

At 0° C., Intermediate 1 (39 mg) was dissolved in THF (10 mL), 5-(methylthio)picolinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (31 mg).

$^1$H NMR (400 MHz, $CDCl_3$) δ 8.64 (1H, d, J=1.6 Hz), 8.48 (1H, d, J=2.4 Hz), 8.36 (1H, d, J=2.4 Hz), 8.25 (1H, s), 7.81 (1H, dd, J=8.0 Hz. 2.4 Hz), 7.79 (1H, s), 7.76 (1H, dd, J=8.8 Hz, 2.4 Hz), 7.70 (1H, s), 7.41 (1H, d, J=1.2 Hz), 7.34 (1H, d, J=8.0 Hz), 6.79 (1H, d, J=8.8 Hz), 4.43 (2H, d, J=13.6 Hz), 3.99 (3H, s), 3.98 (2H, s), 3.69 (2H, t, J=12.8 Hz), 3.40 (2H, d, J=11.2 Hz), 2.66 (2H, t, J=11.2 Hz), 2.59 (3H, s).

Example 10: 6-(1-methyl-1Hpyrazol-4-yl)-4-(6-(4-((6-(methylthio)pyridin-3-yl) methyl) piperazin-1-yl)pyridin-3-yl)pyrazolo[1,5-a]pyridine-3-carbonitrile

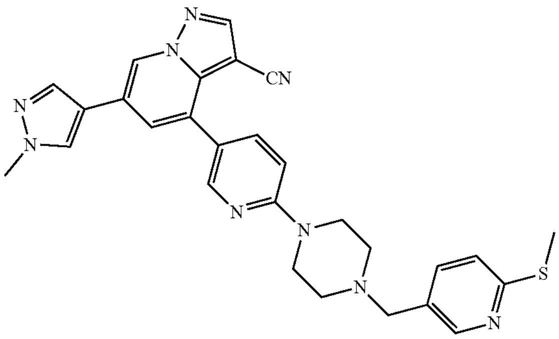

At 0° C., Intermediate 1 (39 mg) was dissolved in THF (10 mL). 6-(methylthio)nicotinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (21 mg).

$^1$H NMR (400 MHz, $CDCl_3$) δ 8.62 (1H, s), 8.39 (1H, s), 8.36 (1H, d, J=2.8 Hz), 8.26 (1H, s), 7.78 (1H, s), 7.74 (1H, dd, J=8.8 Hz. 2.8 Hz), 7.67 (1H, s), 7.54 (1H, d, J=8.4 Hz), 7.38 (1H, s), 7.18 (1H, d, J=8.0 Hz), 6.77 (1H, d, J=9.2 Hz), 3.99 (3H, s), 3.63-3.68 (4H, m), 3.51 (2H, s), 2.54-2.60 (7H, m).

Example 11: 6-(2-hydroxy-2-methylpropoxy)-4-(6-(6-((6-(methylthio)pyridin-3-yl) methyl)-3,6-diazabicyclo[3.1.1]heptan-3-yl)pyridin-3-yl)pyrazolo[1,5-a]pyridine-3-carbonitrile

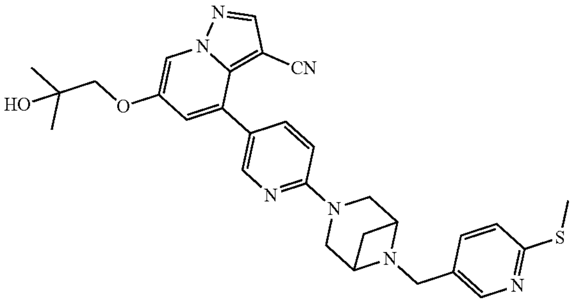 [SMILES: CSc1ccc(CN2C3CC2CN(c2ccc(-c4cc(OCC(C)(C)O)cn5ncc(C#N)c45)cn2)C3)cn1]

At 0° C. 6-hydroxy-4-(6-(6-((6-(methylthio)pyridin-3-yl) methyl)-3,6-diazabicyclo[3.1.1]heptan-3-yl) pyridin-3-yl) pyrazolo[1,5-a]pyridine-3-carbonitrile (50 mg) was dissolved in dioxane (10 mL), 2,2-dimethyloxan (1 ml) and potassium carbonate (50 mg) were sequentially added, the mixture was heated in a sealed tube to 60° C. and stirred for 12 hours. The reaction solution was cooled and poured into water, the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (15 mg).

$^1$H NMR (400 MHz, $CDCl_3$) δ 8.39-4.42 (2H, m), 8.21 (1H, s), 8.15 (1H, d, J=1.6 Hz), 7.77 (1H, dd, J=8.8 Hz, 2.8 Hz), 7.52-7.57 (1H, m), 7.16 (1H, d, J=2.4 Hz), 7.14 (1H, d, J=8.0 Hz), 6.67 (1H, d, J=8.4 Hz), 3.87 (2H s), 3.72-3.85 (4H, m), 3.52-3.64 (4H, m), 2.65-2.71 (1H, m), 2.55 (3H, s), 2.05 (1H, s), 1.65 (1H, d, J=8.0 Hz), 1.39 (6H, s).

Example 12: 4-(6-(4-(2-(methoxymethyl)cyclopent-1-ene-1-carbonyl) piperazin-1-yl) pyridin-3-yl)-6-(1-methyl-1Hpyrazol-4-yl)pyrazolo[1,5-a]pyridine-3-carbonitrile

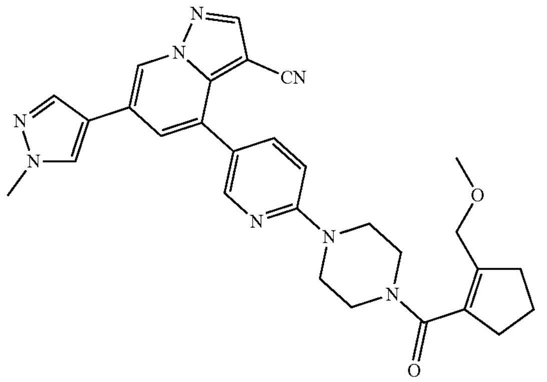 [SMILES: COCC1=C(C(=O)N2CCN(c3ccc(-c4cc(-c5cnn(C)c5)cn5ncc(C#N)c45)cn3)CC2)CCC1]

At 0° C. Intermediate 1 (39 mg) was dissolved in THF (10 mL). 2-(methoxymethyl) cyclopent-1-ene-1-carbonyl chloride (20 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the title compound (30 mg).

$^1$H NMR (400 MHz, $CDCl_3$) δ 8.64 (1H, d, J=1.2 Hz), 8.38 (1H, d, J=2.4 Hz), 8.26 (1H, s), 7.76-7.79 (2H, m), 7.68 (1H, s), 7.39 (1H, d, J=1.2 Hz), 6.80 (1H, d, J=8.8 Hz), 3.99 (3H, s), 3.98 (2H, s), 3.78-3.84 (2H, n), 3.63-3.71 (4H, m), 3.53-3.59 (2H, m), 3.33 (3H, s), 2.66 (2H, t, J=7.6 Hz), 2.51 (2H, t, J=7.6 Hz), 1.95-2.03 (2H, m).

Example 13: 6-(3-cyanoazetidin-1-yl)-4-(6-(6-((6-methoxypyridin-3-yl) methyl)-3,6-diazabicyclo [3.1.1]heptan-3-yl)pyridin-3-yl)pyrazolo[1,5-a]pyridine-3-carbonitrile

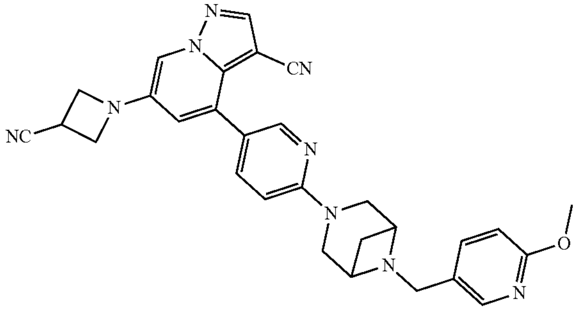 [SMILES: COc1ccc(CN2C3CC2CN(c2ccc(-c4cc(N5CC(C#N)C5)cn5ncc(C#N)c45)cn2)C3)cn1]

To a flask charged with toluene (20 mL) were sequentially added Intermediate 5 (59 ng), 3-cyano azetidine hydrochloride (24 ng), tris(dibenzylideneacetone)dipalladium (9 mg), (i)-2,2'-Bis(diphenyl phosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (15 ng).

$^1$H NMR (400 MHz, $CDCl_3$) δ 8.37 (1H, d, J=2.4 Hz), 8.19 (1H, s), 8.10 (1H, s), 7.78 (1H, dd, J=8.8 Hz. 2.4 Hz), 7.74 (1H, d, J=2.0 Hz), 7.57-7.71 (I H, m), 6.67-6.73 (3H, m), 4.27 (2H, t, J=7.2 Hz), 4.16 (2H, t, J=7.2 Hz), 3.92 (3H, s), 3.49-3.90 (9H, m). 2.58-2.82 (1H, m), 1.62-1.71 (1H, m).

Example 14: 4-(6-(6-((6-methoxypyridin-3-yl) methyl)-3,6-diazabicyclo[3.1.1] heptan-3-yl) pyridin-3-yl)-(2-oxa-azaspiro[3.3]hepta-6-yl)pyrazolo[1,5-a]pyridine-3-carbonitrile

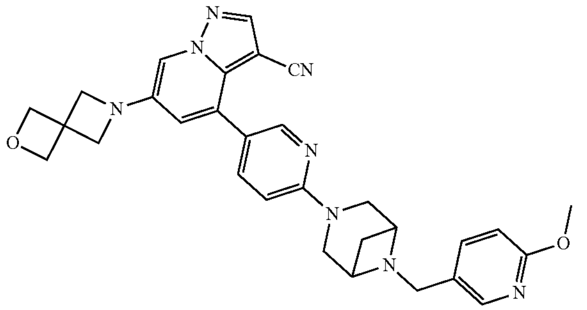 [SMILES: COc1ccc(CN2C3CC2CN(c2ccc(-c4cc(N5CC6(COC6)C5)cn5ncc(C#N)c45)cn2)C3)cn1]

To a flask charged with toluene (20 mL) were sequentially added Intermediate 5 (59 mg), 2-oxa-6-azaspiro[3.3]heptane (20 mg), tris(dibenzylideneacetone)dipalladium (9 mg), (±)-2,2'-Bis(diphenyl phosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=15:1 (V:V)) to obtain the target compound (25 mg).

$^1H$ NMR (400 MHz, $CDCl_3$) δ 8.37 (1H, d, J=2.8 Hz), 8.15 (1H, s), 8.10 (1H, d, J=2.0 Hz), 7.77 (1H, dd, J=8.8 Hz. 2.8 Hz), 7.61-7.74 (2H, m), 6.67-6.74 (3H, m), 4.87 (4H, s), 4.09 (4H, s), 3.92 (3H, s), 3.77-3.90 (4H, m), 3.55-3.70 (4H, m), 2.67-2.83 (11, m), 1.65-1.70 (1H, m).

Example 15: 6-(1-methyl-1Hpyrazol-4-yl)-4-(6-(4-(3-(methylsulfonyl)benzyl) piperazin-1-yl) pyridin-3-yl)pyrazolo[1,5-a]pyridine-3-carbonitrile

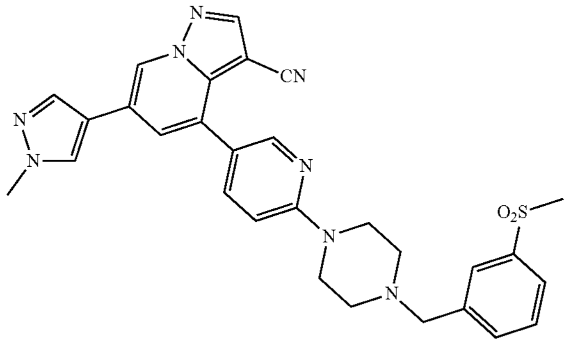

At 0° C., Intermediate 1 (39 mg) was dissolved in THF (10 mL), 3-(methylsulfonyl)benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (31 mg).

$^1H$ NMR (400 MHz, $CDCl_3$) δ 8.63 (1H, d, J=1.2 Hz), 8.36 (1H, d, J=2.8 Hz), 8.26 (1H, s), 7.97 (1H, s), 7.86 (1H, d, J=7.6 Hz), 7.78 (1H, s), 7.74 (1H, dd, J=8.8 Hz, 2.4 Hz), 7.69 (1H, d, J=7.6 Hz), 7.68 (1H, s), 7.56 (1H, t, J=7.6 Hz), 7.39 (1H, d, J=1.2 Hz), 6.77 (1H, d, J=8.8 Hz), 3.99 (3H, s), 3.65-3.69 (6H, m), 3.08 (3H, s), 2.58-2.60 (4H, m).

Example 16: 6-(1-methyl-1Hpyrazol-4-yl)-4-(6-(4-(4-(methylsulfonyl)benzyl) piperazin-1-yl) pyridin-3-yl)pyrazolo[1,5-a]pyridine-3-carbonitrile

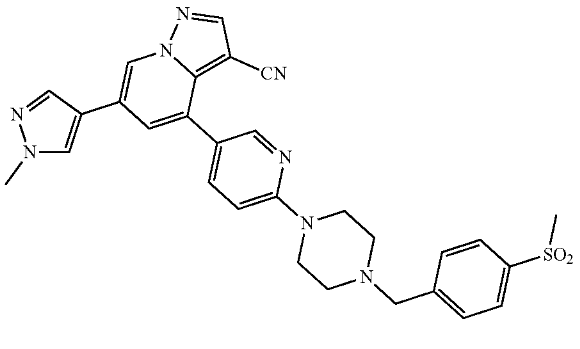

At 0° C., Intermediate 1 (39 mg) was dissolved in THF (10 mL), 4-(methylsulfonyl)benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (29 mg).

$^1H$ NMR (400 MHz, $CDCl_3$) δ 8.63 (1H, d, J=1.6 Hz), 8.36 (1H, d, J=2.8 Hz), 8.26 (1H, s), 7.92 (2H, d, J=8.4 Hz), 7.78 (1H, s), 7.75 (1H, dd, J=8.8 Hz, 2.4 Hz), 7.67 (1H, s), 7.60 (2H, d, J=8.0 Hz), 7.39 (0H, d, J=1.2 Hz), 6.78 (1H, d, J=8.8 Hz), 3.99 (3H, s), 3.63-3.71 (6H, m), 3.08 (3H, s), 2.56-2.62 (4H, m).

Example 17: 6-(1-methyl-1Hpyrazol-4-yl)-4-(6-(4-(4-(methylthio)benzyl)piperazin-1-yl) pyridin-3-yl) pyrazolo[1,5-a]pyridine-3-carbonitrile

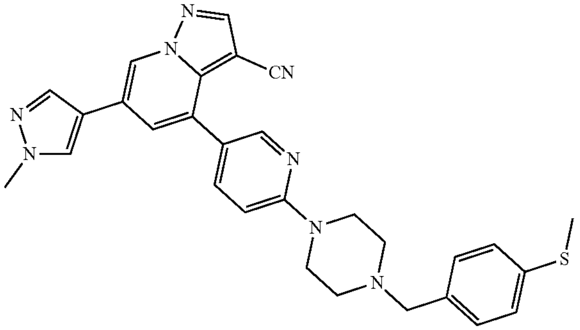

At 0° C., Intermediate 1 (39 mg) was dissolved in THF (10 mL). 4-(methylthio)benzaldehyde (30 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (23 mg).

$^1H$ NMR (400 MHz, $CDCl_3$) δ 8.62 (1H, d, J=1.2 Hz), 8.35 (1H, d, J=2.4 Hz), 8.25 (1H, s), 7.78 (1H, s), 7.73 (1H, dd, J=8.8 Hz 2.4 Hz), 7.67 (1H, s), 7.38 (1H, d, J=1.2 Hz), 7.29 (2H, d, J=8.4 Hz), 7.24 (2H, d, J=8.4 Hz), 6.76 (1H, d, J=8.4 Hz), 3.98 (3H, s), 3.63-3.71 (4H, m), 3.54 (2H, s), 2.54-2.62 (4H, m), 2.49 (3H, s).

Example 18: 6-(1-methyl-1Hpyrazol-4-yl)-4(6-(4-((6-(ethylthio)pyridin-3-yl) methyl) piperazin-1-yl) pyridin-3-yl)pyrazolo[1,5-a]pyridine-3-carbonitnile

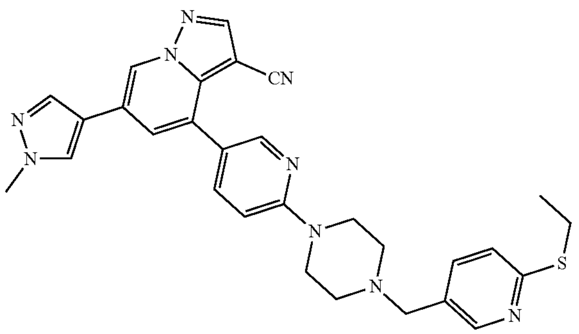 [SMILES: CCSc1ccc(CN2CCN(c3ccc(-c4cc(-c5cnn(C)c5)cn5ncc(C#N)c45)cn3)CC2)cn1]

At 0° C. Intermediate 1 (39 mg) was dissolved in THF (10 mL), 6-(ethylthio)nicotinaldehyde (34 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (26 mg).

$^1$H NMR (400 MHz, $CDCl_3$) δ 8.62 (1H, d, J=1.6 Hz), 8.38 (1H, d, J=2.0 Hz), 8.35 (1H, d, J=2.4 Hz), 8.25 (1H, s), 7.78 (1H, s), 7.73 (1H, dd, J=8.8 Hz. 2.4 Hz), 7.67 (1H, s), 7.50-7.56 (1H, m), 7.38 (1H, d, J=1.2 Hz), 7.16 (1H, d, J=8.4 Hz), 6.76 (1H, d, J=8.8 Hz), 3.98 (3H, s), 3.61-3.71 (4H, m), 3.51 (2H, s), 3.17 (2H, q, J=7.6 Hz), 2.52-2.60 (4H, m), 1.38 (3H, t, J=7.6 Hz).

Example 19: 6-(morpholino-1-yl)-4-(6-(4-((6-methoxypyridin-3-yl)methyl)piperazin-1-yl) pyridin-3-yl)pyrazolo[1,5-a]pyridine-3-carbonitrile

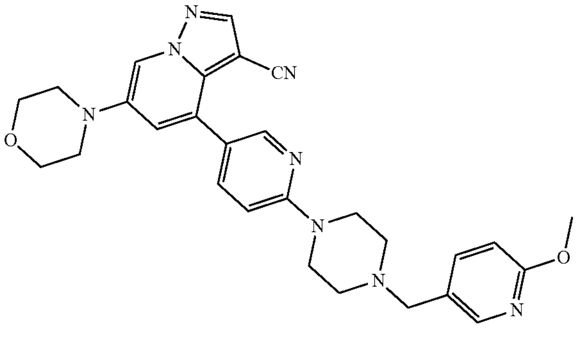 [SMILES: COc1ccc(CN2CCN(c3ccc(-c4cc(N5CCOCC5)cn5ncc(C#N)c45)cn3)CC2)cn1]

To a flask charged with toluene (20 mL) were sequentially added Intermediate 7 (57 mg), morpholine (17 mg), tris (dibenzylideneacetone)dipalladium (9 mg), (±)-2,2'-Bis(diphenyl phosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (15 mg).

$^1$H NMR (400 MHz, $CDCl_3$) δ 8.30 (1H, d, J=2.8 Hz), 8.17 (1H, s), 8.08 (1H, s), 7.99 (1H, d, J=2.0 Hz), 7.70 (1H, dd, J=8.8 Hz. 2.4 Hz), 7.57-7.69 (I H, m), 7.13 (1H, d, J=2.0 Hz), 6.73-6.76 (2H, m), 3.94 (3H, s), 3.88-3.90 (4H, m), 3.59-3.72 (4H, m), 3.42-3.58 (2H, m), 3.13-3.16 (4H, m), 2.49-2.65 (4H, m).

Example 20: 6-(1-methyl-1Hpyrazol-4-yl)-4-(6-(6-(3-(methylsulfonyl)benzyl)-3,6-diazabicyclo[3.1.1] heptan-3-yl)pyridin-3-yl)pyrazolo[1,5-a]pyridine-3-carbonitrile

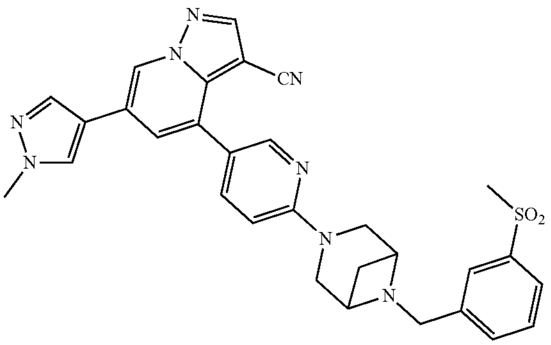 [SMILES: Cn1cc(-c2cc(-c3ccc(N4CC5CC(C4)N5Cc4cccc(S(C)(=O)=O)c4)nc3)c3c(C#N)cnn3c2)cn1]

At 0° C., Intermediate 2 (39 mg) was dissolved in THF (10 mL), 3-(methylsulfonyl)benzaldehyde (37 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (31 mg).

$^1$H NMR (400 MHz, $CDCl_3$) δ 8.64 (1H, d, J=1.2 Hz), 8.43 (1H, d, J=2.4 Hz), 8.27 (1H, s), 7.99 (1H, s), 7.79-7.84 (3H, m), 7.68-7.72 (2H, m), 7.52 (1H, t, J=7.6 Hz), 7.42 (1H, d, J=1.2 Hz), 6.71 (1H, d, J=8.8 Hz), 3.99 (3H, s), 3.81-3.91 (4H, m), 3.77 (2H, s), 3.62-3.70 (2H, m), 3.07 (3H, s), 2.77-2.84 (1H, m), 1.71 (1H, d, J=9.2 Hz).

Example 21: 6-(1-methyl-1Hpyrazol-4-yl)-4-(6-(4-(2-(methylthio)ethyl) piperazin-1-yl) pyridin-3-yl) pyrazolo[1,5-a]pyridine-3-carbonitrile

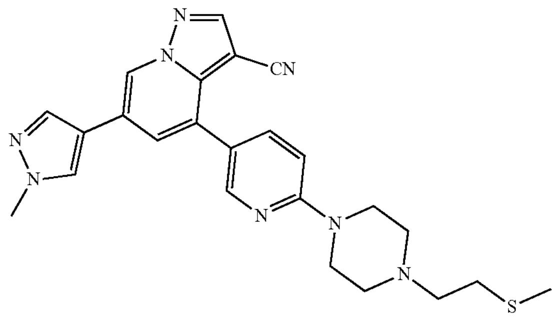

At 0° C., intermediate 1 (39 mg) was dissolved in THF (10 mL). 3-(methylthio) propanal (21 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 ng).

$^1$H NMR (400 MHz, $CDCl_3$) δ 8.63 (1H, d, J=1.2 Hz), 8.36 (1H, d, J=2.8 Hz), 8.26 (1H, s), 7.78 (1H, s), 7.75 (1H, dd, J=8.8 Hz, 2.8 Hz), 7.67 (1H, s), 7.39 (1H, d, J=1.2 Hz), 6.78 (1H, d, J=8.8 Hz), 3.99 (3H, s), 3.63-3.74 (4H, m), 2.56-2.74 (8H, m), 2.16 (3H, s).

Example 22: 6-(1-methyl-1Hpyrazol-4-yl)-4-(6-(6-((5-(methylthio)pyridin-2-yl) methyl)-3,6-diazabicyclo[3.1.1]heptan-3-yl)pyridin-3-yl)pyrazolo[1,5-a]pyridine-3-carbonitrile

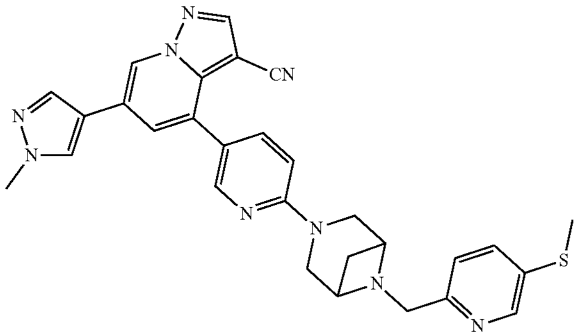

At 0° C., Intermediate 2 (40 mg) was dissolved in THF (10 mL), 5-(methylthio)picolinaldehyde (31 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1$H NMR (400 MHz, $CDCl_3$) δ 8.67 (1H, d, J=1.6 Hz), 8.45 (1H d, J=2.8 Hz), 8.43 (1H, d, J=2.4 Hz), 8.29 (1H, s), 7.86 (1H, dd, J=8.8 Hz, 2.4 Hz), 7.80 (1H, s), 7.76 (1H, dd, J=8.4 Hz. 2.4 Hz), 7.70 (1H, s), 7.42 (1H, d, J=1.6 Hz), 7.35 (1H, d, J=8.4 Hz), 6.75 (1H, d, J=8.8 Hz), 4.38 (2H, d, J=6.0 Hz), 3.98-4.01 (5H, m), 3.88-3.92 (4H, m), 3.25-3.31 (1H, m), 2.57 (3H, s), 1.86 (1H, d, J=6.0 Hz).

Example 23: 6-(1-methyl-1Hpyrazol-4-yl)-4-(6-(4-((6-(methylthio)pyridin-3-yl) methyl) piperazin-1-yl)pyridin-3-yl)pyrazolo[1,5-a]pyridine-3-carbonitrile

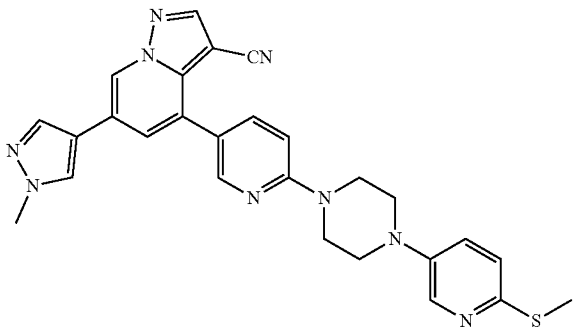 [SMILES: CSc1ccc(N2CCN(c3ccc(-c4cc(-c5cnn(C)c5)cn5ncc(C#N)c45)cn3)CC2)cn1]

At 0° C. Intermediate 1 (39 mg) was dissolved in THF (10 mL), 6-(methylthio)nicotinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (27 mg).

$^1$H NMR (400 MHz, $CDCl_3$) δ 8.64 (1H, d, J=1.2 Hz), 8.39 (1H, d, J=2.8 Hz), 8.27 (1H, s), 8.22 (1H, d, J=2.4 Hz), 7.77-7.80 (2H, m), 7.68 (1H, s), 7.40 (1H, d, J=1.6 Hz), 7.20 (1H, dd, J=8.8 Hz, 2.8 Hz), 7.13 (1H, d, J=8.8 Hz), 6.84 (1H, d, J=8.8 Hz), 3.99 (3H, s), 3.82-3.85 (4H, m), 3.27-3.30 (4H, m), 2.56 (3H, s).

Example 24: 6-(1-methyl-1Hpyrazol-4-yl)-4-(6-(4-(2-(methylsulfonyl)benzyl) piperazin-1-yl) pyridin-3-yl)pyrazolo[1,5-a]pyridine-3-carbonitrile

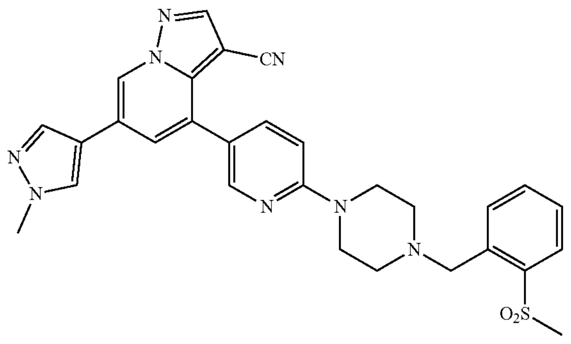 [SMILES: Cn1cc(-c2cc(-c3ccc(N4CCN(Cc5ccccc5S(C)(=O)=O)CC4)nc3)c3c(C#N)cnn3c2)cn1]

At 0° C., Intermediate 1 (39 mg) was dissolved in THF (10 mL), 2-(methylsulfonyl)benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified though Thin Layer Chromatography (developing solvent: dichloromethane:methanol=20:1 (V:V)) to obtain the title compound (34 mg).

$^{1}$H NMR (400 MHz, $CDCl_3$) δ 8.63 (1H, d, J=1.6 Hz), 8.36 (1H, d, J=2.8 Hz), 8.25 (1H, s), 8.14 (1H, d, J=8.0 Hz), 7.78 (1H, s), 7.74 (1H, dd, J=8.8 Hz, 2.4 Hz), 7.67 (1H, s), 7.60 (1H, t, J=7.2 Hz), 7.51 (1H, t, J=7.6 Hz), 7.45 (1H, d, J=7.2 Hz), 7.38 (1H, d, J=1.2 Hz), 6.77 (1H, d, J=9.2 Hz), 4.02 (2H, s), 3.99 (3H, s), 3.58-3.65 (4H, m), 3.46 (3H, s), 2.64-2.72 (4H, m).

Example 25: 6-(1-methyl-1Hpyrazol-4-yl)-4-(6-(6-(4-(methylsulfonyl)benzyl)-3,6-diazabicyclo[3.1.1] heptan-3-yl)pyridin-3-yl)pyrazolo[1,5-a]pyridine-3-carbonitrile

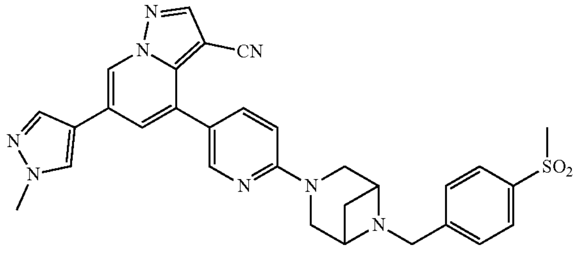 [SMILES: Cn1cc(-c2cc(-c3ccc(N4CC5CC(C4)N5Cc4ccc(S(C)(=O)=O)cc4)nc3)c3c(C#N)cnn3c2)cn1]

At 0° C., Intermediate 2 (39 mg) was dissolved in THF (10 mL), 4-(methylsulfonyl)benzaldehyde (37 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (30 mg).

$^{1}$H NMR (400 MHz, $CDCl_3$) δ 8.65 (1H, s), 8.44 (1H, d, J=2.8 Hz), 8.28 (1H, s), 7.90 (2H, d, J=8.4 Hz), 7.81 (1H, dd, J=8.8 Hz. 2.4 Hz), 7.80 (1H, s), 7.69 (1H, s), 7.59-7.65 (2H, m), 7.42 (1H, d, J=1.2 Hz), 6.71 (1H, d, J=8.4 Hz), 3.99 (3H, s), 3.55-3.95 (8H, m), 3.05 (3H, s), 2.66-2.86 (1H, m), 1.66-1.74 (1H, m).

Example 26: 6-(3,3-difluoroazetidin-1-yl)-4-(6-(4-((6-methoxypyridin-3-yl) methyl) piperazin-1-yl) pyridin-3-yl)pyrazolo[1,5-a]pyridine-3-carbonitrile

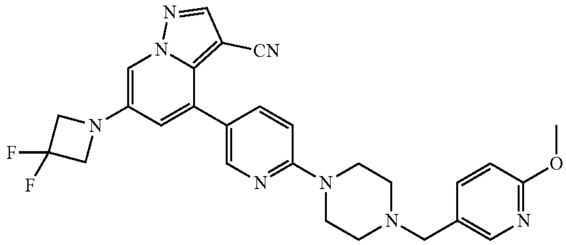 [SMILES: COc1ccc(CN2CCN(c3ccc(-c4cc(N5CC(F)(F)C5)cn5ncc(C#N)c45)cn3)CC2)cn1]

To a flask charged with toluene (20 mL) were sequentially added Intermediate 7 (57 mg). 3,3-difluoroazetidine hydrochloride (26 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane: methanol=20:1 (V:V)) to obtain the target compound (14 mg).

$^{1}$H NMR (400 MHz, $CDCl_3$) δ 8.30 (1H, d, J=2.0 Hz), 8.17 (1H, s), 8.08 (1H, d, J=2.0 Hz), 7.76 (1H, d, J=2.0 Hz), 7.70 (1H, dd, J=9.2 Hz. 2.4 Hz), 7.59-7.65 (1H, m), 6.70-6.76 (3H, m), 4.30 (4H, t, J=11.6 Hz), 3.94 (3H, s), 3.60-3.71 (4H, m), 3.50 (2H, s), 2.50-2.62 (4H, m).

Example 27: 6-(3-methoxy azetidin-1-yl)-4-(6-(6-((6-methoxy pyridin-3-yl) methyl)-3,6-diazabicyclo [3.1.1]heptan-3-yl)pyridin-3-yl)pyrazolo[1,5-a]pyridine-3-carbonitrile

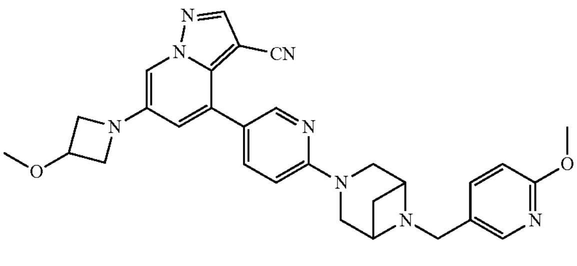

To a flask charged with toluene (20 mL) were sequentially added Intermediate 5 (59 mg), 3-methoxyazetidine (18 mg), tris(dibenzylideneacetone)dipalladium (9 mg). (±)-2,2'-Bis (diphenyl phosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (10 mg).

$^1$H NMR (400 MHz, $CDCl_3$) δ 8.39 (1H, s), 8.11-8.15 (2H, m), 7.81 (1H, d, J=7.6 Hz), 7.66-7.75 (2H, m), 6.78 (1H, d, J=7.6 Hz), 6.74 (1H, d, J=2.0 Hz), 6.71 (1H, d, J=8.8 Hz), 4.37-4.43 (1H, m). 4.17 (2H, t, J=6.8 Hz), 3.62-4.05 (13H, m), 3.36 (3H, s), 2.53-2.66 (1H, m), 1.76-1.84 (1H, m).

Example 28: 6-(3-hydroxy-3-(trifluoromethyl)azetidin-1-yl)-4-(6-(6-((6-methoxy pyridin-3-yl) methyl)-3,6-diazabicyclo[3.1.1]heptan-3-yl)pyridin-3-yl) pyrazolo[1,5-a]pyridine-3-carbonitrile

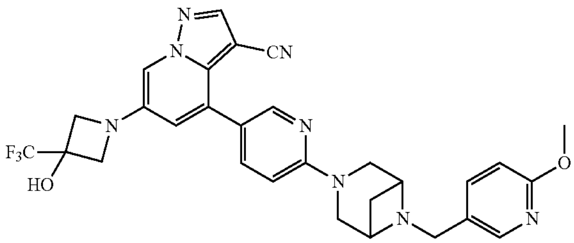 [SMILES: COc1ccc(CN2C3CC2CN(c2ccc(-c4cc(N5CC(O)(C(F)(F)F)C5)cn5ncc(C#N)c45)cn2)C3)cn1]

To a flask charged with toluene (20 mL) were sequentially added Intermediate 5 (59 ng). 3-(trifluoromethyl)azetidin-3-ol hydrochloride (35 mg), tris(dibenzylideneacetone) dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (17 mg).

$^1$H NMR (400 MHz, $CDCl_3$) δ 8.37 (1H, d, J=2.4 Hz), 8.16 (1H, s), 8.10 (1H, s), 7.65-7.79 (3H, in). 6.67-6.74 (3H, m), 4.28 (2H, d, J=8.4 Hz), 3.97 (2H, d, J=8.4 Hz), 3.78-3.94 (7H, m), 3.54-3.72 (4H, m), 2.66-2.86 (1H, m), 1.65-1.72 (1H, m).

Example 29: 6-(2-hydroxy-2-methylpropoxy) 4-(6-(4-(4-(methylsulfonyl)benzyl) piperazin-1-yl) pyridin-3-yl)pyrazolo[1,5-α]pyridin-3-carbonitrile

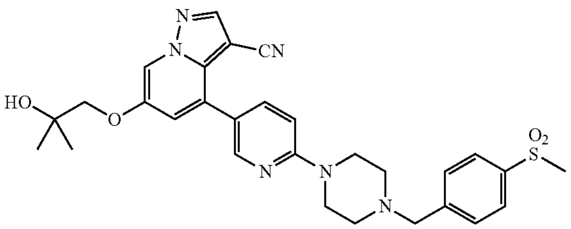 [SMILES: CC(C)(O)COc1cc(-c2ccc(N3CCN(Cc4ccc(S(C)(=O)=O)cc4)CC3)nc2)c2c(C#N)cnn2c1]

At 0° C., 6-hydroxy-4-(6-(4-(4-(methylsulfonyl)benzyl) piperazin-1-yl)pyridin-3-yl) pyrazolo[1,5-a]pyridine-3-carbonitrile (49 mg) was dissolved in dioxane (10 mL). 2,2-dimethyloxirane (1 ml) and potassium carbonate (50 mg) were sequentially added, the mixture was heated in a sealed tube to 60° C. and stirred for 12 hours. The reaction solution was cooled and poured into water, the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (13 mg).

$^1$H NMR (400 MHz, $CDCl_3$) δ 8.33 (1H, d, J=2.8 Hz), 8.19 (1H, s), 8.13 (1H, d, J=2.4 Hz), 7.92 (2H d, J=8.0 Hz), 7.70 (1H, dd, J=9.2 Hz. 2.8 Hz), 7.59 (2H, d, J=8.4 Hz), 7.13 (1H, d, J=2.0 Hz), 6.75 (1H, d, J=8.4 Hz), 3.85 (2H, s), 3.64-3.68 (6H, m), 3.07 (3H, s), 2.56-2.59 (4H, m), 2.05 (1H, s), 1.38 (6H, s).

Example 30: 4-(6-(6-((6-methoxypyridin-3-yl) methyl)-3,6-diazabicyclo[3.1.1] heptan-3-yl) pyridin-3-yl)-6-(7-oxa-2-azaspiro[3.5] nonan-2-yl) pyrazolo[1,5-a]pyridine-3-carbonitrile

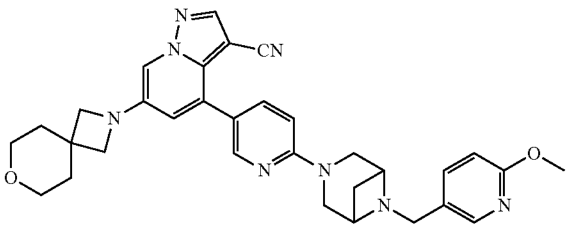 [SMILES: COc1ccc(CN2C3CC2CN(c2ccc(-c4cc(N5CC6(CCOCC6)C5)cn5ncc(C#N)c45)cn2)C3)cn1]

To a flask charged with toluene (20 mL) were sequentially added Intermediate 5 (59 mg). 7-oxa-2-azaspiro[3.5] nonane hydrochloride (33 mg), tris(dibenzylideneacetone) dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane: methanol=20:1 (V:V)) to obtain the target compound (19 mg).

$^1$H NMR (400 MHz, $CDCl_3$) δ 8.38 (1H, d, J=2.8 Hz), 8.14 (1H, s), 8.12 (1H, s), 7.73-7.94 (2H, in). 7.70 (1H, d, J=2.0 Hz), 6.73-6.76 (2H, m), 6.69 (1H d, J=8.8 Hz), 3.42-4.15 (19H, m), 2.70-3.10 (1H, m), 1.86-1.89 (4H, m), 1.70-1.78 (1H, m).

Example 31: 6-(1-methyl-1Hpyrazol-4-yl)-4(6-(6-(4-(methylthio)benzyl)-3,6-diazabicyclo[3.1.1]heptan-3-yl)pyridin-3-yl)pyrazolo[1,5-a]pyridine-3-carbonitrile

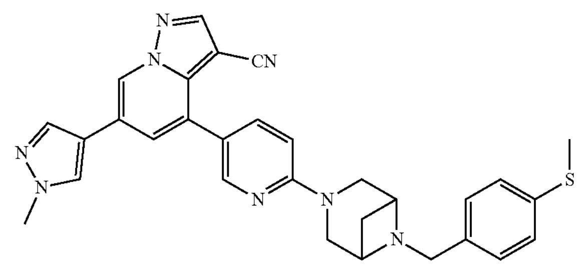 [SMILES: CSc1ccc(CN2C3CC2CN(c2ccc(-c4cc(-c5cnn(C)c5)cn5ncc(C#N)c45)cn2)C3)cc1]

At 0° C., Intermediate 2 (39 mg) was dissolved in THF (10 mL). 4-(methylthio)benzaldehyde (37 mug) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (32 mg).

$^1$H NMR (400 MHz, $CDCl_3$) δ 8.66 (1H, d, J=1.2 Hz), 8.46 (1H, s), 8.28 (1H, s), 7.87 (1H, d, J=9.2 Hz), 7.80 (1H, s), 7.70 (1H, s), 7.56-7.64 (2H, m), 7.43 (1H, d, J=1.2 Hz), 7.25-7.27 (2H, m), 6.74 (1H, d, J=9.2 Hz), 4.37-4.55 (2H, m), 3.86-4.11 (9H, m), 3.35-3.61 (1H, m), 2.48 (3H, s), 1.64-1.68 (1H, m).

Example 32: 6-(3-cyanoazetidin-1-yl)-4-(6-(4-((6-methoxypyridin-3-yl)methyl) piperazin-1-yl) pyridin-3-yl)pyrazolo[1,5-a]pyridine-3-carbonitrile

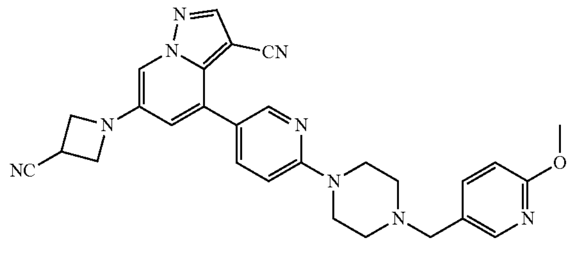 [SMILES: COc1ccc(CN2CCN(c3ccc(-c4cc(N5CC(C#N)C5)cn5ncc(C#N)c45)cn3)CC2)cn1]

To a flask charged with toluene (20 mL) were sequentially added Intermediate 7 (57 mg). 3-cyano azetidine hydrochloride (24 mg), tris(dibenzylideneacetone)dipalladium (9 mg), (±)-2,2'-Bis(diphenyl phosphino)-1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (12 mg).

$^1$H NMR (400 MHz, $CDCl_3$) δ 8.39 (1H, s), 8.15 (1H, s), 8.12 (1H, s), 7.80 (1H, d, J=9.2 Hz), 7.70 (1H, s), 7.26 (1H, s), 6.74-6.81 (2H, m), 6.70 (1H, d, J=9.2 Hz), 3.51-4.09 (14H, m), 1.78-1.90 (4H, m).

Example 33: 6-(3-methoxyazetidin-1-yl)-4-(6-(4-((6-methoxypyridin-3-yl)methyl) piperazin-1-yl) pyridin-3-yl)pyrazolo[1,5-a]pyridine-3-carbonitrile

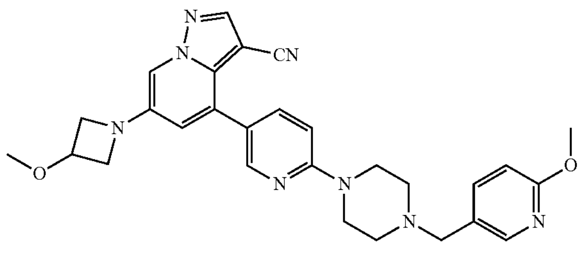

To a flask charged with toluene (20 mL) were sequentially added Intermediate 7 (57 mg). 3-methoxy azetidine (18 mg), tris(dibenzylideneacetone)dipalladium (9 mg), (±)-2,2'-Bis (diphenyl phosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane: methanol=20:1 (V:V)) to obtain the target compound (12 mg).

$^1$H NMR (400 MHz, $CDCl_3$) δ 8.29 (1H, d, J=2.4 Hz), 8.12 (1H, s), 8.08 (1H, s), 7.68-7.72 (2H, m), 7.58-7.67 (1H, m), 6.73-6.77 (2H, m), 6.70 (1H, d, J=2.0 Hz), 4.35-4.41 (1H, m), 4.15 (2H, t, J=6.8 Hz), 3.94 (3H, s), 3.75 (2H, dd, J=8.0 Hz. 4.8 Hz), 3.58-3.70 (4H, m), 3.44-3.57 (2H, m), 3.35 (3H, s), 2.48-2.66 (4H, m).

Example 34: 6-(3-hydroxy-3-methylazetidin-1-yl)-4-(6-(4-((6-methoxypyridin-3-yl) methyl) piperazin-1-yl)pyridin-3-yl)pyrazolo[1,5-a]pyridine-3-carbonitrile

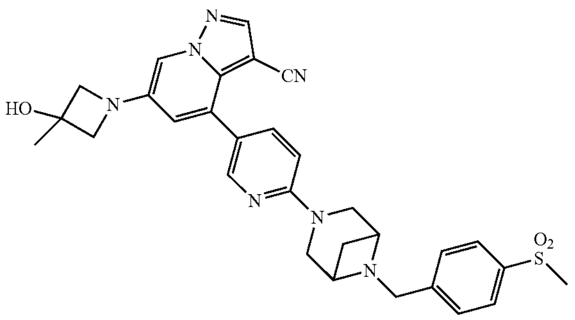 [SMILES: CC1(O)CN(c2cc(-c3ccc(N4CC5CC(C4)N5Cc4ccc(S(C)(=O)=O)cc4)nc3)c3c(C#N)cnn3c2)C1]

To a flask charged with toluene (20 mL) were sequentially added Intermediate 6 (64 mg). 3-methylazetidin-3-ol hydrochloride (27 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (19 ng).

$^1$H NMR (400 MHz, $CDCl_3$) δ 8.37 (1H, d, J=2.4 Hz), 8.15 (1H, s), 7.89 (2H, d, J=8.8 Hz), 7.78 (1H, dd, J=8.8 Hz, 2.6 Hz), 7.72 (1H d, J=2.0 Hz), 7.58-7.64 (2H, m), 6.73 (1H, d, J=2.0 Hz), 6.68 (1H, d, J=8.8 Hz), 3.91 (2H, d, J=8.0 Hz), 3.70-3.88 (8H, m), 3.56-3.68 (2H, m), 3.04 (3H, s), 2.68-2.84 (1H, m), 2.08 (1H, s), 1.64-1.72 (4H, m).

Example 35: 6-(3-cyanoazetidin-1-yl)-4-(6-(6-(4-(methylsulfonyl)benzyl)-3,6-diazabicyclo[3.1.1]heptan-3-yl)pyridin-3-yl)pyrazolo[1,5-a]pyridine-3-carbonitrile

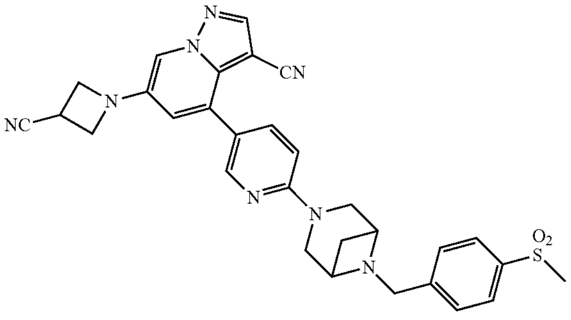 [SMILES: CS(=O)(=O)c1ccc(CN2C3CC2CN(c2ccc(-c4cc(N5CC(C#N)C5)cn5ncc(C#N)c45)cn2)C3)cc1]

To a flask charged with toluene (20 mL) were sequentially added Intermediate 6 (64 mg), 3-cyano azetidine hydrochloride (24 mg), tris(dibenzylideneacetone)dipalladium (9 mg). (±)-2,2'-Bis(diphenyl phosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (22 mg).

$^1$H NMR (400 MHz, $CDCl_3$)$^6$ 8.37 (1H, d, J=2.4 Hz), 8.19 (1H, s), 7.89 (2H, d, J=7.6 Hz), 7.78 (1H, dd, J=9.2 Hz. 2.8 Hz), 7.74 (1H, d, J=1.6 Hz), 7.55-7.66 (2H, m), 6.68-6.70 (2H, m), 4.26 (2H, t, J=7.6 Hz), 4.15 (2H, t, J=6.8 Hz), 3.49-3.92 (9H, m), 3.05 (3H, s), 2.68-2.84 (1H, m), 1.66-1.72 (1H, m).

Example 36: 6-(3,3-difluoroazetidin-1-yl)-4-(6-(6-(4-(methylsulfonyl)benzyl)-3,6-diazabicyclo [3.1.1]heptan-3-yl)pyridin-3-yl)pyrazolo[1,5-a]pyridine-3-carbonitrile

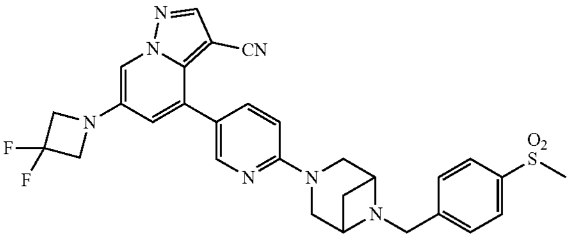 [SMILES: CS(=O)(=O)c1ccc(CN2C3CC2CN(c2ccc(-c4cc(N5CC(F)(F)C5)cn5ncc(C#N)c45)cn2)C3)cc1]

To a flask charged with toluene (20 mL) were sequentially added Intermediate 6 (64 mg). 3,3-difluoroazetidine hydrochloride (26 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (24 mg).

$^1$H NMR (400 MHz, $CDCl_3$) δ 8.38 (1H, d, J=2.4 Hz), 8.19 (1H s), 7.89 (2H, d, J=8.0 Hz), 7.77-7.80 (2H, m), 7.60 (2H, d, J=8.0 Hz), 6.73 (1H, d, J=2.0 Hz), 6.69 (1H, d, J=8.8 Hz), 4.31 (4H, t, J=11.6 Hz), 3.70-3.88 (6H, m), 3.56-3.67 (2H, m), 3.04 (3H, s), 2.68-2.82 (1H, m), 1.68 (1H, d, J=7.6 Hz).

Example 37: 6-(3-(dimethylamino)pyrrolidin-1-yl)-4-(6-(4-((6-methoxypyridin-3-yl)methyl) piperazin-1-yl)pyridin-3-yl)pyrazolo[1,5-a]pyridine-3-carbonitrile

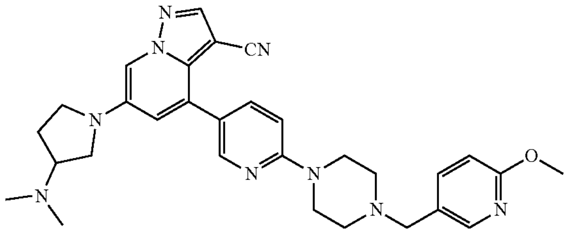

To a flask charged with toluene (20 mL) were sequentially added Intermediate 7 (57 mg), N,N-dimethylpyrrolidin-3-amine (23 mg), tris(dibenzylideneacetone)dipalladium (9 mg). (±)-2,2'-Bis (diphenylphosphino)-1,1'-binaphthalene (12 mg) and cesium carbonate (65 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (12 mg).

$^1$H NMR (400 MHz, $CDCl_3$) δ 8.32 (1H, d, J=2.4 Hz), 8.10 (1H, s), 8.07 (1H, s), 7.71-7.74 (2H, m), 7.61 (1H, dd, J=8.0 Hz, 2.0 Hz), 6.88 (1H, s), 6.72-6.76 (2H, m), 3.93 (3H, s), 3.61-3.66 (4H, m), 3.41-3.51 (4H, m), 3.31-3.38 (1H, m), 3.20 (1H, t, J=8.0 Hz), 2.87-2.96 (1H, m), 2.52-2.58 (4H, m), 2.32 (6H, s), 2.21-2.30 (1H, m), 1.96-2.04 (1H, m).

Example 38: 6-(2-hydroxy-2-methylpropoxy)-4-(6-(6-(4-(methylsulfonyl) benzyl)-3,6-diaza bicyclo [3.1.1]heptan-3-yl)pyridin-3-yl)pyrazolo[1,5-a]pyridine-3-carbonitrile

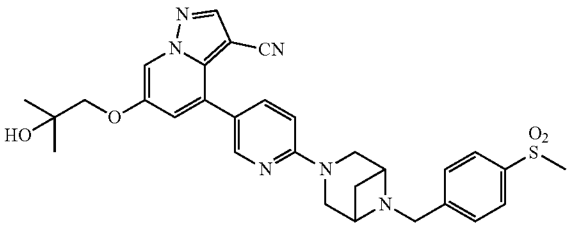 [SMILES: CC(C)(O)COc1cc(-c2ccc(N3CC4CC(C3)N4Cc3ccc(S(C)(=O)=O)cc3)nc2)c2c(C#N)cnn2c1]

At 0° C. 6-hydroxy-4-(6-(6-(4-(methylsulfonyl)benzyl)-3,6-diazabicyclo[3.1.1]heptan-3-yl) pyridin-3-yl)pyrazolo [1,5-a]pyridine-3-carbonitrile (50 mg) was dissolved in dioxane (10 mL). 2,2-dimethyloxirane (1 ml) and potassium carbonate (50 mg) were sequentially added, and the mixture was heated in a scaled tube to 60° C. and stirred for 12 hours. The reaction solution was cooled and poured into water, the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane: methanol=15:1 (V:V)) to obtain the title compound (14 mg).

$^1$H NMR (400 MHz, $CDCl_3$) δ 8.40 (1H, d, J=2.8 Hz), 8.22 (1H, s), 8.16 (1H, d, J=2.0 Hz), 7.89 (2H, d, J=8.0 Hz), 7.78 (1H, dd, J=8.8 Hz, 2.4 Hz), 7.61 (2H, d, J=8.0 Hz), 7.16 (1H, d, J=2.4 Hz), 6.69 (1H, d, J=8.4 Hz), 3.72-3.87 (8H, m), 3.57-3.70 (2H, m), 3.05 (3H, s), 2.69-2.84 (1H, m), 1.99-2.09 (1H, bis), 1.70 (1H, d, J=8.4 Hz), 1.40 (6H, s).

Example 39: 6-(3,3-difluoropyrrolidin-1-yl)-4-(6-(4-(4-(methylsulfonyl)benzyl) piperazin-1-yl) pyridin-3-yl)pyrazolo[1,5-u]pyridin-3-carbonitrile

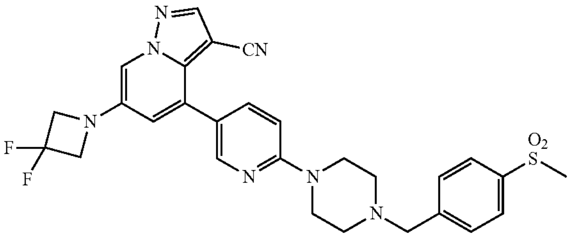 [SMILES: CS(=O)(=O)c1ccc(CN2CCN(c3ccc(-c4cc(N5CC(F)(F)C5)cn5ncc(C#N)c45)cn3)CC2)cc1]

To a flask charged with toluene (20 mL) were sequentially added Intermediate 8 (62 mg), 3,3-difluoroazetidine hydrochloride (26 mg), tris(dibenzylideneacetone)dipalladium (9 mg), (±)-2,2'-Bis (diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (16 mg).

$^1$H NMR (400 MHz, $CDCl_3$) δ 8.30 (1H, d, J=2.4 Hz), 8.17 (1H, s), 7.92 (2H, d, J=8.0 Hz), 7.76 (1H, d, J=2.0 Hz), 7.70 (1H, dd, J=9.2 Hz, 2.8 Hz), 7.60 (2H, d, J=8.0 Hz), 6.75 (1H, d, J=8.8 Hz), 6.71 (1H, d, J=2.0 Hz), 4.29 (4H, t, J=11.6 Hz), 3.62-3.70 (6H, m), 3.07 (3H, s), 2.56-2.61 (4H, m).

Example 40: 6-(3-cyanoazetidin-1-yl)-4-(6-(4-(4-(methylsulfonyl)benzyl) piperazin-1-yl) pyridin-3-yl)pyrazolo[1,5-α]pyridin-3-carbonitrile

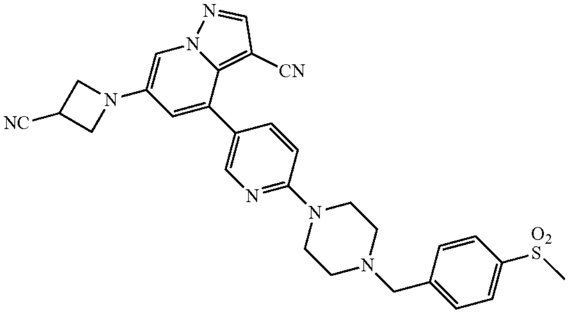 [SMILES: CS(=O)(=O)c1ccc(CN2CCN(c3ccc(-c4cc(N5CC(C#N)C5)cn5ncc(C#N)c45)cn3)CC2)cc1]

To a flask charged with toluene (20 mL) were sequentially added Intermediate 8 (62 mg). 3-cyano azetidine hydrochloride (24 mg), tris(dibenzylideneacetone)dipalladium (9 mg), (±)-2,2'-Bis(diphenyl phosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (18 mg).

$^1$H NMR (400 MHz, $CDCl_3$) δ 8.29 (1H, d, J=2.4 Hz), 8.16 (1H, s), 7.92 (2H, d, J=8.0 Hz), 7.72 (1 H, d, J=2.0 Hz), 7.70 (1H, dd, J=8.8 Hz, 2.0 Hz), 7.60 (2H, d, J=8.0 Hz), 6.75 (1H, d, J=8.8 Hz), 6.67 (1H, d, J=2.0 Hz), 4.25 (2H, dd, J=8.0 Hz, 6.8 Hz), 4.14 (2H, t. J=6.8 Hz), 3.62-3.72 (7H, m), 3.07 (3H, s), 2.54-2.63 (4H, m).

Example 41: 6-(1-methyl-1Hpyrazol-4-yl)-4-(5-(6-(4-(methylsulfonyl)benzyl)-3,6-diazabicyclo[3.1.1]heptan-3-yl)pyrazin-2-yl)pyrazolo[1,5-a]pyridine-3-carbonitrile

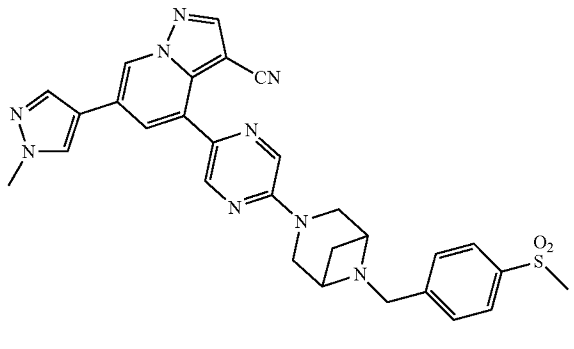

At 0° C. Intermediate 4 (40 mg) was dissolved in THF (10 mL). 4-(methylsulfonyl)benzaldehyde (27 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (30 mg).

$^1$H NMR (400 MHz, $CDCl_3$) δ 8.67 (1H, d, J=1.6 Hz), 8.55 (1H, d, J=1.2 Hz), 8.31 (1H, s), 8.27 (1H, d, J=1.2 Hz), 7.89 (2H, d, J=8.4 Hz), 7.81 (1H, s), 7.71 (1H, s), 7.65 (1H, d, J=1.2 Hz), 7.60 (2H, d, J=8.4 Hz), 3.99 (3H, s), 3.84-3.87 (4H, m), 3.75 (2H, s), 3.67 (2H, d, J=11.6 Hz), 3.05 (3H, s), 2.76-2.83 (1H, m), 1.70 (0H, d, J=9.2 Hz).

Example 42: 6-(1-methyl-1Hpyrazol-4-yl)-4-(5-(4-(4-(methylsulfonyl)benzyl) piperazin-1-yl) pyrazin-2-yl)pyrazolo[1,5-a]pyridine-3-carbonitrile

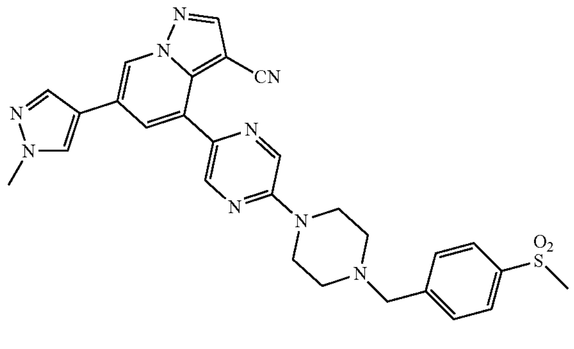

At 0° C., Intermediate 3 (39 mg) was dissolved in THF (10 mL), 4-(methyl sulfonyl) benzaldehyde (27 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1$H NMR (400 MHz, $CDCl_3$) δ 8.65 (1H, d, J=1.6 Hz), 8.47 (1H, d, J=1.6 Hz), 8.31 (1H, d, J=1.2 Hz), 8.30 (1H, s), 7.93 (2H, d, J=8.0 Hz), 7.80 (1H, s), 7.69 (I H, s), 7.63 (1H, d, J=1.6 Hz), 7.60 (2H, d, J=8.4 Hz), 3.99 (3H, s), 3.73-3.76 (4H, m), 3.66 (2H, s), 3.07 (3H, s), 2.59-2.61 (4H, m).

Example 43: 6-(1-methyl-1Hpyrazol-4-yl)-4-(6-(6-(2-(methylsulfonyl)benzyl)-3,6-diazabicyclo[3.1.1]heptan-3-yl)pyridin-3-yl)pyrazolo[1,5a]pyridine-3-carbonitrile

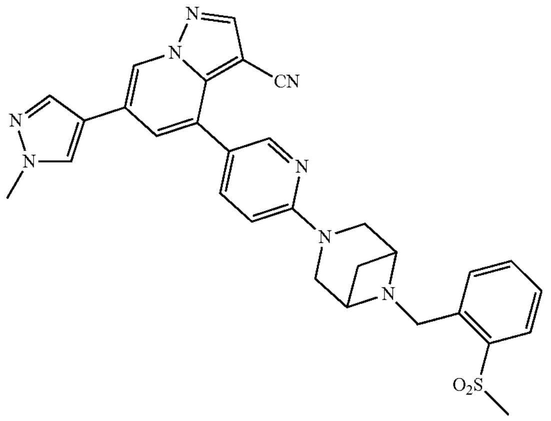 [SMILES: Cn1cc(-c2cc(-c3ccc(N4CC5CC(C4)N5Cc4ccccc4S(C)(=O)=O)nc3)c3c(C#N)cnn3c2)cn1]

At 0° C. Intermediate 2 (39 mg) was dissolved in THF (10 mL), 2-(methylsulfonyl)benzaldehyde (37 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (20 mg).

$^1$H NMR (400 MHz, $CDCl_3$) δ 8.65 (1H, s), 8.45 (1H, d, J=1.6 Hz), 8.28 (1H, s), 8.10 (1H, d, J=8.0 Hz), 7.80-7.84 (2H, m), 7.70 (1H, s), 7.57 (1H, t, J=7.6 Hz), 7.44-7.51 (2H, m), 7.43 (1H, s), 6.75 (1H, d, J=9.2 Hz), 4.11 (2H, s), 4.00 (3H, s), 3.95 (2H, d, J=12.4 Hz), 3.79-3.84 (2H, m), 3.62-3.69 (2H, m), 3.37 (3H, s), 2.57-2.64 (11, m), 1.69 (1H, d, J=8.4 Hz).

Example 44: 6-(1-ethyl-1Hpyrazol-4-yl)-4-(6-(6-(4-(methylsulfonyl)benzyl)-3,6-diazabicyclo[3.1.1] heptan-3-yl)pyridin-3 yl)pyrazolo[1,5-a]pyridine-3-carbonitrile

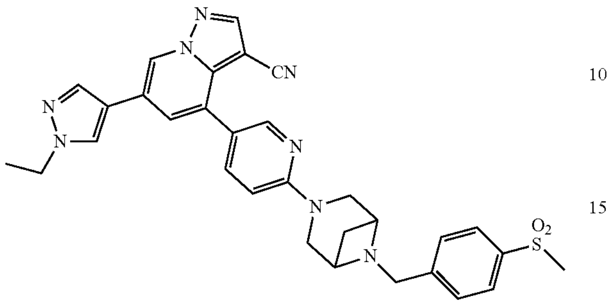

To a flask charged with dioxane and water (20 mL, volume ratio 5:1) were sequentially added Intermediate 6 (64 mg). (1-ethyl-1H-pyrazol-4-yl)boronic acid (21 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the target compound (34 mg).

$^1$H NMR (400 MHz, $CDCl_3$) δ 8.66 (1H, d, J=1.2 Hz), 8.44 (1H, d, J=2.0 Hz), 8.28 (1H, s), 7.90 (2H, d, J=8.4 Hz), 7.81-7.84 (2H, m), 7.72 (1H, s), 7.63 (2H, d, J=8.4 Hz), 7.73 (1H, d, J=1.2 Hz), 6.72 (1H, d, J=8.4 Hz), 4.26 (2H, q, J=7.2 Hz), 3.82-3.86 (4H, m), 3.78 (2H, s), 3.62-3.69 (2H, m), 3.05 (3H, s), 2.78-2.86 (OH, m), 1.71 (1H, d, J=8.8 Hz), 1.57 (3H, t, J=7.2 Hz).

Example 45: 6-(1-difluoromethyl-1Hpyrazol-4-yl)-4-(6-(6-(4-(methylsulfonyl) benzyl)-3,6-diazabicyclo[3.1.1] heptan-3-yl) pyridin-3-yl) pyrazolo[1,5-a] pyridine-3-carbonitrile

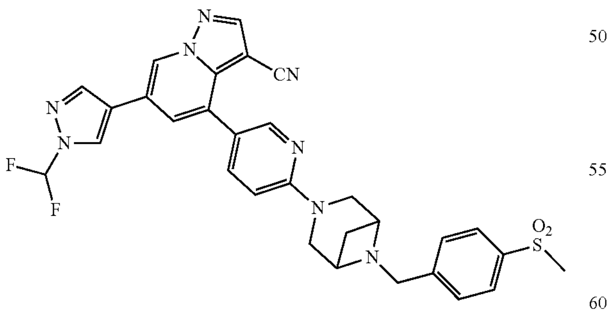

To a flask charged with dioxane and water (20 mL, volume ratio 5:1) were sequentially added Intermediate 6 (64 mg), (1-(difluoromethyl)-1H-pyrazol-4-yl)boronic acid (23 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (27 mg).

$^1$H NMR (400 MHz, $CDCl_3$) δ 8.72 (1H, s), 8.44 (1H, d, J=2.4 Hz), 8.32 (1H, s), 8.14 (1H, s), 7.98 (1H, s), 7.89 (2H, d, J=8.4 Hz), 7.82 (1H, dd, J=8.8 Hz, 2.4 Hz), 7.62 (2H, d, J=8.0 Hz), 7.73 (1H, s), 7.26 (1H, t, J=60.8 Hz), 6.72 (1H, d, J=8.8 Hz), 3.81-3.88 (4H, m), 3.76 (2H, s), 3.59-3.68 (2H, m), 3.06 (3H, s), 2.74-2.80 (1H, m), 1.70 (1H, d, J=9.2 Hz).

Example 46: 6-(3,3-difluoroazetidin-1-yl)-4-(6-(6-((5-methoxypyridin-2-yl) methyl)-3,6-diazabicyclo [3.1.1]heptan-3-yl) pyridin-3-yl) pyrazolo[1,5-a] pyridine-3-carbonitrile

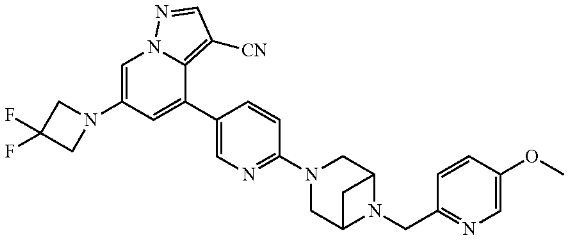 [SMILES: COc1ccc(CN2C3CC2CN(c2ccc(-c4cc(N5CC(F)(F)C5)cn5ncc(C#N)c45)cn2)C3)nc1]

To a flask charged with toluene (20 mL) were sequentially added Intermediate 17 (59 mg), 3,3-difluoroazetidine hydrochloride (26 mg), tris(dibenzylideneacetone)dipalladium (9 mg), (±)-2,2'-Bis (diphenyl phosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=15:1 (V:V)) to obtain the target compound (24 mg).

$^1$H NMR (400 MHz, DMSO-$d_6$) δ 8.52 (1H, s), 8.39 (1H, d, J=2.0 Hz), 8.27 (1H, d, J=2.0 Hz), 8.18 (1H, s), 7.82 (1H, dd, J=9.2 Hz, 2.4 Hz), 7.36-7.45 (2H, m), 7.08 (1H, d, J=1.6 Hz), 6.77 (1H, d, J=9.2 Hz), 4.38 (4H, t, J=8.0 Hz), 3.74-3.83 (7H, m), 3.50-3.68 (4H, m), 2.54-2.64 (I H, m), 1.59-1.64 (1H, m).

Example 47: 6-(1-difluoromethyl-1Hpyrazol-4 yl)-4-(6-(4-(3-(methylsulfonyl) benzyl) piperazin-1-yl) pyridin-3-yl)pyrazolo[1,5-a]pyridine-3-carbonitrile

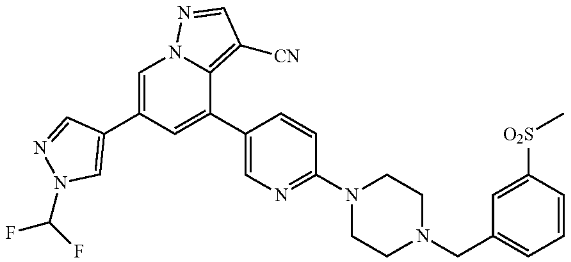 [SMILES: CS(=O)(=O)c1cccc(CN2CCN(c3ccc(-c4cc(-c5cnn(C(F)F)c5)cn5ncc(C#N)c45)cn3)CC2)c1]

To a flask charged with dioxane and water (20 mL, volume ratio 5:1) were sequentially added Intermediate 10 (62 mg), (1-(difluoromethyl)-1H-pyrazol-4-yl)boronic acid (23 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (31 mg).

$^1$H NMR (400 MHz, $CDCl_3$) δ 8.70 (1H, s), 8.37 (1H, d, J=2.4 Hz), 8.30 (1H, s), 1.13 (1H, s), 7.96-7.99 (2H, m), 7.87 (1H, d, J=8.0 Hz), 7.69-7.76 (2H, m), 7.56 (1H, s), 7.41 (I H, s), 7.25 (1H, t, J=60.8 Hz), 6.78 (1H, d, J=9.2 Hz), 3.64-3.72 (6H, m), 3.09 (3H, s), 2.58-2.63 (4H, m).

Example 48: 6-(1-difluoromethyl-1Hpyrazol-4-yl)-4-(6-(4-(2-(methylsulfonyl) benzyl) piperazin-1-yl) pyridin-3-yl)pyrazolo[1,5-a]pyridine-3-carbonitrile

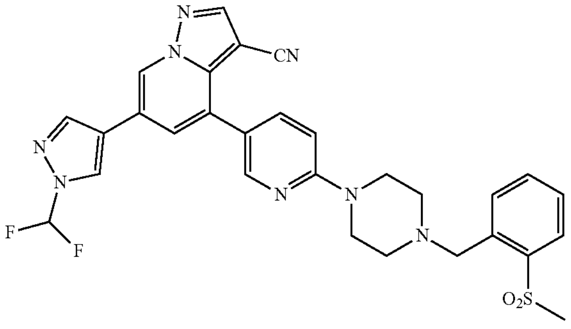 [SMILES: CS(=O)(=O)c1ccccc1CN1CCN(c2ccc(-c3cc(-c4cnn(C(F)F)c4)cn4ncc(C#N)c34)cn2)CC1]

To a flask charged with dioxane and water (20 mL, volume ratio 5:1) were sequentially added Intermediate 18 (62 mg), (1-(difluoromethyl)-1H-pyrazol-4-yl)boronic acid (23 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (32 mg).

$^1$H NMR (400 MHz, $CDCl_3$) δ 8.71 (1H, s), 8.38 (1H, d, J=2.4 Hz), 8.30 (1H, s), 8.13-8.16 (2H, in). 7.97 (1H, s), 7.75 (1H, dd, J=8.8 Hz, 2.4 Hz), 7.61 (1H, t, J=7.6 Hz), 7.53 (1H, t, J=7.6 Hz), 7.46 (1H, d, J=7.6 Hz), 7.41 (1H, s), 7.26 (1H, t, J=60.8 Hz), 6.79 (1H, d, J=8.4 Hz), 4.03 (2H, s), 3.60-3.68 (4H, m), 3.47 (3H s), 0.66-2.72 (4H, m).

Example 49: 6-(1-difluoromethyl-1Hpyrazol-4-yl)-4 (6-(4-(4-(methylsulfonyl) benzyl) piperazin-1-yl) pyridin-3-yl)pyrazolo[1,5-a]pyridine-3-carbonitrile

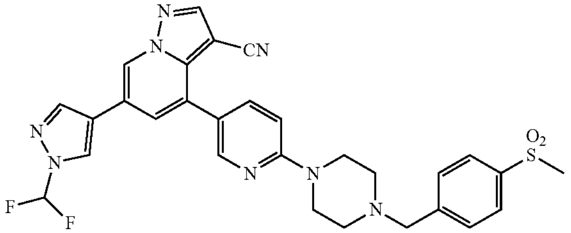 [SMILES: CS(=O)(=O)c1ccc(CN2CCN(c3ccc(-c4cc(-c5cnn(C(F)F)c5)cn5ncc(C#N)c45)cn3)CC2)cc1]

To a flask charged with dioxane and water (20 mL, volume ratio 5:1) were sequentially added Intermediate 8 (62 mg). (1-(difluoromethyl)-1H-pyrazol-4-yl)boronic acid (23 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (22 mg).

$^1$H NMR (400 MHz, $CDCl_3$) δ 8.70 (1H, s), 8.37 (1H, d, J=2.8 Hz), 8.30 (1H, s), 8.13 (1H, s), 7.96 (1H, s), 7.93 (2H, d, J=7.6 Hz), 7.75 (1H, dd, J=8.8 Hz, 2.8 Hz), 7.61 (2H, d, J=8.0 Hz), 7.41 (1H, s), 7.26 (1H, t, J=60.8 Hz), 6.78 (1H, d, J=8.8 Hz), 3.68-3.72 (4H, n). 3.67 (2H, s), 3.08 (3H, s), 2.58-2.63 (4H, m).

Example 50: 6-(1-methyl-1Hpyrazol-4-yl)-4-(6-(6-((6-(methylthio)pyridin-3-yl) methyl)-3,6-diazabicyclo[3.1.1]heptan-3-yl)pyridin-3-yl)pyrazolo[1,5-a]pyridine-3-carbonitrile

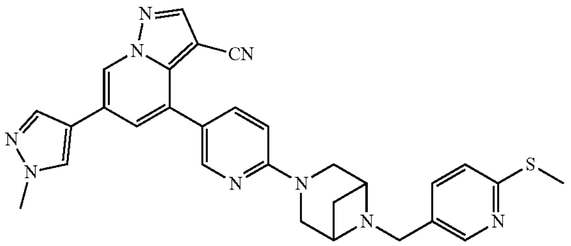 [SMILES: CSc1ccc(CN2C3CC2CN(c2ccc(-c4cc(-c5cnn(C)c5)cn5ncc(C#N)c45)cn2)C3)cn1]

At 0° C., Intermediate 2 (40 mg) was dissolved in THE (10 mL), 6-(methylthio) pyridin-3-carbaldehyde (31 mg) and sodium triacetoxyborohydride (75 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (13 mg).

$^1$H NMR (400 MHz, $CDCl_3$) δ 8.67 (1H, s), 8.45 (1H, s), 8.44 (1H, s), 8.29 (1H, s), 7.87 (1H, d, J=8.8 Hz), 7.80 (1H, s), 7.77 (1H, d, J=8.4 Hz), 7.70 (1H, s), 7.43 (1H, s), 7.36 (1H, d, J=8.4 Hz), 6.76 (1H, d, J=8.4 Hz), 4.38 (2H, d, J=6.0 Hz), 3.98-4.02 (5H, m), 3.85-3.96 (4H, m), 3.26-3.32 (OH, m), 2.58 (3H, s), 1.87 (1H, d, J=10.0 Hz).

Example 51: 6-(1-methyl-1Hpyrazol-4-yl)-4-(6-(4-((6-(methylthio) pyridin-2-yl) methyl) piperazin-1-yl)pyridin-3-yl)pyrazolo[1,5-a]pyridine-3-carbonitrile

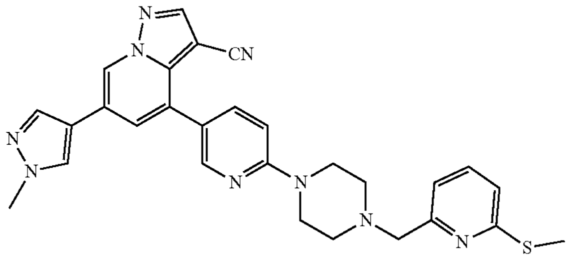

At 0° C., Intermediate 1 (39 mg) was dissolved in THE (10 mL). 6-(methylthio) picolinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1$H NMR (400 MHz, $CDCl_3$) δ 8.63 (1H, s), 8.36 (1H, d, J=2.8 Hz), 8.26 (1H, s), 7.79 (1H, s), 7.75 (1H, dd, J=8.8 Hz. 2.8 Hz), 7.68 (1H, s), 7.50 (1H, t, J=7.6 Hz), 7.39 (1H, s), 7.19 (1H, d, J=7.2 Hz), 7.07 (1H, d, J=7.6 Hz), 6.78 (1H, d, J=9.2 Hz), 3.99 (3H, s), 3.67-3.76 (6H, m), 2.65-2.73 (4H, n), 2.57 (3H, s).

Example 52: 6-(3,3-difluoroazetidin-1-yl)-4-(6-(4-((5-methoxypyridin-2-yl) methyl) piperazin-1-yl) pyridin-3-yl)pyrazolo[1,5-a]pyridine-3-carbonitrile

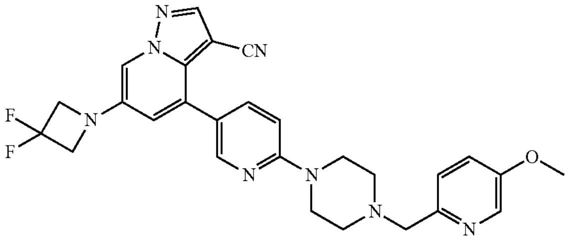 [SMILES: COc1ccc(CN2CCN(c3ccc(-c4cc(N5CC(F)(F)C5)cn5ncc(C#N)c45)cn3)CC2)nc1]

To a flask charged with toluene (20 mL) were sequentially added Intermediate 19 (57 mg). 3,3-difluoroazetidine hydrochloride (26 mg), tris(dibenzylideneacetone)dipalladium (9 mg). (±)-2,2'-Bis(diphenylphosphino)-1,1'-binaphthalene (12 ng) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane: methanol=20:1 (V:V)) to obtain the target compound (10 mg).

$^1$H NMR (400 MHz, $CDCl_3$) δ 8.27-8.36 (2H, m), 8.16 (1H, s), 7.76 (1H, d, J=1.2 Hz), 7.71 (1H, d, J=7.6 Hz), 7.37 (1H, d, J=7.6 Hz), 7.17-7.22 (1H, m), 6.71-6.76 (2H, m) 4.30 (4H, t, J=11.2 Hz), 3.95 (3H, s), 3.87 (2H, s), 3.60-3.76 (4H, m), 2.56-2.70 (4H, m).

Example 53: 6-(1Hpyrazol-4-yl)-4-(6-(6-(4-(methylsulfonyl)benzyl)-3,6-diazabicyclo 13.1.11 heptan-3-yl)pyridin-3-yl)pyrazolo[1,5-a]pyridine-3-carbonitrile

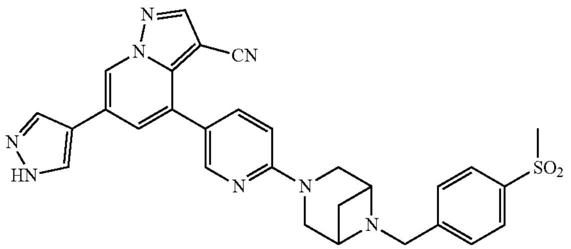 [SMILES: CS(=O)(=O)c1ccc(CN2C3CC2CN(c2ccc(-c4cc(-c5cn[nH]c5)cn5ncc(C#N)c45)cn2)C3)cc1]

To a flask charged with dioxane and water (20 mL, volume ratio 5:1) were sequentially added Intermediate 6 (64 mg), (1H-pyrazol-4-yl)boronic acid (17 mg), tetrakis (triphenylphosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=10:1 (V:V)) to obtain the target compound (17 mg).

$^1$H NMR (400 MHz, $CDCl_3$) δ 8.70 (1H, s), 8.44 (1H, d, J=2.4 Hz), 8.29 (1H, s), 7.92 (2H, s), 7.89 (2H, d, J=8.0 Hz), 7.83 (1H, dd, J=8.8 Hz, 2.4 Hz), 7.61 (2H, d, J=8.0 Hz), 7.45 (1H, s), 6.71 (1H, d, J=8.8 Hz), 3.79-3.87 (4H, m), 3.75 (2H, s), 3.60-3.68 (2H, m), 3.05 (3H, s), 2.72-2.80 (1H, m), 1.69 (1H, d, J=8.8 Hz).

Example 54: 2-(4-(3-cyano-4-(6-(4-(4-(methylsulfonyl)benzyl)piperazin-1-yl) pyridin-3-yl) pyrazolo[1,5-a]pyridine-1-yl)-1H-pyrazol-1-yl)-N,N-dimethylacetamide

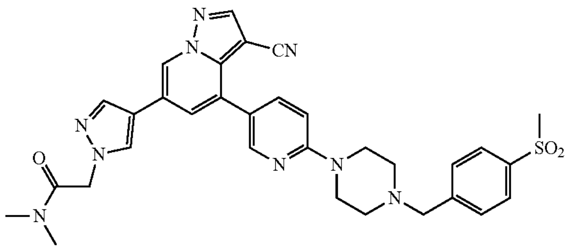 [SMILES: CN(C)C(=O)Cn1cc(-c2cc(-c3ccc(N4CCN(Cc5ccc(S(C)(=O)=O)cc5)CC4)nc3)c3c(C#N)cnn3c2)cn1]

To a flask charged with dioxane and water (20 mL, volume ratio 5:1) were sequentially added Intermediate 8 (62 mg), N,N-dimethyl-2-(4-(4,4,5,5-tetramethyl-1,3,2-dioxaborolan-2-yl)-1H-pyrazol-1-yl) acetamide (42 mg), tetrakis (triphenyl phosphine) palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=10:1 (V:V)) to obtain the target compound (27 mg).

$^1$H NMR (400 MHz, $CDCl_3$) δ 8.65 (1H, d, J=1.2 Hz), 8.35 (1H, d, J=2.8 Hz), 8.25 (1H, s), 7.93 (2H, d, J=8.0 Hz), 7.87 (1H, s), 7.82 (1H, s), 7.73 (1H, dd, J=8.8 Hz, 2.8 Hz), 7.62 (2H, d, J=8.0 Hz), 7.41 (1H, d, J=1.2 Hz), 6.77 (1H, d, J=8.8 Hz), 5.05 (2H, s), 3.65-3.75 (6H, m), 3.13 (3H, s), 3.07 (3H, s), 3.02 (3H, s), 2.59-2.67 (4H, m).

Example 55: 6-(1-difluoromethyl-1Hpyrazol-4-yl)-4-(6-(6-(3-(methylsulfonyl) benzyl)-3,6-diazabicyclo[3.1.1]heptan-3-yl)pyridin-3-yl)pyrazolo[1,5-a] pyridine-3-carbonitrile

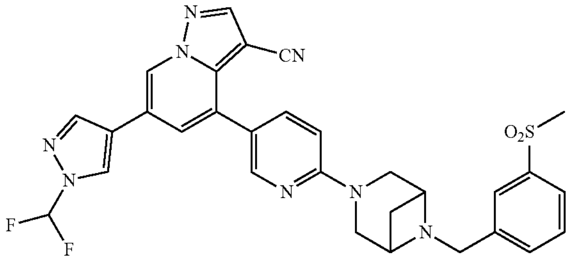 [SMILES: CS(=O)(=O)c1cccc(CN2C3CC2CN(c2ccc(-c4cc(-c5cnn(C(F)F)c5)cn5ncc(C#N)c45)cn2)C3)c1]

To a flask charged with dioxane and water (20 mL, volume ratio 5:1) were sequentially added Intermediate 9

(64 mg), (1-(difluoromethyl)-1H-pyrazol-4-yl)boronic acid (23 mg), tetrakis(triphenyl phosphine)palladium (11 ng) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (25 mg).

$^1$H NMR (400 MHz, $CDCl_3$) δ 8.72 (1H, d, J=1.6 Hz), 8.44 (1H, d, J=2.4 Hz), 8.31 (1H, s), 8.14 (1H s), 7.99 (1H s), 7.97 (1H s), 7.81-7.84 (2H, m), 7.69-7.73 (1H, m), 7.53 (1H, t, J=8.0 Hz), 7.44 (1H, d, J=1.2 Hz), 7.25 (1H, t, J=60.4 Hz), 6.72 (1H, d, J=8.4 Hz), 3.81-3.92 (4H, m), 3.77 (2H, s), 3.62-3.70 (2H, m), 3.07 (3H, s), 2.76-2.86 (1H, m), 1.71 (1H, d, J=8.0 Hz).

Example 56: 6-(1-difluoromethyl-1Hpyrazol-4-yl)-4-(6-(6-(2-(methylsulfonyl) benzyl)-3,6-diazabicyclo[3.1.1]heptan-3-yl)pyridin-3-yl)pyrazolo[1,5-a] pyridine-3-carbonitrile

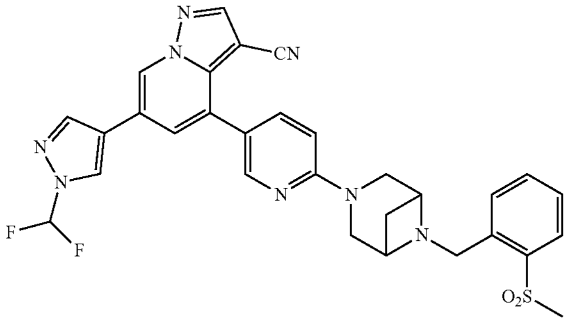 [SMILES: CS(=O)(=O)c1ccccc1CN1C2CC1CN(c1ccc(-c3cc(-c4cnn(C(F)F)c4)cn4ncc(C#N)c34)cn1)C2]

To a flask charged with dioxane and water (20 mL, volume ratio 5:1) were sequentially added Intermediate 20 (64 mg), (1-(difluoromethyl)-1H-pyrazol-4-yl)boronic acid (23 mg), tetrakis(triphenyl phosphine)palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane: methanol=20:1 (V:V)) to obtain the target compound (35 mg).

$^1$H NMR (400 MHz, $CDCl_3$) δ 8.71 (1H, d, J=1.6 Hz), 8.45 (1H, d, J=2.4 Hz), 8.31 (1H, s), 8.14 (1H, s), 8.09 (1H, d, J=8.0 Hz), 7.97 (1H, s), 7.82 (I H, dd, J=8.8 Hz, 2.4 Hz), 7.45-7.58 (3H, m), 7.43 (1H, d, J=1.2 Hz), 7.25 (1H, t, J=60.8 Hz), 6.74 (1H, d, J=8.8 Hz), 4.12 (2H, s), 3.95 (2H, d, J=12.4 Hz), 3.83 (2H, s), 3.61-3.72 (2H, m), 3.36 (3H, s), 2.58-2.66 (I H, m), 1.69 (1H, d, J=9.2 Hz).

Example 57: 6-(1-methyl-1Hpyrazol-4-yl) 4-(6-(8-(4-(methylsulfonyl)benzyl)-3,8-diazabicyclo[3.2.1]octan-3-yl)pyridin-3-yl)pyrazolo[1,5-a]pyridine-3-carbonitrile

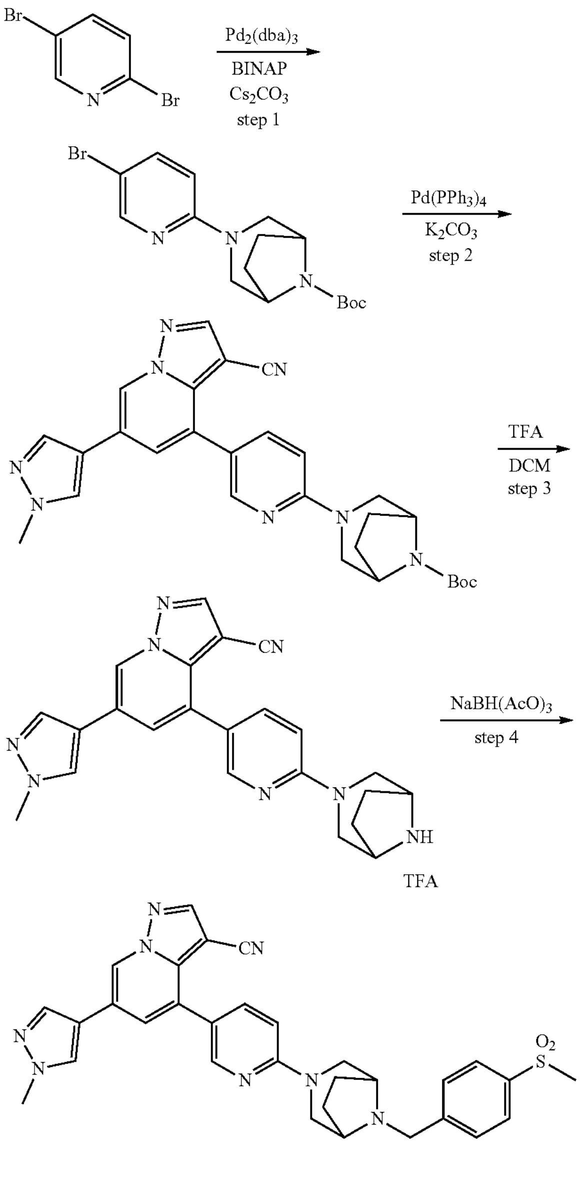

Step 1: tert-butyl 3-(5-bromopyridin-2-yl)-3,8-diazabicyclo[3.2.1]octane-8-carboxylate Under protection of nitrogen, 2,5-dibromopyridine (4.74 g), tert-butyl 3,8-diazabicyclo[3.2.1]octane-8-carboxylate (2.12 g), tris(dibenzylideneacetone)dipalladium (0.92 g), (±)-2,2'-Bis(diphenyl phosphino)-1,1'-binaphthalene (1.24 g) and cesium carbonate (6.52 g) were added to toluene (200 mL), and the mixture was heated to 110° C. and stirred overnight. The mixture was cooled to room temperature and filtered, the filter cake was washed with dichloromethane, and the filtrate was combined, concentrated, and purified through column chromatography (eluent: petroleum ether: ethyl acetate=4:1 (V:V)) to obtain tert-butyl 3-(5-bromopyridin-2-yl)-3,8-diazabicyclo[3.2.1]octane-8-carboxylate (2.4 g).

Step 2: tert-butyl 3-(5-(3-cyano-6-(1-methyl-1Hpyrazol-4-yl)pyrazolo[1,5-a] pyridine-4-yl) pyridin-2-yl)-3,8-diazabicyclo[3.2.1]octane-8-carboxylate To a flask charged with dioxane and water (20 mL, volume ratio 5:1) were sequentially added tert-butyl 3-(5-bromopyridin-2-yl)-3,8-diazabicyclo[3.2.1]octane-8-carboxylate (37 mg), (3-cyano-6-(1-methyl-1Hpyrazol-4-yl) pyrazolo[1,5-a]pyridine-4-yl) boronic acid (40 mg), tetrakis (triphenyl phosphine) palladium (11 mg) and potassium carbonate (28 mg), and the flask was purged 3 times with nitrogen. The mixture was heated to 80° C. and stirred overnight. The mixture was cooled to room temperature, the reaction solution was poured into water (50 mL), and the mixture was extracted with ethyl acetate. The organic phase was dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the target compound (33 rug).

Step 3: 4-(6-(3,8-diazabicyclo[3.2.1]octan-3-yl)pyridin-3-yl)-6-(1-methyl-1Hpyrazol-4-yl) pyrazolo[1,5-a]pyridine-3-carbonitrile trifluoroacetate At room temperature, the product obtained in step 2 was dissolved in dichloromethane (4 mL), trifluoroacetic acid (1 mL) was added, the mixture was stirred for 2 hours, the reaction was completed, and the solvent was removed through vacuum evaporation under reduced pressure. To the residue was added tert-butyl methyl ether (5 mL), the mixture was ultra-sonicated, the solid precipitated was filtered, and the filter cake was washed twice with tert-butyl methyl ether and dried in vacuum to obtain the target product. (20 mg)

Step 4: 6-(1-methyl-1Hpyrazol-4-yl)-4-(6-(8-(4-(methylsulfonyl)benzyl)-3,8-diazabicyclo[3.2.1]octan-3-yl)pyridin-3-yl)pyrazolo[1,5-a]pyridine-3-carbonitrile

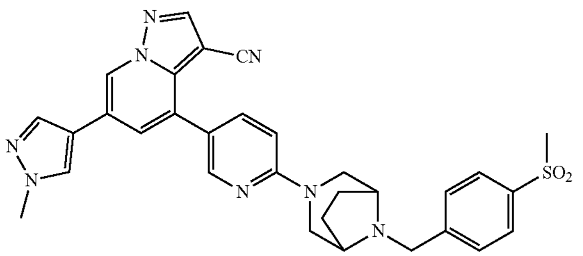 [SMILES: Cn1cc(-c2cc(-c3ccc(N4CC5CCC(C4)N5Cc4ccc(S(C)(=O)=O)cc4)nc3)c3c(C#N)cnn3c2)cn1]

At 0° C. the product obtained in step 3 (20 mg) was dissolved in THF (5 mL), 4-(methyl sulfonyl)benzaldehyde (15 mg) and sodium triacetoxyborohydride (50 mg) were sequentially added, and the mixture was let warm up to room temperature and stirred for 12 hours. The reaction solution was poured into an aqueous solution of saturated sodium bicarbonate (20 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (10 mg).

$^1$H NMR (400 MHz, $CDCl_3$) δ 8.62 (1H, d, J=1.2 Hz), 8.36 (1H, d, J=2.4 Hz), 8.26 (1H, s), 7.92 (2H, d, J=8.0 Hz), 7.78 (1H, s), 7.74 (1H, dd, J=8.4 Hz, 2.4 Hz), 7.63-7.71 (3H, m), 7.38 (1H, d, J=1.6 Hz), 6.68 (1H, d, J=8.4 Hz), 3.99 (3H, s), 3.88-3.95 (2H, m), 3.70-3.77 (2H, m), 3.20-3.39 (4H, m), 3.07 (3H, s), 2.04-2.11 (2H, m), 1.79-1.86 (2H, m).

Example 58: 6-(3-hydroxy-3-methylazetidin-1-yl)-4-(6-(6-((2-methoxypyrimidin-5-yl) methyl)-3,6-diazabicyclo[3.1.1]heptan-3-yl)pyridin-3-yl)pyrazolo[1,5-a]pyridine-3-carbonitrile

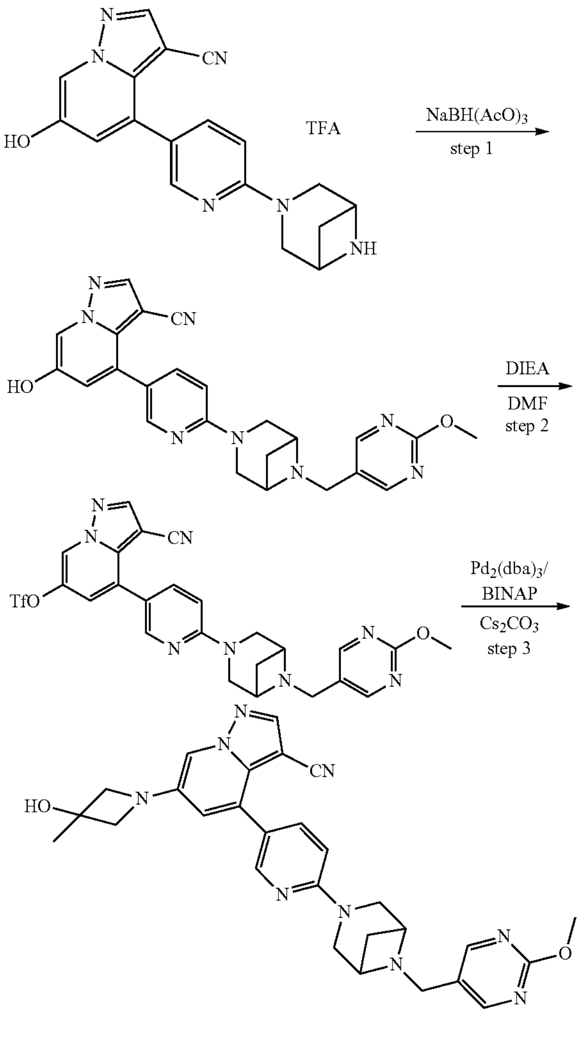

Step 1: 6-hydroxy-4-(6-(6-((2-methoxypyrimidin-5-yl) methyl)-3,6-diazabicyclo[3.1.1]heptan-3-yl)pyridin-3-yl)pyrazolo[1,5-a]pyridine-3-carbonitrile At room temperature, 4-(6-(3,6-diazabicyclo [3.1.1]heptan-3-yl) pyridin-3-yl)-6-hydroxyl pyrazolo[1,5-a]pyridine-3-carbonitrile trifluoroacetate (430 mg) was dissolved in tetrahydrofuran (50 mL), 2-methoxypyrimidin-5-carbaldehyde (276 mg) was added, the mixture was stirred for 5 minutes, and sodium triacetoxyborohydride (500 mg) was added. The mixture was stirred until the reaction was completed, the reaction solution was poured into an aqueous solution of saturated sodium bicarbonate, the mixture was extracted twice with ethyl acetate, and the organic phase was washed with brine, dried over anhydrous sodium sulphate, evaporated under reduced pressure to dryness to remove the solvent, and purified through column chromatography (eluent: dichloromethane:methanol=30:1 (V:V)) to obtain 6-hydroxy-4-(6-(6-((6-methoxypyridin-3-yl) methyl)-3,6-diazabicyclo[3.1.1]heptan-3-yl) pyridin-3-yl)pyrazolo[1,5-a]pyridine-3-carbonitrile (230 mg).

Step 2: 3-cyano-4-(6-(6-((2-methoxypyrimidin-5-yl) methyl)-3,6-diazabicyclo[3.1.1] heptan-3-yl) pyridin-3-yl)pyrazolo[1,5-a]pyridine-6-yl trifluoromethane sulfonate At room temperature, 6-hydroxy-4-(6-(6-((2-methoxypyrimidin-5-yl) methyl)-3,6-diazabicyclo[3.1.1]heptan-3-yl) pyridin-3-yl)pyrazolo[1,5-a]pyridine-3-carbonitrile (227 mg) was dissolved in DMF (30 mL), to the mixture was added DIEA (258 ng), and N-Phenyl-bis (trifluoro methanesulfonamide) (357 mg) was added. After the mixture was stirred at room temperature overnight, the reaction was completed, the mixture was poured into water (150 mL), and the mixture was extracted twice with ethyl acetate. The organic phase was washed twice with brine, dried over anhydrous sodium sulphate, evaporated under reduced pressure to dryness, and purified through column chromatography (eluent: petroleum ether:ethyl acetate=3:1 (V:V)) to obtain 3-cyano-4-(6-(6-((2-methoxypyrimidin-5-yl) methyl)-3,6-diazabicyclo[3.1.1]heptan-3-yl) pyridin-3-yl) pyrazolo[1,5-a]pyridine-6-yl trifluoro methanesulfonate (210 mg).

Step 3: 6-(3-hydroxy-3-methylazetidin-1-yl)-4-(6-(6-((2-methoxy pyrimidin-5-yl) methyl)-3,6-diazabicyclo[3.1.1]heptan-3-yl)pyridin-3-yl)pyrazolo[1,5-a]pyridine-3-carbonitrile To a flask charged with toluene (20 mL) were sequentially added the product obtained in step 2 (59 mg), 3-methylazetidin-3-ol hydrochloride (27 mg), tris(dibenzylideneacetone) dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated, and the residue was purified through Thin Layer Chromatography developing solvent: dichloromethane:methanol=20:1 (V:V)) to obtain the target compound (21 mg).

$^1$H NMR (400 MHz, $CDCl_3$) δ 8.54 (2H, s), 8.38 (1H, d, J=2.4 Hz), 8.15 (1H, s), 7.79 (1H, dd, J=8.8 Hz. 2.4 Hz), 7.72 (1H, d, J=1.6 Hz), 6.74 (1H, d, J=2.0 Hz), 6.69 (1H, d, J=8.4 Hz), 4.00 (3H, s), 3.91 (2H, d, J=8.0 Hz), 3.78-3.89 (6H, m), 3.58-3.72 (4H, m), 2.69-2.82 (1H, m), 1.69 (1H, d, J=8.0 Hz), 1.67 (3H, s).

Example 59: 6-(1-methyl-1Hpyrazol-4-yl)-4-(6-(6-(4-(methylthio)benzyl)-3,6-diazabicyclo[3.1.1] heptan-3-yl)pyridin-3-yl)pyrazolo[1,5-a]pyridine-3-carbonitrile

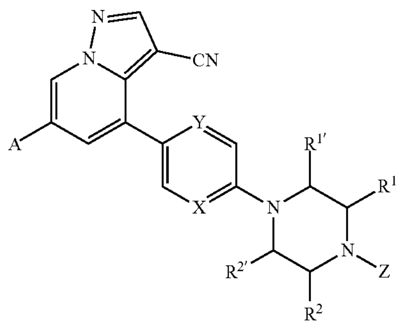

At 0° C. Intermediate 2 (40 mg) was dissolved in THF (10 mL), 4-(methylthio) benzaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (30 mg).

$^1$H NMR (400 MHz, $CDCl_3$) δ 8.66 (1H, d, J=1.2 Hz), 8.45 (1H, d, J=2.4 Hz), 8.27 (1H, s), 7.85 (1H, dd, J=8.4 Hz, 2.4 Hz), 7.80 (1H, s), 7.70 (1H, s), 7.50 (2H, d, J=8.0 Hz), 7.43 (1H, d, J=1.2 Hz), 7.24 (2H, d, J=8.0 Hz), 6.73 (1H, d, J=8.4 Hz), 4.18-4.32 (2H, m), 3.80-4.09 (9H, m), 3.16-3.30 (1H, m), 2.47 (3H, s), 1.82-1.89 (1H, m).

Example 60: 6-(1-(difluoromethyl)-1Hpyrazol-4-yl)-4-(6-(6-((6-(methylthio) pyridin-3-yl) methyl)-3,6-diazabicyclo[3.1.1]heptan-3-yl)pyridin-3-yl)pyrazolo [1,5-a]pyridine-3-carbonitrile

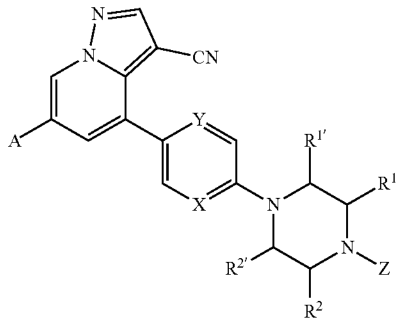

At 0° C. Intermediate 21 (43 mg) was dissolved in THF (10 mL), 6-(methylthio)nicotinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (27 mg).

$^1$H NMR (400 MHz, $CDCl_3$) δ 8.72 (1H, d, J=1.6 Hz), 8.44 (1H, d, J=2.4 Hz), 8.41 (1H, d, J=2.0 Hz), 8.31 (1H, s), 8.14 (1H, s), 7.97 (1H, s), 7.82 (1H, dd, J=8.8 Hz, 2.4 Hz), 7.64-7.70 (1H, m), 7.43 (1H, d, J=1.6 Hz), 7.25 (1H, t, J=60.4 Hz), 7.16 (1H, d, J=8.4 Hz), 6.71 (1H, d, J=8.8 Hz), 3.84-3.94 (4H, m), 3.62-3.73 (4H, m), 2.78-2.86 (1H, m), 2.55 (3H, s), 1.71 (1H, d, J=8.4 Hz).

Example 61: (E)-4-(6-(6-(4-methoxybut-2-enoyl)-3,6-diazabicyclo[3.1.1] heptan-3-yl) pyridin-3-yl)-6-(1-methyl-1Hpyrazol-4-yl)pyrazolo[1,5-a]pyridine-3-carbonitrile

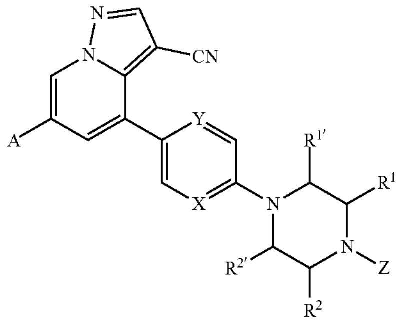

At 0° C. Intermediate 2 (40 mg) was dissolved in THF (10 mL), (E)-4-methoxybut-2-enoic acid (12 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (37 mg).

$^1$H NMR (400 MHz, $CDCl_3$) δ 8.63 (1H, d, J=1.2 Hz), 8.37 (1H, d, J=2.4 Hz), 8.25 (1H, s), 7.78 (I H, s), 7.76 (1H, dd, J=8.8 Hz, 2.4 Hz), 7.68 (1H, s), 7.38 (1H, d, J=1.2 Hz), 6.88 (1H, dt, J=15.6 Hz. 4.0 Hz), 6.65 (1H, d, J=8.8 Hz), 6.16 (1H, dt, J=15.6 Hz, 2.0 Hz), 4.64-4.72 (2H, n), 4.17 (1H, d, J=12.0 Hz), 4.06-4.09 (2H, m), 3.98 (3H, s), 3.88-3.91 (2H, m), 3.64-3.71 (1H, m), 3.39 (3H, s), 2.78-2.84 (1H m), 1.73 (1H, d, J=8.8 Hz).

Example 62: (E)-6-(1-(difluoromethyl)-1Hpyrazol-4-yl)-4-(6-(6-(4-methoxybut-2-enoyl)-3,6-diazabicyclo[3.1.1]heptan-3-yl)pyridin-3-yl)pyrazolo[1,5-a]pyridine-3-carbonitrile

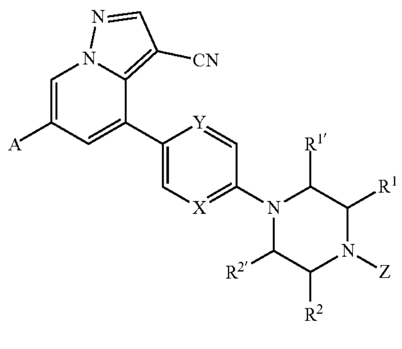

At 0° C., Intermediate 21 (43 mg) was dissolved in THE (10 mL). (E)-4-methoxybut-2-enoic acid (12 mg) and triethylamine (30 mg) were added, and the mixture was let warm up to room temperature and stirred for 1 hour. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (39 mg).

$^1$H NMR (400 MHz, $CDCl_3$) δ 8.70 (1H, d, J=1.2 Hz), 8.38 (1H, d, J=2.4 Hz), 8.29 (1H, s), 8.13 (1H s), 7.96 (1H, s), 7.76 (1H, dd, J=8.8 Hz, 2.4 Hz), 7.39 (1H, d, J=1.6 Hz), 7.25 (1H, t, J=60.4 Hz), 6.89 (1H, dt, J=15.2 Hz, 4.0 Hz), 6.64 (1H, d, J=8.8 Hz), 6.16 (1H, dt, J=15.2 Hz, 2.0 Hz), 4.64-4.72 (2H, m), 4.18 (1H, d, J=10.8 Hz), 4.06-4.09 (2H, m), 3.88-3.92 (2H, m). 3.67 (1H, d, J=10.8 Hz), 3.39 (3H, s), 2.78-2.84 (1H, n), 1.74 (1H, d, J=8.8 Hz).

Example 63: 6-(1-(difluoromethyl)-1Hpyrazol-4-yl)-4-(6-(4-((6-(methylsulfonyl) pyridin-3-yl) methyl) piperazin-1-yl)pyridin-3-yl)pyrazolo[1,5-a]pyridine-3-carbonitrile

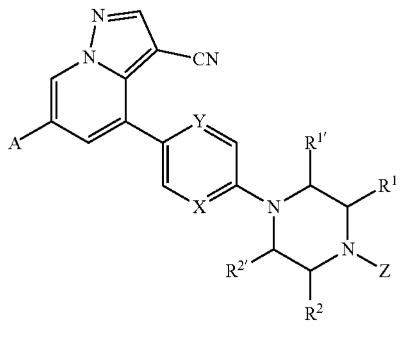

At 0° C. Intermediate 24 (42 mg) was dissolved in THE (10 mL). 6-(methyl sulfonyl)nicotinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (25 mg).

$^1$H NMR (400 MHz, $CDCl_3$) δ 8.72 (1H, s), 8.70 (1H, d, J=1.6 Hz), 8.36 (1H, d, J=2.4 Hz), 8.29 (1H, s), 8.13 (1H, s), 8.07 (1H, s), 8.02 (1H, d, J=7.2 Hz), 7.96 (1H, s), 7.75 (1H, dd, J=9.2 Hz, 2.4 Hz), 7.40 (1H, d, J=1.6 Hz), 7.25 (1H, t, J=60.4 Hz), 6.78 (1H, d, J=8.8 Hz), 3.64-3.74 (6H, m), 3.25 (3H, s), 2.58-2.64 (4H, m).

Example 64: 6-(3,3-difluoroazetidin-1-yl)-4-(6-(6-(3-(methylsulfonyl)benzyl)-3,6-diazabicyclo[3.1.1]heptan-3-yl)pyridin-3-yl)pyrazolo[1,5-a]pyridine-3-carbonitrile

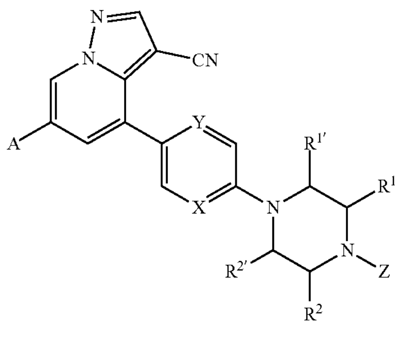

To a flask charged with toluene (20 mL) were sequentially added Intermediate 9 (64 mg). 3,3-difluoroazetidine hydrochloride (26 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (29 mg).

$^1$H NMR (400 MHz, $CDCl_3$) δ 8.38 (1H, d, J=2.4 Hz), 8.19 (1H, s), 7.98 (1H, s), 7.82 (1H, d, J=8.0 Hz), 7.77-7.80 (2H, m), 7.69 (1H, d, J=6.8 Hz), 7.52 (1H, t, J=8.0 Hz), 6.75 (1H, d, J=2.0 Hz), 6.69 (1H, d, J=9.2 Hz), 4.31 (4H, t, J=11.6 Hz), 3.78-3.88 (4H, n), 3.72 (2H, s), 3.58-3.68 (2H, m), 3.06 (3H, s), 2.73-2.82 (1H m), 1.69 (1H, d, J=8.4 Hz).

Example 65: 6-(3-hydroxy-3-methylazetidin-1-yl)-4-(6-(6-(3-(methylsulfonyl) benzyl)-3,6-diazabicyclo[3.1.1]heptan-3-yl)pyridin-3-yl)pyrazolo[1,5-a] pyridine-3-carbonitrile

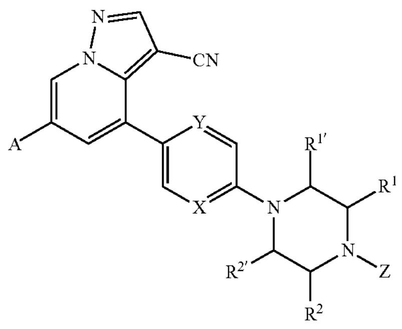

To a flask charged with toluene (20 mL) were sequentially added Intermediate 9 (64 mg), 3-methylazetidin-3-ol hydrochloride (27 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (21 mg).

$^1$H NMR (400 MHz, $CDCl_3$) δ 8.37 (1H, d, J=2.4 Hz), 8.15 (1H, s), 7.98 (1H, s), 7.81 (1H, d, J=7.6 Hz), 7.78 (1H, dd, J=8.8 Hz. 2.4 Hz), 7.71 (1H, d, J=2.0 Hz), 7.67 (1H, d, J=8.0 Hz), 7.51 (1H, t, J=8.0 Hz), 6.74 (1H, d, J=2.0 Hz), 6.68 (1H, d, J=8.8 Hz), 3.91 (2H, d, J=8.0 Hz), 3.77-3.87 (6H, m), 3.73 (2H, s), 3.58-3.66 (2H, m), 3.06 (3H, s), 2.72-2.79 (1H, m), 1.67 (1H, d, J=9.2 Hz), 1.66 (3H, s).

Example 66: 6-(1-(difluoromethyl)-1Hpyrazol-4-yl)-4-(6-(6-((5-(methylthio) pyridin-2-yl) methyl)-3,6-diazabicyclo[3.1.1]heptan-3-yl)pyridin-3-yl)pyrazolo [1,5-a]pyridine-3-carbonitrile

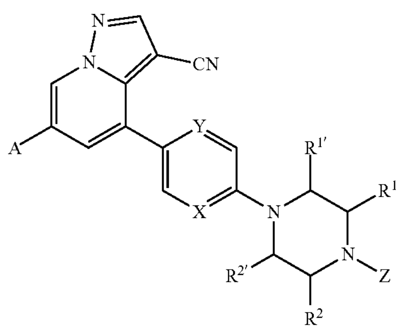

At 0° C., Intermediate 21 (43 mg) was dissolved in THF (10 mL), 5-(methylthio)picolinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (31 mg).

$^1$H NMR (400 MHz, $CDCl_3$) δ 8.74 (OH, s), 8.45 (1H, d, J=2.4 Hz), 8.43 (1H, s), 8.32 (1H, s), 8.15 (OH, s), 7.98 (1H, s), 7.86 (1H, dd, J=8.8 Hz, 2.4 Hz), 7.76 (1H, d, J=8.0 Hz), 7.43 (1H, s), 7.35 (1H, d, J=8.0 Hz), 7.26 (H t, J=60.4 Hz), 6.75 (1H, d, J=8.8 Hz), 4.38 (21, d, J=5.6 Hz), 3.99 (2H, s), 3.89 (4H, s), 3.24-3.32 (1H, m), 2.56 (3H, s), 1.86 (1H, d, J=10.4 Hz).

Example 67: 6-(3,3-difluoroazetidin-1-yl)-4-(6-(6-(2-(methylsulfonyl)benzyl)-3,6-diazabicyclo [3.1.1] heptan-3-yl)pyridin-3-yl)pyrazolo[1,5-a]pyridine-3-carbonitrile

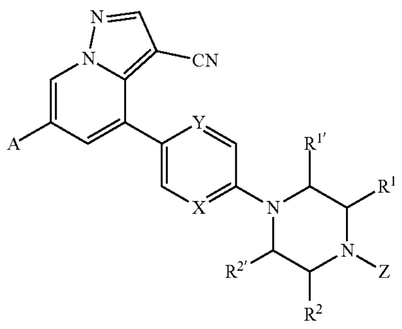

To a flask charged with toluene (20 mL) were sequentially added Intermediate 20 (64 mg). 3,3-difluoroazetidine hydrochloride (26 mg), tris(dibenzylideneacetone)dipalladium (9 mg), (±)-2,2'-Bis(diphenylphosphino)-1,1'-binaphthalene (12 mg) and cesium carbonate (98 mg), and the flask was purged 3 times with nitrogen. The mixture was heated to 110° C. and stirred overnight. The mixture was cooled to room temperature and filtered, the filter cake was washed with dichloromethane, the filtrate was combined and concentrated under reduced pressure, and the residue was purified through Thin Layer Chromatography (developing solvent: dichloromethane:methanol=20:1 (V:V)) to obtain the target compound (19 mg).

$^1$H NMR (400 MHz, $CDCl_3$) δ 8.39 (1H, d, J=2.0 Hz), 8.18 (1H, s), 8.09 (1H, d, J=8.0 Hz), 7.76-7.79 (2H, m), 7.43-7.60 (3H, m), 6.75 (1H, d, J=2.0 Hz), 6.72 (1H, d, J=8.8 Hz), 4.31 (4H, t, J=11.6 Hz), 4.06-4.19 (2H, m), 3.90-3.99 (2H, m), 3.76-3.88 (2H, m), 3.59-3.71 (2H, m). 3.34 (3H, s), 2.52-2.72 (1H, m), 1.71 (1H, d, J=9.2 Hz).

Example 68: 4-(6-(6-(4-(methylsulfinyl)benzyl)-3,6-diazabicyclo[3.1.1]heptan-3-yl) pyridin-3-yl)-6-(1-(difluoromethyl)-1Hpyrazol-4-yl)pyrazolo[1,5-a] pyridine-3-carbonitrile

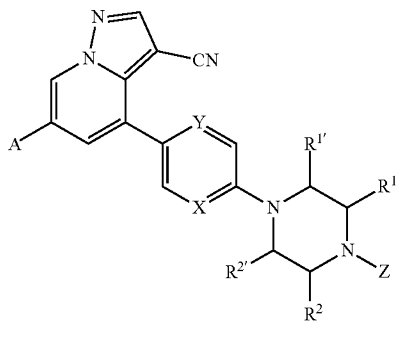

At 0° C., Intermediate 21 (43 mg) was dissolved in THF (10 mL), 4-(methylsulfonyl)benzaldehyde (34 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (32 mg).

$^1$H NMR (400 MHz, $CDCl_3$) δ 8.72 (1H, s), 8.44 (1H, d, J=2.4 Hz), 8.31 (1H, s), 8.14 (1H, s), 7.97 (1H, s), 7.82 (1H, dd, J=8.8 Hz, 2.4 Hz), 7.58-7.64 (4H, m), 7.43 (1H, d, J=1.2 Hz), 7.25 (1H, t, J=60.4 Hz), 6.72 (1H, d, J=8.4 Hz), 3.83-3.98 (4H, m), 3.79 (2H, s), 3.63-3.73 (2H, m), 2.82-2.92 (1H, m), 2.72 (3H, s), 1.73 (1H, d, J=9.2 Hz).

Example 69: 6-(1-difluoromethyl-1Hpyrazol-4-yl)-4-(6-(8-(4-(methylsulfonyl) benzyl)-3,8-diazabicyclo[3.2.1]octan-3-yl)pyridin-3-yl)pyrazolo[1,5-a] pyridine-3-carbonitrile

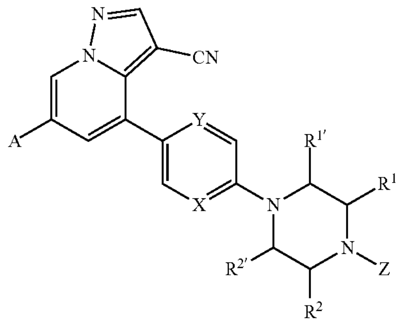

At 0° C. Intermediate 22 (45 mg) was dissolved in THF (15 mL), 4-(methylsulfonyl)benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (30 mg).

$^1$H NMR (400 MHz, $CDCl_3$) δ 8.70 (1H, d, J=1.2 Hz), 8.36 (1H, d, J=2.8 Hz), 8.29 (1H, s), 8.12 (1H, s), 7.96 (1H, s), 7.92 (2H, d, J=8.0 Hz), 7.74 (1H, dd, J=8.8 Hz, 2.8 Hz), 7.67 (2H, d, J=8.0 Hz), 7.40 (1H, s), 7.25 (1H, t, J=60.4 Hz), 6.68 (1H, d, J=8.8 Hz), 3.91 (2H, d, J=11.2 Hz), 3.74 (2H, s), 3.35 (2H, s), 3.26 (2H, d, J=11.2 Hz), 3.07 (3H, s), 2.04-2.10 (2H, m), 1.78-1.85 (2, m).

Example 70: 4-(5-(6-(4-(methylsulfonyl)benzyl)-3,6-diazabicyclo[3.1.1]heptan-3-yl) pyrazin-2-yl)-6-(1-(difluoromethyl)-1Hpyrazol-4-yl) pyrazolo[1,5-a] pyridine-3-carbonitrile

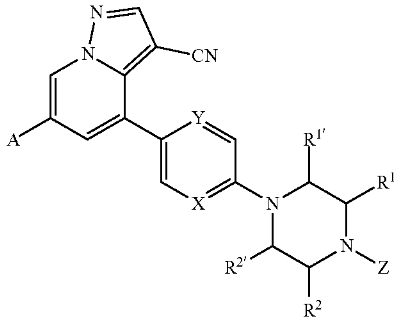

At 0° C., Intermediate 23 (43 ng) was dissolved in THE (15 mL), 4-(methylsulfonyl)benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (17 mg).

$^1$H NMR (400 MHz, $CDCl_3$) δ 8.74 (1H, d, J=1.6 Hz), 8.57 (1H, d, J=1.6 Hz), 8.35 (1H, s), 8.28 (1H, d, J=1.6 Hz), 8.16 (1H, s), 7.99 (1H, s), 7.90 (2H, d, J=8.8 Hz), 7.67 (1H, d, J=1.2 Hz), 7.60 (2H, d, J=8.0 Hz), 7.26 (1H, t, J=60.4 Hz), 3.82-3.90 (4H, m). 3.76 (2H, s), 3.68 (2H, d, J=12.8 Hz), 3.05 (3H, s), 2.77-2.84 (1H, m), 1.71 (1H, d, J=9.2 Hz).

Example 71: 6-(1-(difluoromethyl)-1Hpyrazol-4-yl)-4-(6-(6-((6-(methylthio) pyridin-3-yl) methyl)-3,6-diazabicyclo[3.1.1]heptan-3-yl)pyridin-3-yl)pyrazolo [1,5-a]pyridine-3-carbonitrile

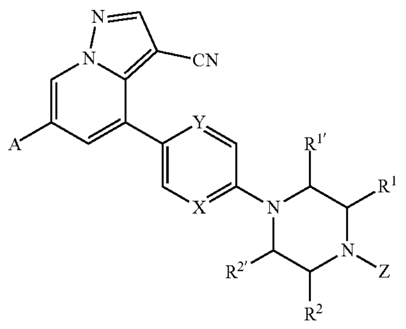

At 0° C., Intermediate 21 (43 mg) was dissolved in THE (10 mL), 6-(methylthio) pyridin-3-carbaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (32 mg).

$^1$H NMR (400 MHz, $CDCl_3$) δ 8.68 (1H, d, J=1.6 Hz), 8.31 (1H, d, J=2.8 Hz), 8.28 (1H, s), 8.11 (1H, s), 7.94 (1H, s), 7.89 (1H, d, J=2.8 Hz), 7.71 (1H, dd, J=8.8 Hz. 2.8 Hz), 7.37 (1H, s), 7.23 (1H, t, J=60.4 Hz), 7.03 (1H, d, J=8.4 Hz), 6.81 (1H, dd, J=8.8 Hz, 3.2 Hz), 6.56 (1H, d, J=8.8 Hz), 4.49 (2H, d, J=6.0 Hz), 4.06 (2H, d, J=12.0 Hz), 3.55-3.63 (2H, m), 2.88-2.94 (1H, m), 2.49 (3H, s), 1.82 (1H, d, J=8.8 Hz).

Example 72: 6-(1-(difluoromethyl)-1Hpyrazol-4-yl)-4-(6(6-((2-(methylthio) pyridin-4-yl) methyl)-3,6-diazabicyclo[3.1.1]heptan-3-yl)pyridin-3-yl)pyrazolo [1,5-a]pyridine-3-carbonitrile

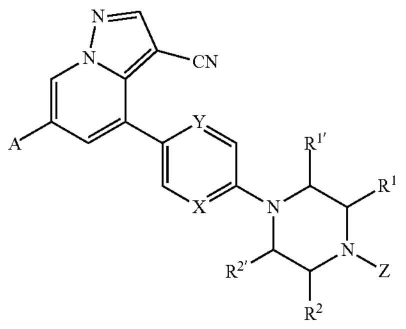

At 0° C., Intermediate 21 (43 mg) was dissolved in THE (10 mL), 2-(methylthio) pyridin-4-carbaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1$H NMR (400 MHz, $CDCl_3$) δ 8.71 (1H, d, J=1.6 Hz), 8.43 (1H, d, J=2.8 Hz), 8.35 (1H, d, J=4.8 Hz), 8.31 (1H, s), 8.13 (1H, s), 7.97 (1H, s), 7.81 (1H, dd, J=8.8 Hz, 2.4 Hz), 7.43 (1H, d, J=1.6 Hz), 7.25 (1H, t, J=60.4 Hz), 7.23 (1H, s), 7.01 (1H, d, J=4.0 Hz), 6.70 (1H, d, J=9.2 Hz), 3.77-3.84 (4H, m), 3.56-3.66 (4H, m), 2.73-2.82 (1H, m), 2.56 (3H, s), 1.68 (H, d, J=8.8 Hz).

Example 73: 6-(1-(difluoromethyl)-1Hpyrazol-4-yl)-4-(6-(8-((6-(methylthio) pyridin-3-yl) methyl)-3,8-diazabicyclo[3.2.1]octan-3-yl)pyridin-3-yl)pyrazolo [1,5-a]pyridine-3-carbonitrile

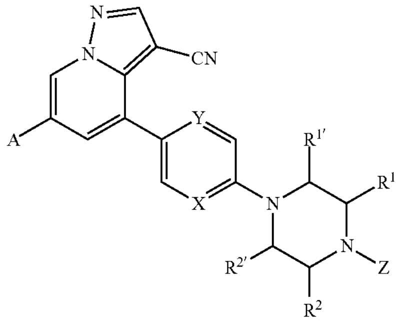

At 0° C., Intermediate 22 (45 mg) was dissolved in THE (15 mL), 6-(methylthio) pyridin-3-carbaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=15:1 (V:V)) to obtain the title compound (14 mg).

$^1$H NMR (400 MHz, $CDCl_3$) δ 8.69 (1H, d, J=1.6 Hz), 8.41 (1H, d, J=2.0 Hz), 8.35 (1H, d, J=2.4 Hz), 8.29 (1H, s), 8.12 (1H, s), 7.95 (1H, s), 7.72 (1H, dd, J=8.8 Hz, 2.4 Hz), 7.64 (1H, dd, J=8.4 Hz. 2.0 Hz), 7.39 (1H, d, J=1.6 Hz), 7.25 (1H, t, J=60.4 Hz), 7.18 (1H, d, J=8.4 Hz), 6.66 (1H, d, J=9.2 Hz), 3.88 (2H, d, J=10.4 Hz), 3.55 (2H, s), 3.28-3.34 (2H, m), 3.18 (2H, d, J=11.2 Hz), 2.58 (3H, s), 1.98-2.08 (2H, m), 1.75-1.81 (2H, m).

Example 74: 6-(1-(difluoromethyl)-1Hpyrazol-4-yl)-4-(6-(6-((6-(methylthio) pyridin-2-yl) methyl)-3,6-diazabicyclo[3.1.1]heptan-3-yl)pyridin-3-yl)pyrazolo[1,5-a]pyridine-3-carbonitrile

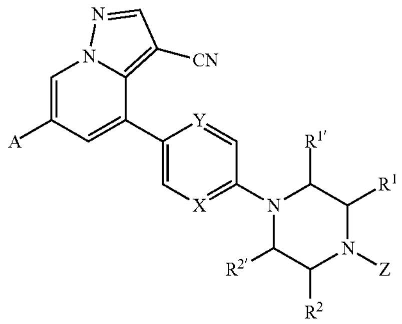

At 0° C., Intermediate 21 (43 mg) was dissolved in THE (10 mL), 6-(methylthio)picolinaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (20 mg).

$^1$H NMR (400 MHz, $CDCl_3$) δ 8.71 (1H, d, J=1.6 Hz), 8.44 (1H, d, J=2.4 Hz), 8.31 (1H, s), 8.14 (1H, s), 7.97 (1H, s), 7.82 (1H, dd, J=8.8 Hz. 2.4 Hz), 7.47 (1H, t, J=8.0 Hz), 7.42 (1H, d, J=1.6 Hz), 7.25 (1H, t, J=60.4 Hz), 7.12-7.17 (1H, m), 7.06 (1H, d, J=7.2 Hz), 6.73 (1H, d, J=8.4 Hz), 3.53-4.03 (8H, m), 2.73-2.93 (1H, m), 2.54 (3H, s), 1.73 (1H, d, J=8.8 Hz).

Example 75: 6-(1-(difluoromethyl)-1Hpyrazol-4-yl)-4-(6-(4-((6-(methylthio) pyridin-3-yl) methyl) piperazin-1-yl) pyridin-3-yl) pyrazolo[1,5-a] pyridine-3-carbonitrile

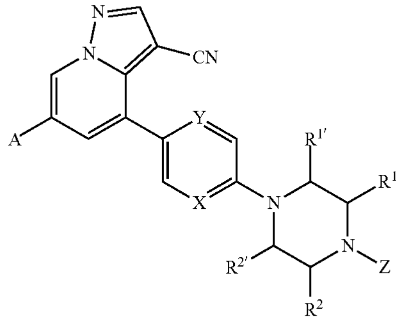

At 0° C., Intermediate 24 (42 mg) was dissolved in THF (10 mL). 6-(methylthio) pyridin-3-carbaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (36 mg).

$^1$H NMR (400 MHz, $CDCl_3$) δ 8.69 (1H, d, J=1.6 Hz), 8.39 (1H, d, J=1.6 Hz), 8.36 (1H, d, J=2.8 Hz), 8.29 (1H, s), 8.12 (1H, s), 7.96 (1H, s), 7.73 (1H, dd, J=8.8 Hz. 2.8 Hz), 7.54 (1H, dd, J=8.4 Hz, 2.0 Hz), 7.39 (1H, d, J=1.6 Hz), 7.25 (1H, t, J=60.4 Hz), 7.17 (1H, d, J=8.4 Hz), 6.76 (1H, d, J=8.8 Hz), 3.64-3.66 (4H, m), 3.51 (2H, s), 2.54-2.58 (7H, m).

Example 76: 6-(1-(methyl)-1Hpyrazol-4-yl)-4-(6-(6-((6-(methylsulfonyl) pyridin-3-yl) methyl)-3,6-diazabicyclo[3.1.1]heptan-3-yl)pyridin-3-yl)pyrazolo[1,5-a]pyridine-3-carbonitrile

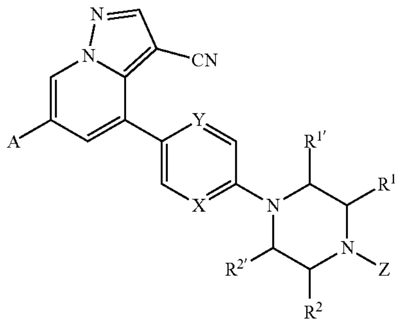

At 0° C., Intermediate 2 (42 mg) was dissolved in THF (10 mL), 6-(methylsulfonyl)nicotinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (21 mg).

$^1$H NMR (400 MHz, $CDCl_3$) δ 8.73 (1H, s), 8.65 (1H, d, J=1.6 Hz), 8.44 (1H, d, J=2.4 Hz), 8.28 (1H, s), 8.01-8.09 (2H, m), 7.82 (1H, dd, J=8.8 Hz, 2.4 Hz), 7.79 (1H, s), 7.69 (1H, s), 7.42 (1H, d, J=1.6 Hz), 6.71 (1H, d, J=8.8 Hz), 3.99 (3H, s), 3.77-3.84 (6H, m), 3.62-3.70 (2H, m), 3.23 (3H, s), 2.73-2.82 (1H, m), 1.71 (1H, d, J=8.4 Hz).

Example 77: 6-(1-(difluoromethyl)-1Hpyrazol-4-yl)-4-(6-(6-((6-(methylsulfonyl) pyridin-3-yl) methyl)-3,6-diazabicyclo[3.1.1]heptan-3-yl)pyridin-3-yl) pyrazolo[1,5-a]pyridine-3-carbonitrile

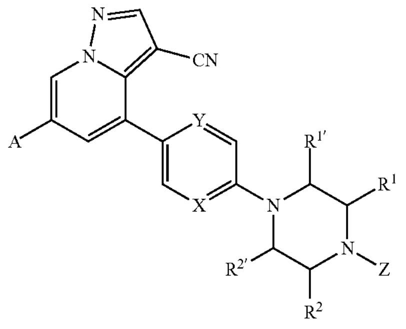

At 0° C., Intermediate 21 (43 mg) was dissolved in THF (10 mL). 6-(methylsulfonyl) nicotinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (23 mg).

$^1$H NMR (400 MHz, $CDCl_3$) δ 8.73 (1H, s), 8.72 (1H, d, J=1.6 Hz), 8.44 (1H, d, J=2.4 Hz), 8.31 (1H, s), 8.14 (1H, s), 8.04 (1H, d, J=7.6 Hz), 8.01 (1H, dd, J=7.6 Hz, 1.6 Hz), 7.97 (1H, s), 7.82 (1H, dd, J=9.2 Hz, 2.4 Hz), 7.43 (1H, d, J=1.6 Hz), 7.26 (1H, t, J=60.4 Hz), 6.71 (1H, d, J=8.4 Hz), 3.78-3.82 (4H, m), 3.76 (2H, s), 3.60-3.69 (2H, m), 3.23 (3H, s), 2.71-2.79 (1H, m), 1.70 (1H, d, J=8.8 Hz).

Example 78: 6-(1-(difluoromethyl)-1Hpyrazol-4-yl)-4-(6-(6-((5-(methylsulfonyl) pyridin-2-yl) methyl)-3,6-diazabicyclo[3.1.1]heptan-3-yl)pyridine-3-yl) pyrazolo[1,5-a]pyridine-3-carbonitrile

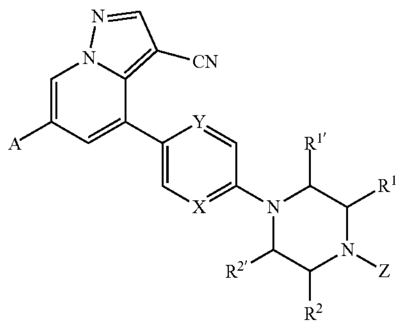

At 0° C. Intermediate 21 (43 mg) was dissolved in THE (10 mL). 5-(methyl sulfonyl) picolinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (26 mg).

$^1$H NMR (400 MHz, $CDCl_3$) δ 9.05 (1H, d, J=2.0 Hz), 8.71 (1H, d, J=1.6 Hz), 8.43 (1H, d, J=2.4 Hz), 8.30 (1H, s), 8.18 (1H, dd, J=8.0 Hz, 2.4 Hz), 8.14 (1H, s), 7.97 (1H, s), 7.80 (1H, dd, J=8.8 Hz, 2.4 Hz), 7.68 (1H, d, J=8.0 Hz), 7.42 (1H, d, J=1.6 Hz), 7.26 (1H, t, J=60.4 Hz), 6.72 (1H, d, J=8.8 Hz), 3.86-3.94 (6H, m), 3.61-3.71 (2H, m), 3.10 (3H, s), 2.76-2.84 (1H, m), 1.72 (1H, d, J=8.4 Hz).

Example 79: 6-(1-(methyl)-1Hpyrazol-4-yl)-4-(6-(6-((5-(methylsulfonyl)pyridin-2-yl) methyl)-3,6-diazabicyclo[3.1.1]heptan-3-yl)pyridin-3-yl)pyrazolo[1,5-a]pyridine-3-carbonitrile

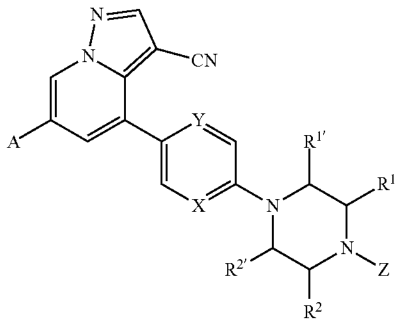

At 0° C., Intermediate 2 (42 mg) was dissolved in THE (10 mL), 5-(methyl sulfonyl) picolinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (28 mg).

$^1$H NMR (400 MHz, DMSO-d6) δ9.22 (1H, s), 8.94 (1H, s), 8.64 (1H, s), 8.43 (1H, s), 8.38 (1H, s). 8.28 (1H, d, J=7.6 Hz), 8.33 (1H s), 7.87 (1H, d, J=8.0 Hz), 7.78 (1H s), 7.75 (1H, d, J=8.4 Hz), 6.80 (1H, d, J=8.4 Hz), 3.86 (3H, s), 3.72-3.84 (6H, m), 3.48-3.64 (2H, m), 3.29 (3H, s), 2.42-2.52 (1H m), 1.60-1.70 (1H, m).

Example 80: 6-(1-(difluoromethyl)-1Hpyrazol-4-yl)-4-(6-(4-((5-(methylsulfonyl) pyridin-2-yl) methyl) piperazin-1-yl) pyridin-3-yl) pyrazolo[1,5-a] pyridine-3-carbonitrile

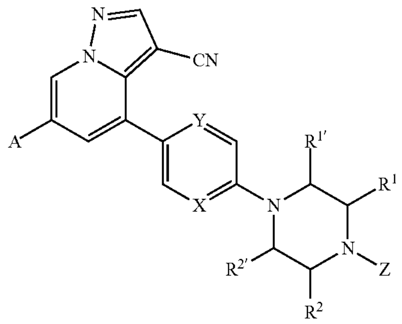

At 0° C., Intermediate 24 (42 mg) was dissolved in THE (10 mL), 5-(methyl sulfonyl) picolinaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (25 mg).

$^1$H NMR (400 MHz, $CDCl_3$) δ9.01 (1H, d, J=2.4 Hz), 8.70 (1H, d, J=1.6 Hz), 8.37 (1H, d, J=2.8 Hz), 8.29 (1H, s), 8.22 (1H, dd, J=8.4 Hz, 2.0 Hz), 8.13 (1H, s), 7.96 (1H, s), 7.73-7.76 (2H, m), 7.40 (1H, d, J=1.6 Hz), 7.25 (1H, t, J=60.4 Hz), 6.79 (1H, d, J=9.2 Hz), 3.84 (2H, s), 3.68-3.75 (4H, m). 3.13 (3H, s), 2.64-2.70 (4H, m).

Example 81: 4-(6-(4-(4-(methylthio)benzyl)piperazin-1-yl)pyridin-3-yl)-6-(1-(difluoro methyl)-1Hpyrazol-4-yl)pyrazolo[1,5-a]pyridine-3-carbonitrile

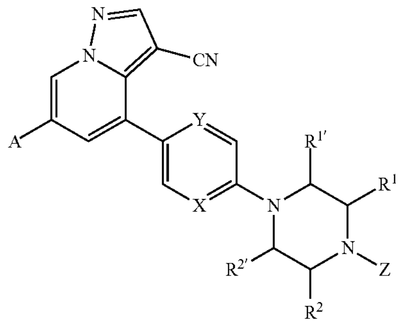

At 0° C., Intermediate 24 (42 mg) was dissolved in THF (10 mL), 4-(methylthio)benzaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (35 mg).

$^1$H NMR (400 MHz, $CDCl_3$) δ8.69 (1H, d, J=1.6 Hz), 8.36 (1H, d, J=2.8 Hz), 8.29 (1H, s), 8.12 (I H, s), 7.96 (1H, s), 7.73 (1H, dd, J=8.8 Hz. 2.8 Hz), 7.39 (1H, d, J=1.2 Hz), 7.27-7.31 (2H, m), 7.24 (1H, t, J=60.4 Hz), 7.23 (2H, d, J=8.4 Hz), 6.76 (1H, d, J=8.8 Hz), 3.62-3.70 (4H, m), 3.53 (2H, s). 2.54-2.60 (4H, m), 2.49 (3H, s).

Example 82: 6-(1-difluoromethyl-1Hpyrazol-4-yl)-4-(6-(6-(4-(methylthio)benzyl)-3,6-diaza bicyclo [3.1.1]heptan-3-yl)pyridin-3-yl)pyrazolo[1,5-a]pyridine-3-carbonitrile

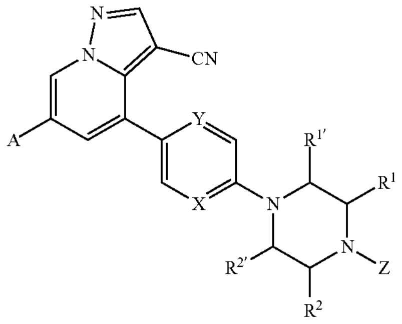

At 0° C. Intermediate 21 (43 mg) was dissolved in THE (20 mL), 4-(methylthio)benzaldehyde (31 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1$H NMR (400 MHz, $CDCl_3$) δ8.73 (1H, s), 8.46 (1H, s), 8.31 (1H, s), 8.15 (1H, s), 7.98 (1H, s), 7.85 (1H, d, J=7.2 Hz), 7.47-7.55 (2H, m), 7.44 (1H, d, J=1.2 Hz), 7.25-7.26 (2H, m), 7.24 (H, t. J=60.4 Hz), 6.73 (1H, d, J=9.2 Hz), 4.13-4.37 (2H, m), 3.78-4.10 (6H, m), 3.10-3.38 (1H, m), 2.47 (3H, s), 1.80-1.90 (1H, m)

Example 83: 4-(6-(6-(4-nitrobenzyl)-3,6-diazabicyclo[3.1.1]heptan-3-yl)pyridin-3-yl)-6-(1-(difluoro methyl)-1Hpyrazol-4-yl)pyrazolo[1,5-a]pyridine-3-carbonitrile

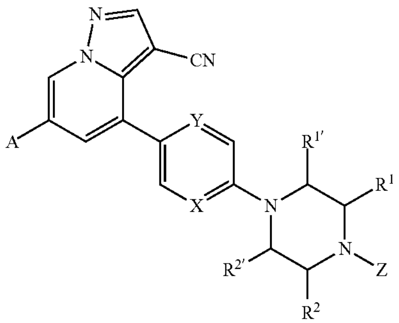

At 0° C., Intermediate 21 (43 mg) was dissolved in THE (20 mL), 4-nitrobenzaldehyde (30 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (34 mg).

$^1H$ NMR (400 MHz, $CDCl_3$) δ8.72 (1H, d, J=1.6 Hz), 8.44 (1H, d, J=2.8 Hz), 8.31 (1H, s), 8.18 (2H, d, J=8.8 Hz), 8.13 (1H, s), 7.97 (1H, s), 7.82 (1H, dd, J=8.8 Hz, 2.8 Hz), 7.58 (2H, d, J=7.6 Hz), 7.43 (1H, d, J=1.2 Hz), 7.26 (1H, t, J=60.4 Hz), 6.71 (1H, d, J=8.8 Hz), 3.73-3.88 (6H, m), 3.59-3.68 (2H, m), 2.72-2.82 (1H, m), 1.70 (1H, d, J=9.2 Hz).

Example 84: 4-(6-(6-(4-(methylsulfonyl)benzyl)-3,64-diazabicyclo[3.1.1]heptan-3-yl) pyridin-3-yl)-6-(1-(trifluoromethyl)-1Hpyrazol-4-yl) pyrazolo[1,5-a]pyridine-3-carbonitrile

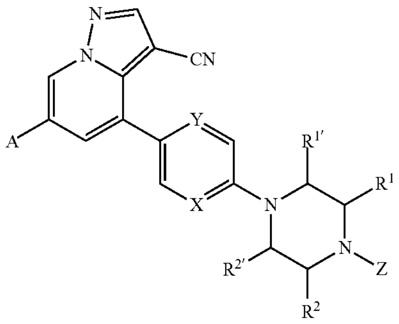

At 0° C. Intermediate 25 (45 mg) was dissolved in THF (20 mL), 4-(methyl sulfonyl) benzaldehyde (37 mg) and sodium triacetoxyborohydride (100 mg) were sequentially added, and the mixture was let warm up to room temperature and stirred for 12 hours. The reaction solution was poured into an aqueous solution of saturated sodium bicarbonate (50 mL), the mixture was extracted with dichloromethane, the extract was washed with brine, dried over anhydrous sodium sulphate and filtered, the filtrate was concentrated under reduced pressure, and the residue was purified through Thin Layer Chromatography (developing solvent: dichloromethane:methanol=20:1 (V:V)) to obtain the title compound (33 mg).

$^1H$ NMR (400 MHz, $CDCl_3$) δ8.72 (1H, d, J=1.6 Hz), 8.44 (1H, d, J=2.4 Hz), 8.32 (1H, s), 8.13 (1H, s), 8.07 (1H, s), 7.89 (2H, d, J=8.4 Hz), 7.81 (1H, dd, J=8.8 Hz, 2.4 Hz), 7.60 (2H, d, J=8.4 Hz), 7.41 (1H, d, J=1.2 Hz), 6.71 (1H, d, J=8.4 Hz), 3.78-3.84 (4H, m), 3.74 (2H, s), 3.58-3.68 (2H, m), 3.05 (3H, s), 2.72-2.78 (1H, m), 1.69 (1H, d, J=8.4 Hz),

Bioactivity Assay

Assay for Bioactivity of RET Compounds

1. In Vitro Enzymatic Activity Assay for Compounds on $RET^{WT}$

The compounds in this invention inhibited the enzymatic activity of $RET^{WT}$ with $IC_{50}$ values determined by homogeneous time-resolved fluorescence (HTRF) assay. The compounds were diluted 5-fold with 100% DMSO starting from 0.2 mM (7 concentrations in total), and 2 μL of each concentration was added to 48 μL of reaction buffer (50 mM HEPES pH7.5, 0.1 mM $Na_3VO_4$, 5 mM $MgCl_2$. 1 mM DTT, 0.001% Tween 20, and 100 μg/ml BSA) for dilution and mixing. 2.5 μL of compounds and 5 μL of GST-$RET^{WT}$ (658-1114 aa, final concentration of 0.5 nM) were added to a 384-well plate (OptiPlate-384, purchased from PerkinElmer), the mixture was mixed by centrifugation, and 2.5 μL of ATP (final concentration of 25 μM) and TK Peptide Substrate mixture (final concentration of 1 μM, purchased from Cisbio) were added to start the reaction, with a total reaction volume of 10 μL.

The 384-well plate was placed in an incubator and reacted at 23° C. for 2 h before the reaction was stopped by the addition of 5 μL of TK Antibody (purchased from Cisbio) and 5 μL of Streptavidin-XL665 (purchased from Cisbio). After further incubation in the incubator for 1 h, fluorescence values (excitation at 320 nm, detecting emitted light at 665 nm and 620 nm, and a ratio of the two as an enzyme activity signal) were read on Envision (purchased from PerkinElmer). The enzymatic activity signal of $RET^{WT}$ was measured at 7 concentrations for each compound and the data were calculated using GraphPad Prism software to obtain the $IC_{50}$ value for the compound.

2. In Vitro Enzymatic Activity Assay for Compounds on $RET^{V804M}$

The compounds in this invention inhibited the enzymatic activity of $RET^{V804M}$ with $IC_{50}$ values determined by homogeneous time-resolved fluorescence (HTRF) assay. The compounds were diluted 5-fold with 100% DMSO starting from 0.2 mM (7 concentrations in total), and 2 μL of each concentration was added to 48 μL of reaction buffer (50 mM HEPES pH7.5, 0.1 mM $Na_3VO_4$, 5 mM $MgCl_2$. 1 mM DTT. 0.001% Tween 20, 20 nM SEB (purchased from Cisbio), and 100 μg/mi BSA) for dilution and mixing. 2.5 μL of compounds and 5 μL of GST-$RET^{V804M}$ (658-1114 aa, final concentration of 0.02 nM) were added to a 384-well plate (OptiPlate-384, purchased from PerkinElmer), the mixture was mixed by centrifugation, and 2.5 μL of ATP (final concentration of 1.5 μM) and TK Peptide Substrate mixture (final concentration of 1 μM, purchased from Cisbio) were added to start the reaction, with a total reaction volume of 10 μL. The 384-well plate was placed in an incubator and reacted at 23° C. for 1 h before the reaction was stopped by the addition of 5 μL of TK Antibody (purchased from Cisbio) and 5 μL of Streptavidin-XL665 (purchased from Cisbio). After further incubation in the incubator for 1 h, fluorescence values (excitation at 320 nm, detecting emitted light at 665 run and 620 nm, and a ratio of the two as an enzyme activity signal) were read on Envision (purchased from PerkinElmer). The enzymatic activity signal of $RET^{V804M}$ was measured at 7 concentrations for each compound and the data were calculated using GraphPad Prism software to obtain the $IC_{50}$ value for the compound.

3. n Vitro Enzymatic Activity Assay for Compounds on VEGFR2

The compounds in this invention inhibited the enzymatic activity of VEGFR2 with $IC_{50}$ values determined by homogeneous time-resolved fluorescence (HTRF) assay. The compounds were diluted 5-fold with 100% DMSO starting from 1 mM (7 concentrations in total), and 2 μL of each concentration was added to 48 μL of reaction buffer (50 mM HEPES pH 7.5, 0.1 mM $Na_3VO_4$, 5 mM $MgCl_2$, 1 mM $MnCl_2$, 1 mM DTT, 0.001% Tween 20, and 100 μg/ml BSA) for dilution and mixing. 2.5 μL of compounds and 5 μL of GST-VEGFR2 (final concentration of 0.1 nM) were added to a 384-well plate (OptiPlate-384, purchased from PerkinElmer), the mixture was mixed by centrifugation, and 2.5 μL of ATP (final concentration of 2.5 μM) and TK Peptide Substrate mixture (final concentration of 1 μM, purchased from Cisbio) were added to start the reaction, with a total reaction volume of 10 μL. The 384-well plate was placed in an incubator and reacted at 23° C. for 1.5 h before the reaction was stopped by the addition of 5 μL of TK Antibody (purchased from Cisbio) and 5 μL of Streptavidin-XL665 (purchased from Cisbio). After further incubation in the incubator for 1 h. fluorescence values (excitation at 320 nm, detecting emitted light at 665 nm and 620 nm, and a ratio of the two as an enzyme activity signal) were read on Envision (purchased from PerkinElmer). The enzymatic activity signal of VEGFR2 was measured at 7 concentrations for each compound and the data were calculated using GraphPad Prism software to obtain the $IC_{50}$ value for the compound.

4. Determination of TT Cell Proliferation Activity of Compounds

TT cells, a human thyroid carcinoma cell line, were cultured in Ham's F-12K medium supplemented with 15% fetal bovine serum (FBS, purchased from Biological Industries, BI) and 1% penicillin/streptomycin double antibody (P/S, purchased from Life Technology) under conditions of 37° C. and 5% $CO_2$. TT cells were plated in a 96-well plate (#3917 purchased from Corning) at a concentration of 5000 cells/195 μL/well the day before compound was detected. The compounds were diluted 3-fold with 100% DMSO starting from 10 mM (10 concentrations in total) after 24 h, and 2 μL of each concentration was diluted in 48 μL of Ham's F-12K medium. 5 μL of each diluted compound was added to the plated Cell suspension, the compound and cells were co-incubated in a cell incubator for 120 h (5 days), after the medium was aspirated. 25 μL of Cell-Titer Glo (G7570, purchased from Promega) reagent was added and re-incubated for 5-10 min. Fluorescence value was then read on Envision and the data were calculated using GraphPad Prism software to obtain $IC_{50}$ values for inhibition of cell proliferation by the compounds.

5. Determination of Cell Proliferation Activity of Compounds in KIF5B-RET/HEK293T Cells RET fusion form cell line KIF5B-RET/HEK293T cells constructed by slow virus infection were cultured in a DMEM culture medium supplemented with 10% fetal bovine serum (FBS, purchased from Biological Industries, BI) and 1% penicillin/streptomycin double antibody (P/S, purchased from Life Technology) under the culture conditions of 37° C. and 5% $CO_2$. KIF5B-RET/HEK293T cells were plated in a 96-well plate (#3917 purchased from Corning) at a concentration of 2000 cells/195 μL/well the day before compound was detected. The compounds were diluted 3-fold with 100% DMSO starting from 10 mM (10 concentrations in total) after 24 h, and 2 μL of each concentration was diluted in 48 μL of DMEM medium. 5 μL of each diluted compound was added to the plated Cell suspension, the compound and cells were co-incubated in a cell incubator for 72 h (3 days), after the medium was aspirated, 25 μL of Cell-Titer Glo (G7570, purchased from Promega) reagent was added and re-incubated for 5-10 min. Fluorescence value was then read on Envision and the data were calculated using GraphPad Prism software to obtain $IC_{50}$ values for inhibition of cell proliferation by the compounds.

Protein Activity and Cytological Data

| Compound No. | $RET^{wt}$ $IC_{50}$ (nM) | $RET^{V804M}$ $IC_{50}$ (nM) | VEGFR2 $IC_{50}$ (nM) | TT (Cell) $IC_{50}$ (nM) | KIFSB-$RETV^{804M}$/293T (Cell)$IC_{50}$ (nM) |
|---|---|---|---|---|---|
| Example 1 | 0.352 | 1.21 | 4.49 | — | — |
| Example 2 | 0.108 | 0.906 | 13.4 | 26.1 | — |
| Example 3 | 0.076 | 0.305 | 3.01 | 1.01 | — |
| Example 6 | 0.332 | 1.25 | 8.91 | 13.8 | — |
| Example 7 | 0.601 | — | 9.67 | 7.41 | 99.1 |
| Example 8 | 0.863 | 0.908 | 9.15 | 14.0 | 162 |
| Example 9 | 0.565 | 1.22 | 10.0 | 37.3 | 371 |
| Example 10 | 1.08 | 1.02 | 13.9 | 23.8 | — |
| Example 11 | 1.73 | — | 37.0 | — | — |
| Example 12 | 0.650 | 1.47 | 14.4 | 6.30 | 141 |
| Example 13 | 0.421 | 0.332 | 3.44 | — | — |
| Example 14 | 0.762 | 0.629 | 1.55 | — | — |
| Example 15 | 0.186 | 0.206 | 11.8 | 17.8 | — |
| Example 16 | 0.433 | 0.872 | 8.95 | 36.7 | — |
| Example 17 | 0.255 | 1.01 | 14.1 | — | 394 |
| Example 18 | 0.424 | 1.72 | 13.0 | — | — |
| Example 19 | 0.636 | — | 94.0 | — | — |
| Example 20 | 0.092 | 0.237 | 6.44 | 6.58 | 146 |
| Example 21 | 0.078 | 1.21 | 11.9 | 27.9 | — |
| Example 22 | 0.124 | 0.242 | — | 12.9 | 147 |
| Example 23 | 0.2.56 | 0.885 | 4.40 | 17.1 | 352 |
| Example 24 | 0.2.29 | — | — | — | — |
| Example 25 | 0.148 | 0.236 | — | 5.96 | 146 |
| Example 26 | 0.422 | — | 95.5 | — | — |
| Example 27 | 0.536 | — | 2.28 | — | — |
| Example 28 | 0.757 | 2.50 | — | — | — |
| Example 30 | 0.680 | 1.11 | — | — | — |
| Example 32 | 0.800 | 3.19 | 29.1 | 48.7 | — |
| Example 33 | 0.944 | 2.84 | 7.50 | — | — |
| Example 34 | 0.391 | 3.17 | 13.4 | — | — |
| Example 35 | 0.172 | 1.47 | 9.60 | — | — |
| Example 36 | 0.179 | 2.58 | 16.9 | — | — |
| Example 38 | 0.419 | — | 40.3 | — | — |
| Example 40 | 1.31 | — | — | — | — |
| Example 41 | 0.352 | 1.04 | 17.3 | 18.2 | — |
| Example 42 | 0.642 | — | 42.5 | 47.9 | — |
| Example 43 | 0.132 | 0.507 | 13.4 | 16.4 | — |
| Example 44 | 0.247 | — | — | — | — |
| Example 45 | 0.159 | 0.822 | 4.96 | 22.7 | — |
| Example 46 | 0.159 | — | 17.2 | 37.6 | — |
| Example 47 | 0.343 | 2.48 | 16.9 | 53.1 | — |
| Example 48 | 0.57 | — | 10.1 | — | — |
| Example 49 | 0.94 | — | 18.2 | — | — |
| Example 50 | 0.181 | — | — | — | — |
| Example 51 | 0.328 | — | 6.20 | — | — |
| Example 53 | 0.072 | 0.807 | 2.46 | 14.6 | — |
| Example 54 | 1.07 | — | 10.1 | — | — |
| Example 55 | 0.109 | 0.976 | 19.6 | 15.4 | — |
| Example 56 | 0.080 | 1.78 | 59.0 | 39.9 | — |
| Example 57 | 0.178 | 2.86 | 8.94 | — | — |
| Example 58 | 1.34 | — | — | — | — |
| Example 59 | 0.066 | — | 0.154 | — | — |

-continued

| Compound No. | $RET^{wt}$ $IC_{50}$ (nM) | $RET^{V804M}$ $IC_{50}$ (nM) | VEGFR2 $IC_{50}$ (nM) | TT (Cell) $IC_{50}$ (nM) | KIFSB-$RETV^{804M}$/293T (Cell)$IC_{50}$ (nM) |
|---|---|---|---|---|---|
| Example 60 | 0.103 | 0.593 | 3.10 | 18.5 | 281 |
| Example 61 | 0.779 | 6.37 | 18.2 | — | — |
| Example 62 | 1.11 | — | — | — | — |
| Example 63 | 2.96 | — | — | — | — |
| Example 64 | 0.493 | 1.71 | 15.5 | 42.2 | — |
| Example 65 | 0.67 | 1.85 | 19.4 | 24.1 | 349 |
| Example 66 | 0.268 | — | 2.94 | — | — |
| Example 67 | 0.465 | 3.97 | 80.5 | — | — |
| Example 68 | 0.202 | 0.458 | 4.83 | 17.5 | 201 |
| Example 69 | 0.716 | 5.47 | 63.1 | — | — |
| Example 70 | 0.324 | 2.52 | 55.7 | — | — |
| Example 71 | 0.363 | — | 2.35 | — | — |
| Example 72 | 0.147 | 0.735 | 7.74 | 24.9 | 387 |
| Example 73 | 0.753 | 5.89 | 65.4 | — | — |
| Example 74 | 0.676 | 4.19 | 14.4 | — | — |
| Example 75 | 0.943 | — | — | — | — |
| Example 76 | 0.296 | 0.479 | 2.81 | 16.6 | — |
| Example 77 | 0.468 | 0.791 | 7.56 | 23.1 | — |
| Example 78 | 0.387 | 1.04 | 10.4 | 28.2 | — |
| Example 79 | 0.331 | 0.640 | 5.21 | 21.3 | — |
| Example 80 | 1.58 | — | — | — | — |
| Example 81 | 1.33 | — | — | — | — |
| Example 82 | 0.136 | — | 0.734 | — | — |
| Example 83 | 0.120 | — | 4.59 | — | — |
| Example 84 | 0.309 | — | 13.3 | — | — |

"—"means not tested

6. Pharmacokinetic Data of Compounds

Male SD rats (Beijing Vital River Laboratory Animal Technology Co., Ltd) were divided into groups. 3 in each group, received intragastric administration with the suspension of the test sample (5 mg/kg, suspensions MC 0.5%), respectively. Animals were fasted overnight prior to the experiment from 10 h before dosing to 4 h after dosing. Blood was collected 0.25, 0.5, 1, 2, 4, 6, 8, and 24 h after administration, respectively. After isoflurane anesthesia using a small animal anesthesia machine, 0.3 mL of whole blood samples was taken through the fundus venous plexus, placed in a heparin anticoagulant tube, and were centrifuged at 4° C. 4000 rpm for 5 min plasma was transferred to the centrifuge tube, and stored at −80° C. until analysis. Samples in the plasma were extracted using protein precipitation and the extracts were analyzed by LC/MS.

| Compound No. | Dose (mg/kg) | $T_{1/2}$ (hr) | Tmax (hr) | Cmax (ng/mL) | $AUC_{0\text{-}inf}$ (hr*ng/mL) |
|---|---|---|---|---|---|
| Example 7 | 5 | 3.53 | 2.00 | 1456 | 12597 |
| Example 9 | 5 | 2.02 | 2.17 | 1659 | 8293 |
| Example 10 | 5 | 3.38 | 4.00 | 1490 | 15308 |
| Example 15 | 5 | 3.56 | 1.17 | 1329 | 6651 |
| Example 16 | 5 | 4.08 | 4.00 | 3791 | 42694 |
| Example 26 | 5 | 4.90 | 1.75 | 6002 | 45048 |
| Example 45 | 5 | 3.21 | 1.83 | 3557 | 27473 |
| Example 60 | 5 | 7.45 | 1.50 | 1145 | 14720 |
| Example 84 | 5 | 2.78 | 2.00 | 3092 | 27264 |

INDUSTRIAL APPLICABILITY

The present invention provides a selective RET inhibitor and preparation therefor and use thereof. The present invention also provides a series of compounds represented by Formula (I) and pharmaceutically acceptable salts, solvates, polymorphs or isomers thereof, pharmaceutical compositions comprising these compounds, and a method of treating diseases with such compounds. The RET selective inhibitor provided by the invention has high activity, strong drug resistance and small clinical side effect, can effectively overcome the drug resistance problem of tumor treatment, and has better economic value and application prospect.

The invention claimed is:

1. A compound selected from below:

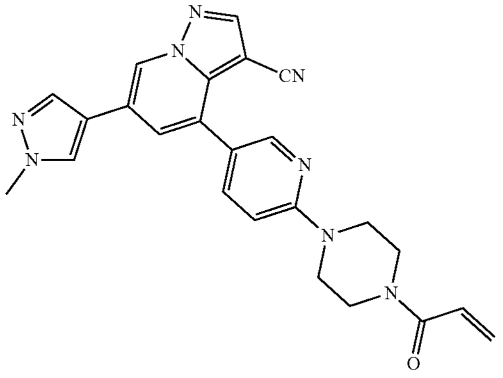

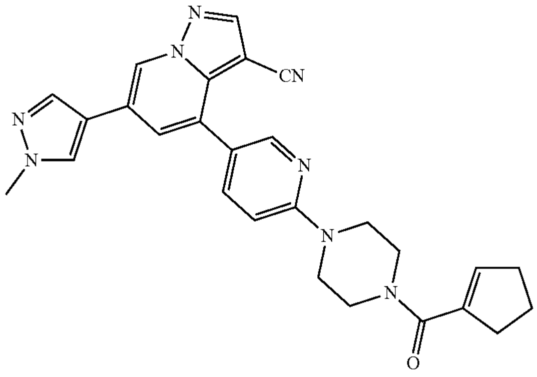

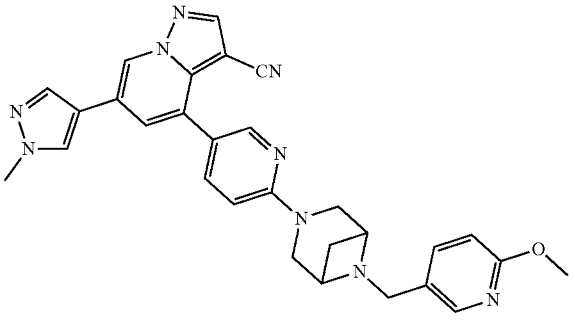

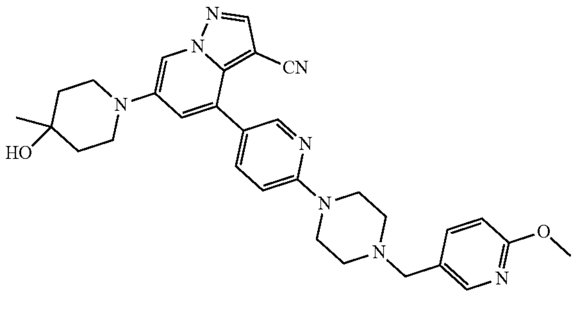

-continued
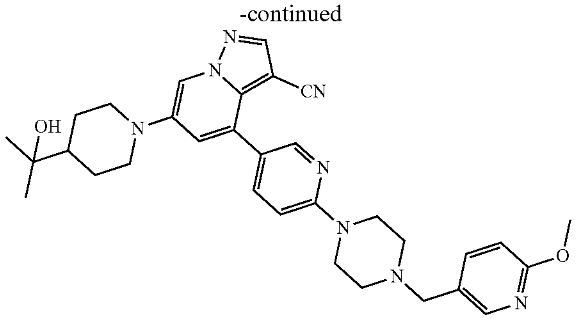
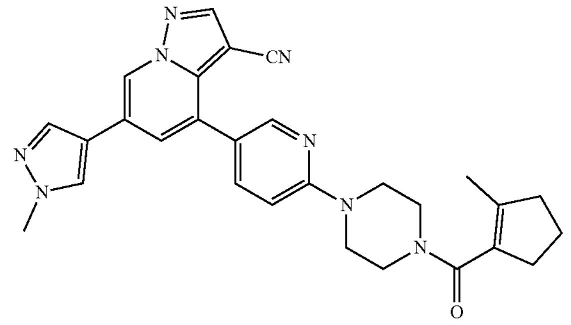
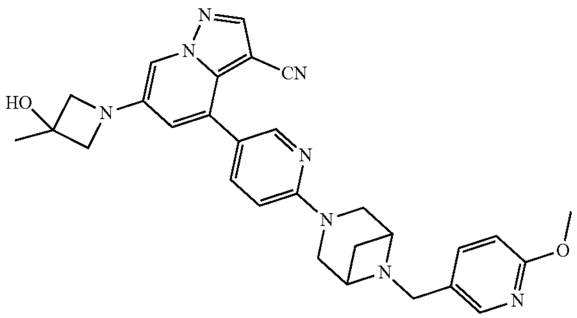
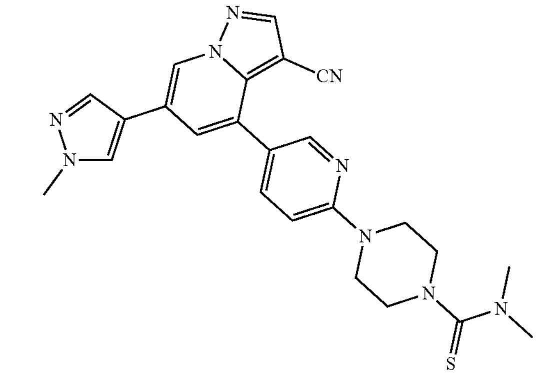
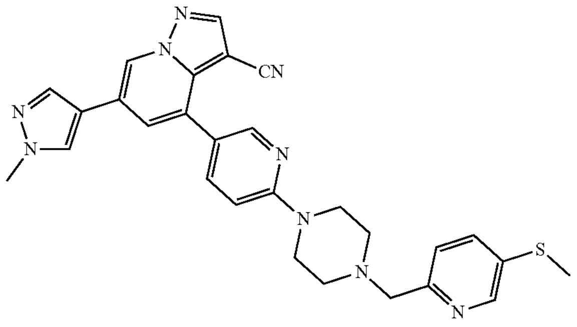
-continued
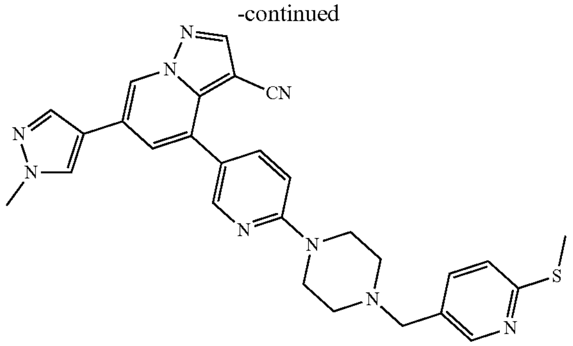
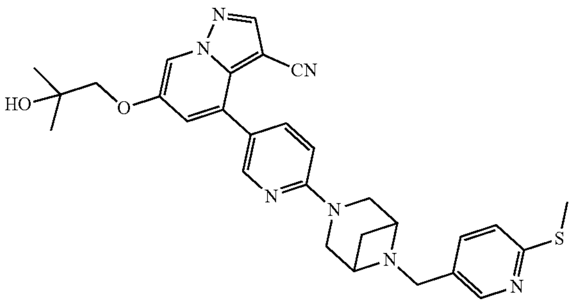
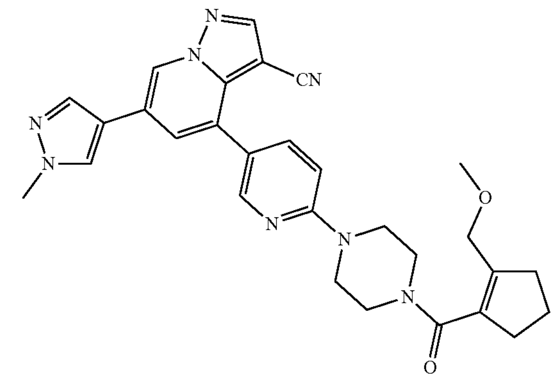
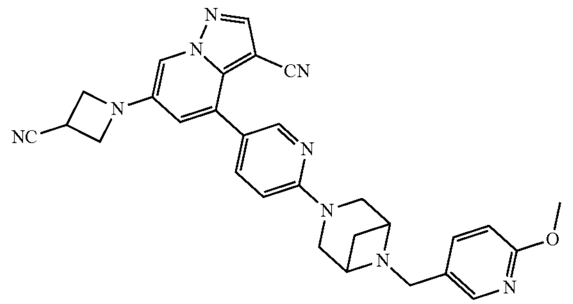
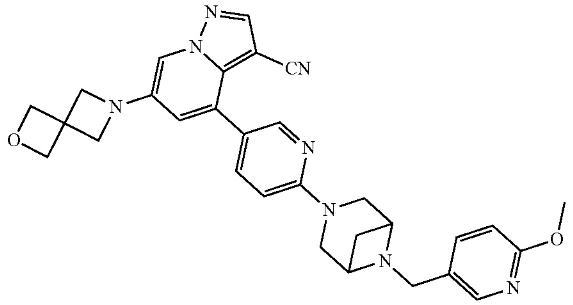

-continued
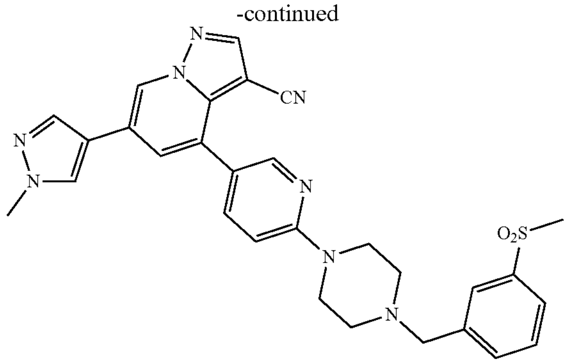
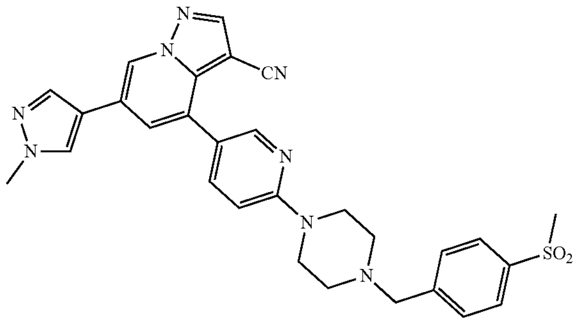
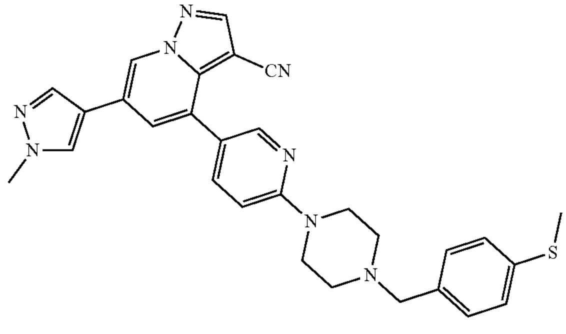
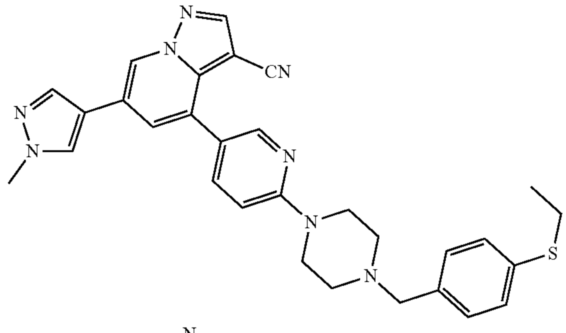
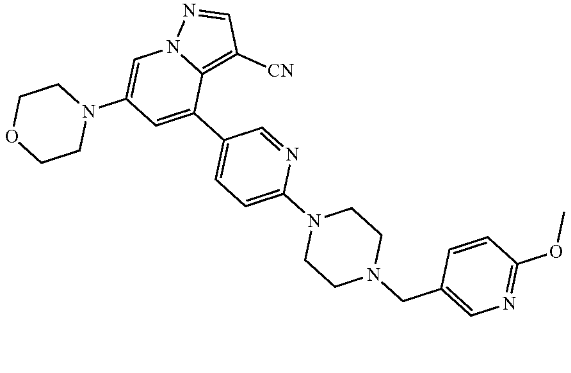
-continued
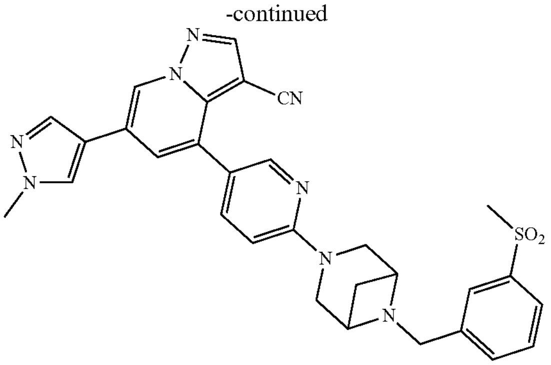
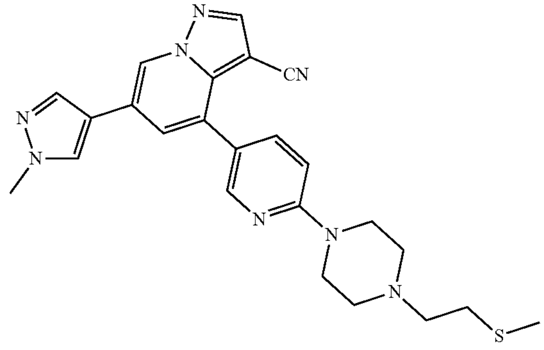
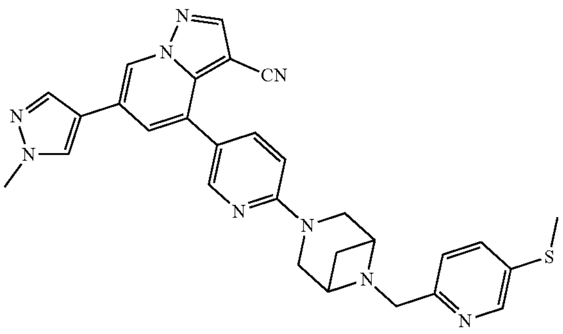
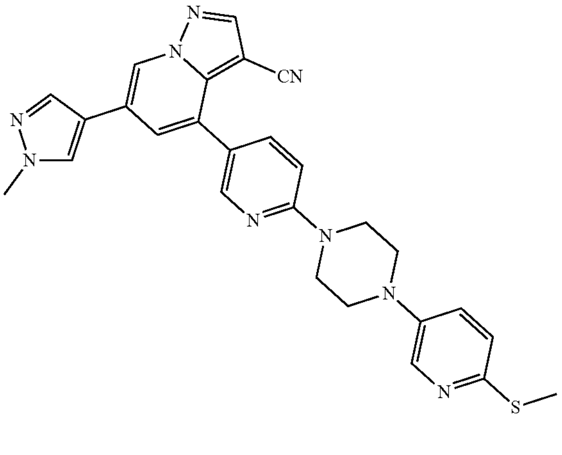

-continued
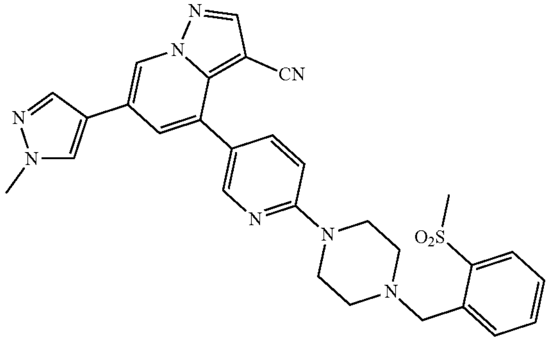
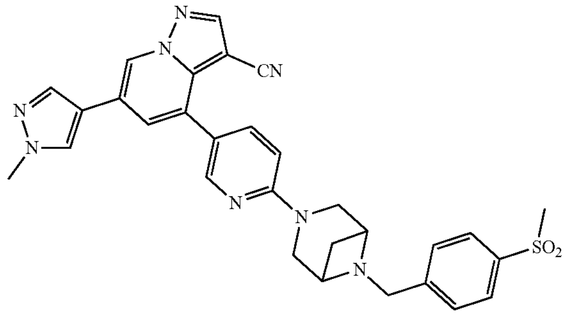
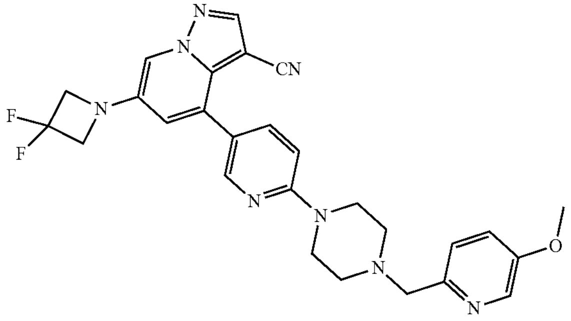
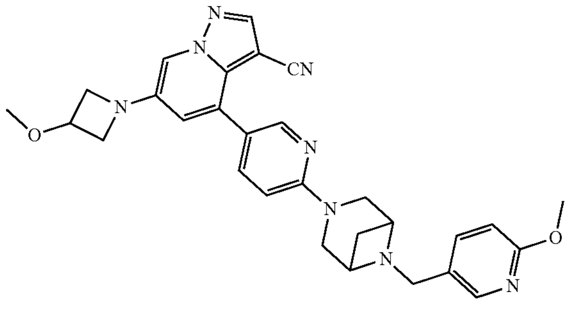
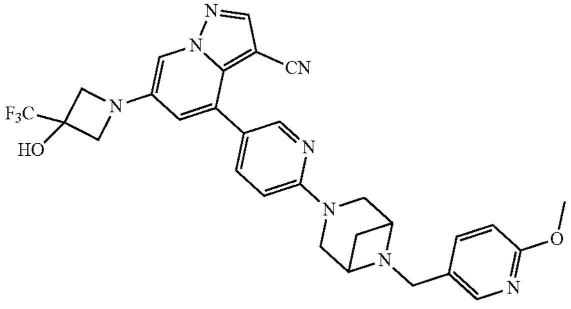
-continued
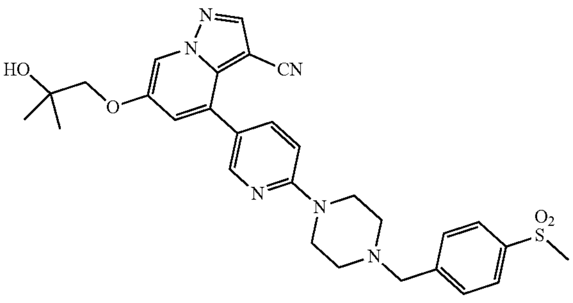
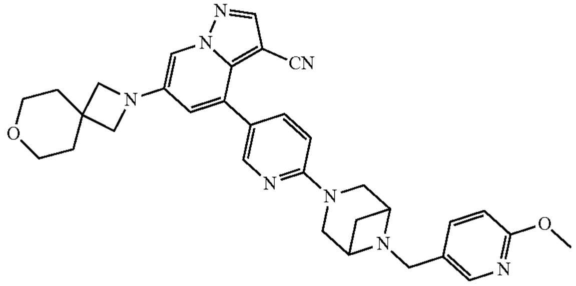
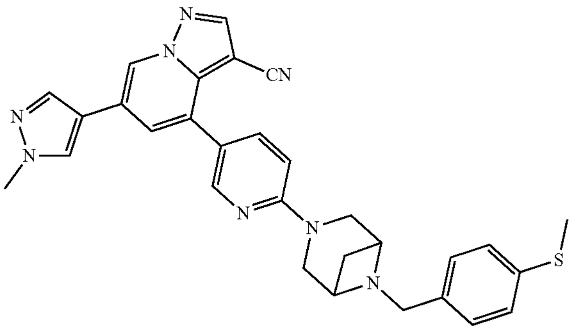
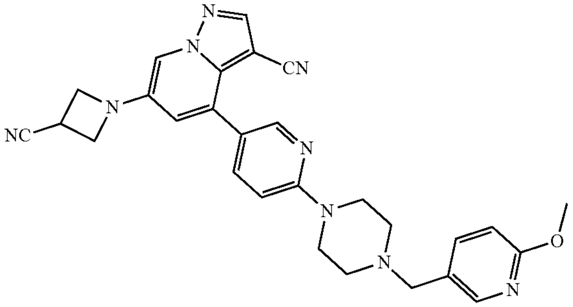
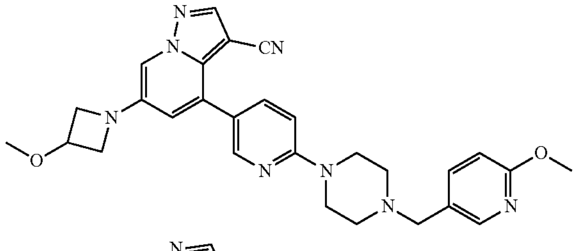
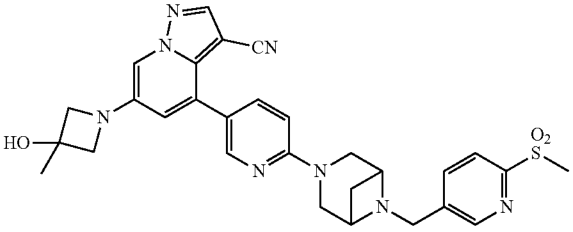

-continued
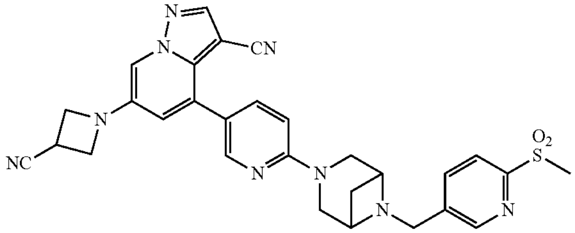
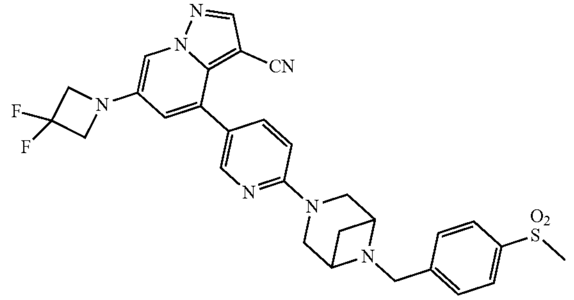
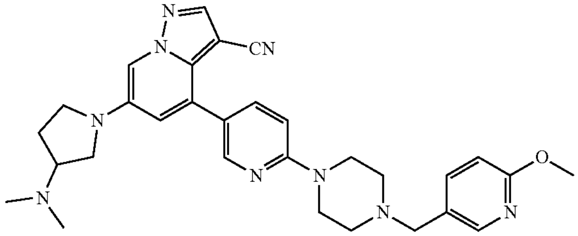
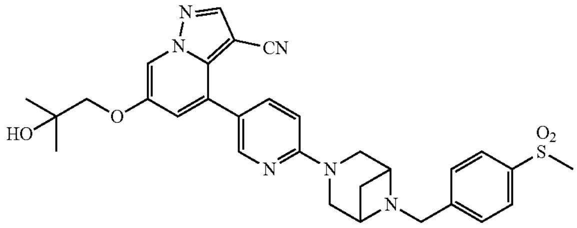
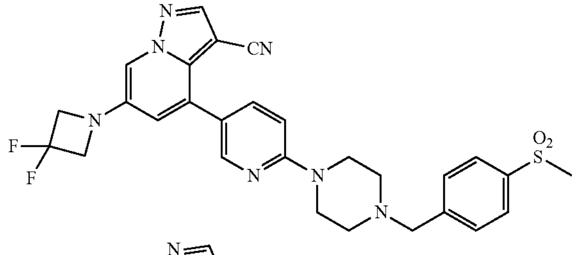
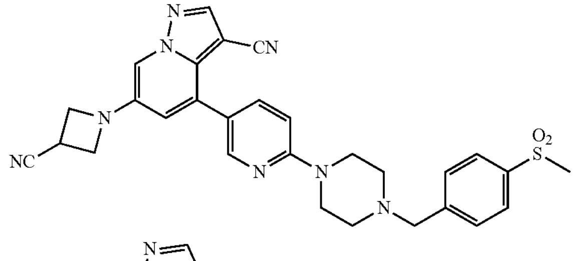
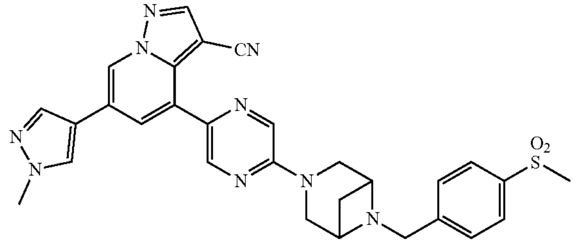
-continued
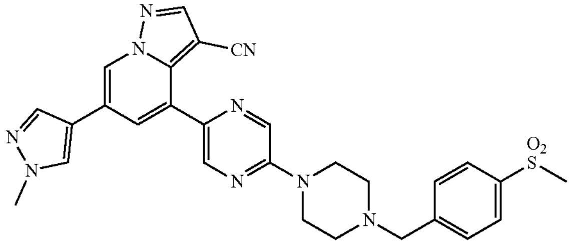
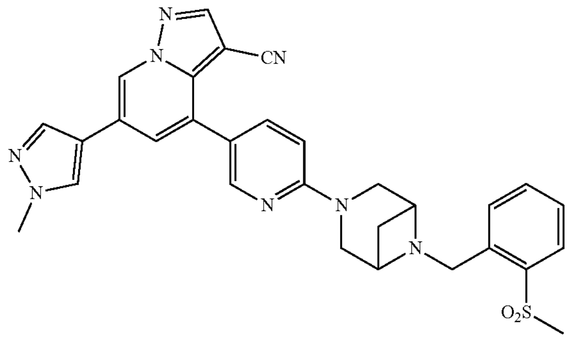
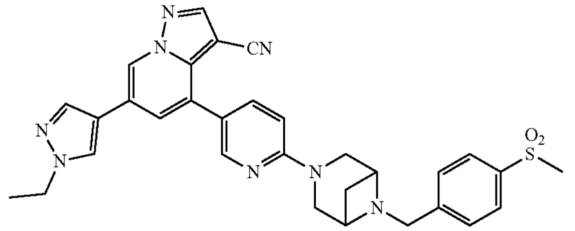
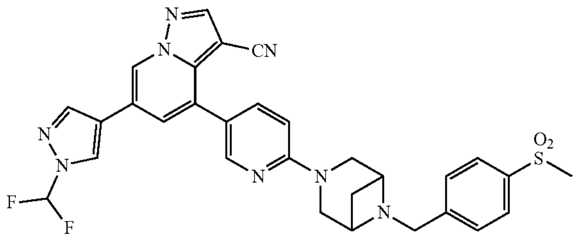
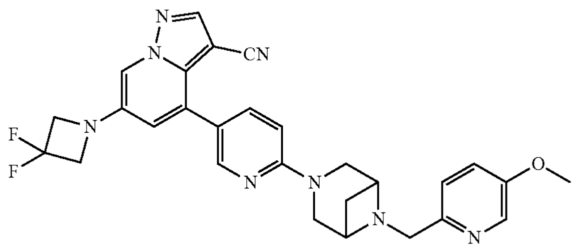
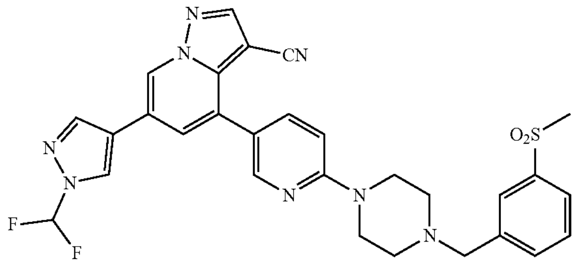

-continued
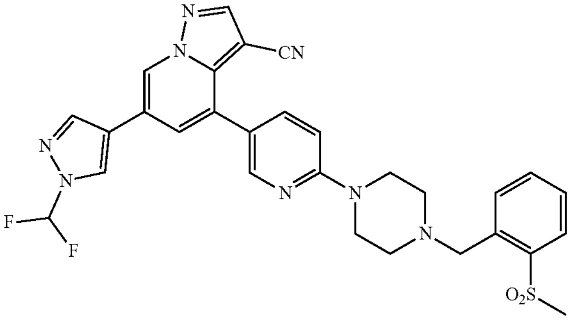
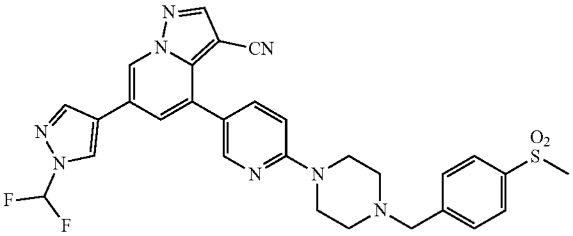
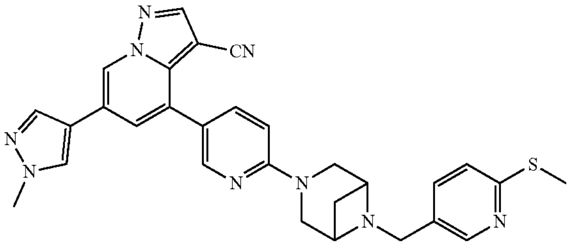
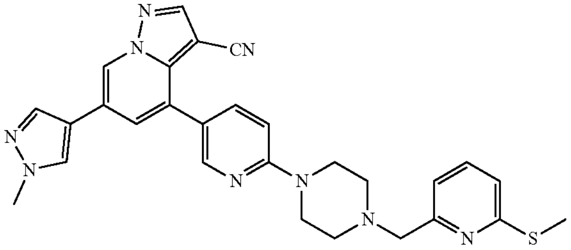
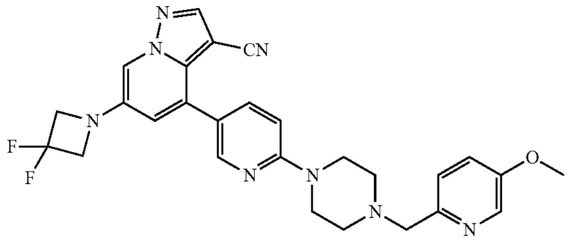
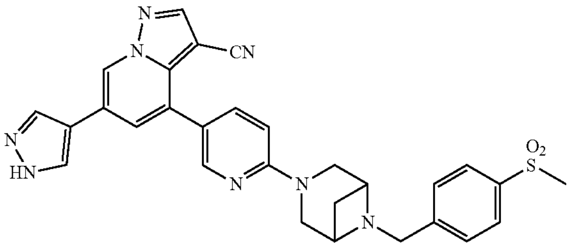
-continued
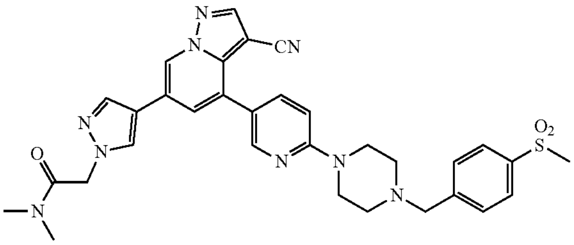
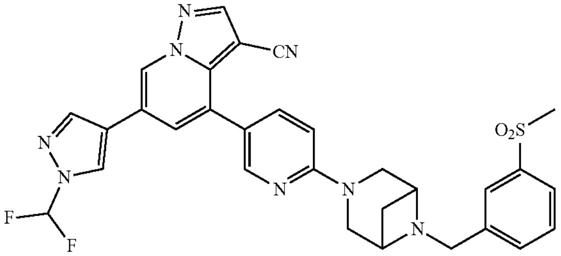
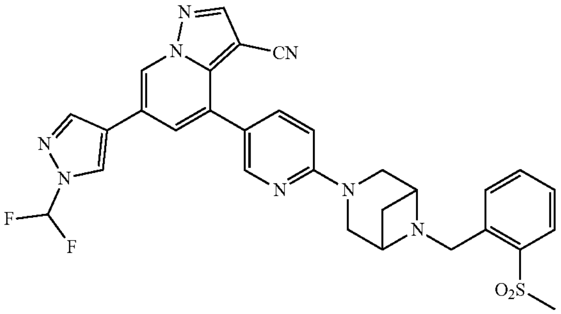
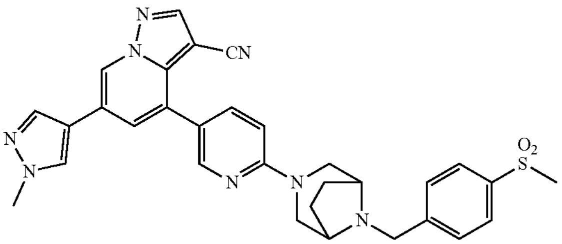
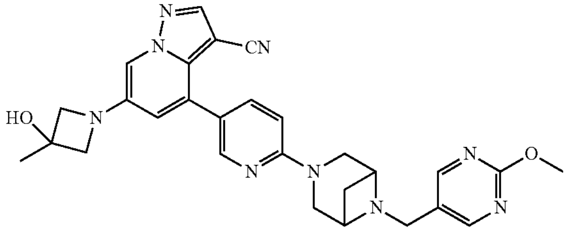
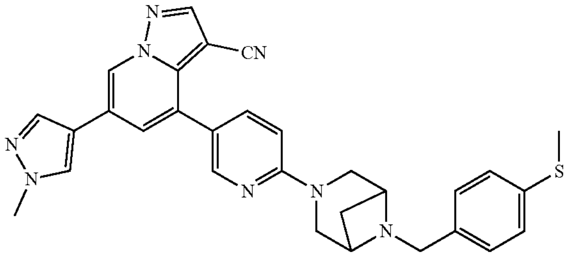

-continued
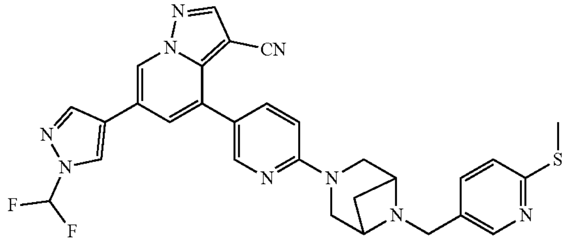
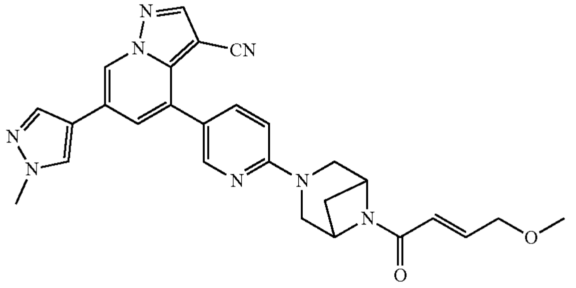
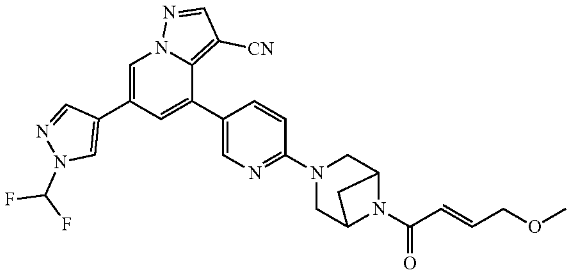
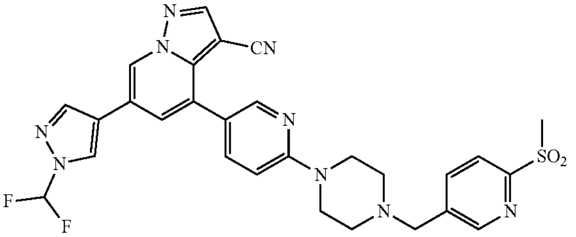
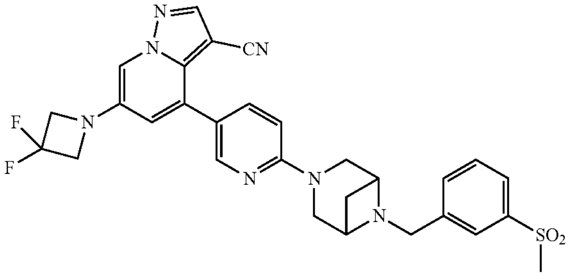
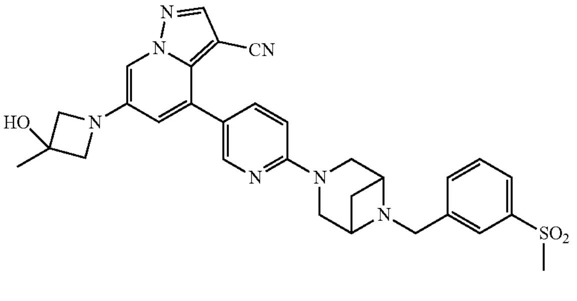
-continued
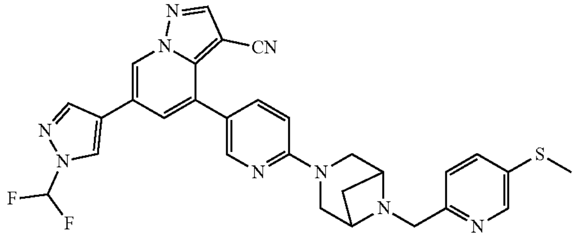
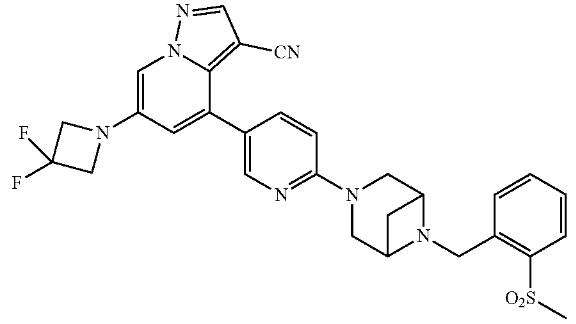
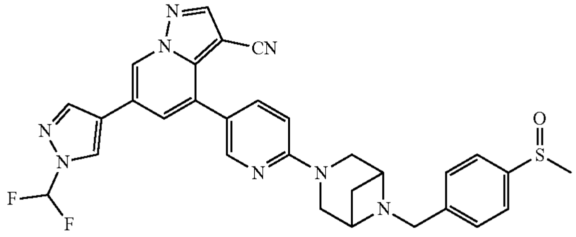
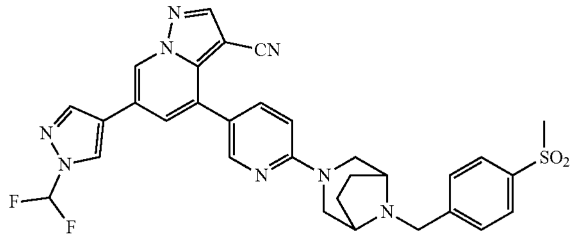
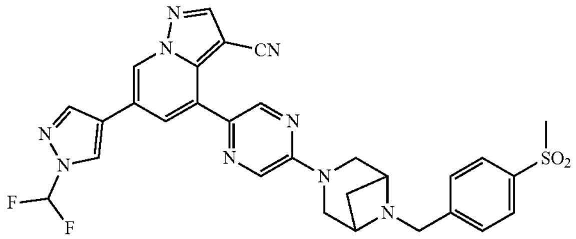
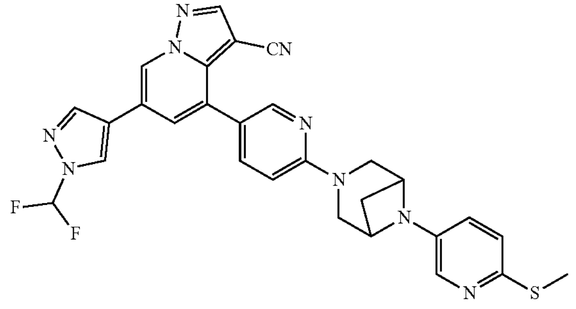

-continued
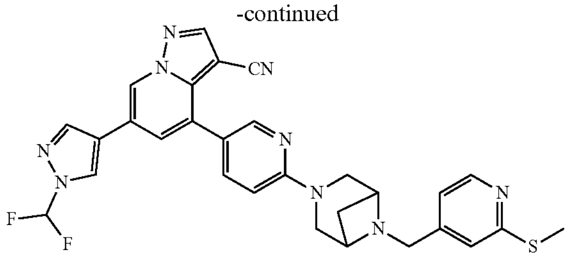
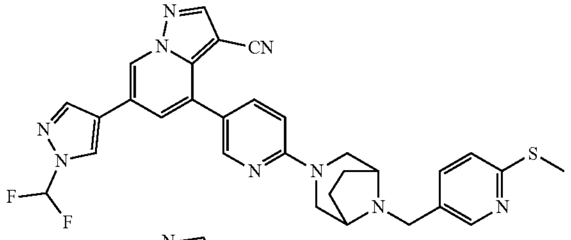
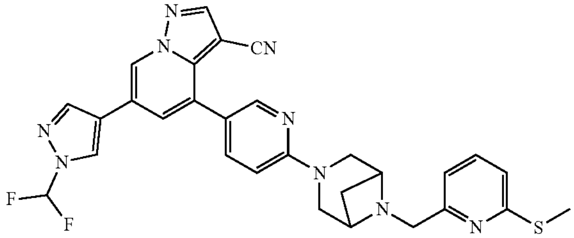
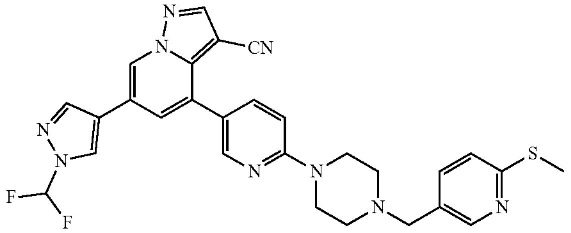
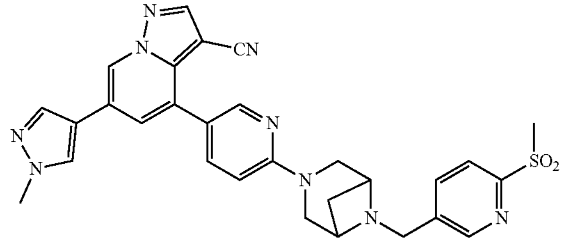
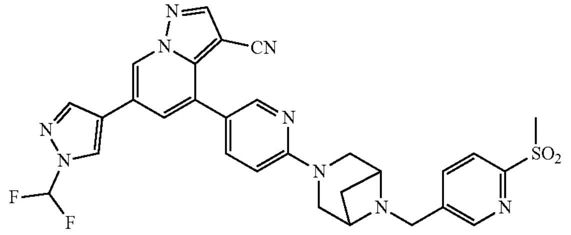
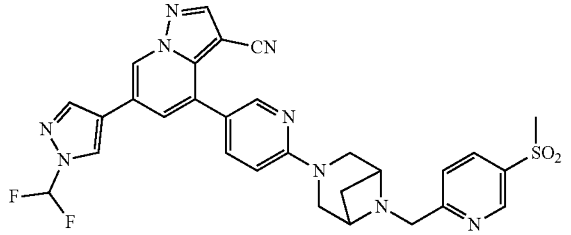
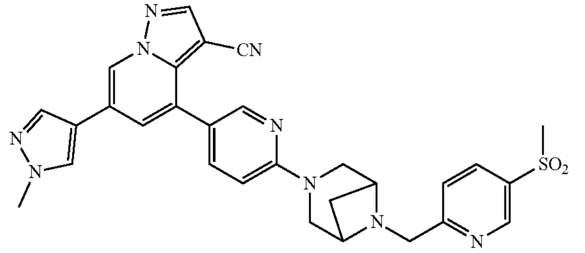
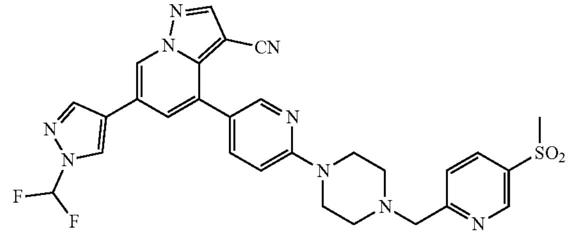
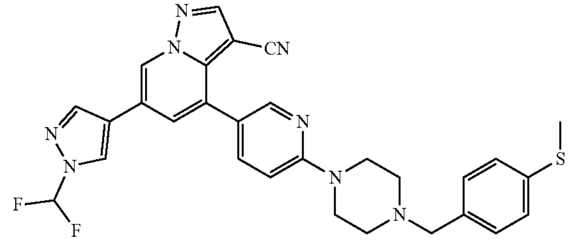
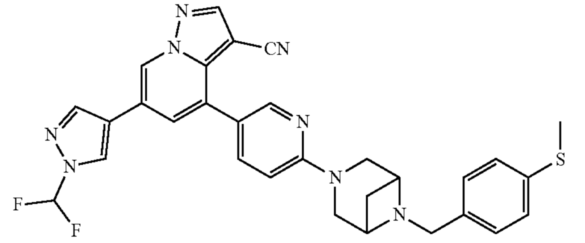
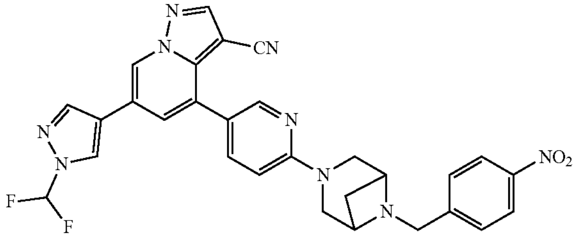
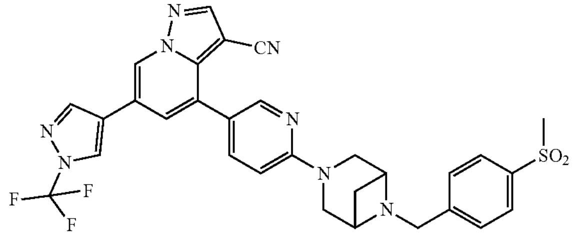
or a pharmaceutically acceptable salt, solvate, polymorph or tautomer thereof.
* * * * *